United States Patent
Rehwinkel et al.

(10) Patent No.: US 8,987,286 B2
(45) Date of Patent: Mar. 24, 2015

(54) SUBSTITUTED PYRIMIDO[1,2-B]INDAZOLES AND THEIR USE AS MODULATORS OF THE PI3K/AKT PATHWAY

(75) Inventors: Hartmut Rehwinkel, Berlin (DE); Andrea Hägebarth, Berlin (DE); Oliver Politz, Panketal OT Zepernick (DE); Roland Neuhaus, Berlin (DE); Ulf Bömer, Glienicke (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/994,517

(22) PCT Filed: Dec. 13, 2011

(86) PCT No.: PCT/EP2011/072593
§ 371 (c)(1),
(2), (4) Date: Aug. 8, 2013

(87) PCT Pub. No.: WO2012/080237
PCT Pub. Date: Jun. 21, 2012

(65) Prior Publication Data
US 2013/0310405 A1  Nov. 21, 2013

(30) Foreign Application Priority Data
Dec. 16, 2010  (EP) .................................... 10195397

(51) Int. Cl.
C07D 487/04 (2006.01)
A61K 31/519 (2006.01)
A61K 45/06 (2006.01)

(52) U.S. Cl.
CPC ............ *C07D 487/04* (2013.01); *A61K 31/519* (2013.01); *A61K 45/06* (2013.01)
USPC ......................................................... 514/267

(58) Field of Classification Search
CPC ...... C07D 487/04; A61K 31/519; A61K 45/06
USPC .......................................... 514/267; 544/267
See application file for complete search history.

(56) References Cited

FOREIGN PATENT DOCUMENTS

WO    WO 2010/104933    *  9/2010    ........... C07D 403/00

* cited by examiner

*Primary Examiner* — Erich A Leeser
(74) *Attorney, Agent, or Firm* — Jonathan R. Harris

(57) ABSTRACT

Compounds of Formula (I), which are effective inhibitors of the Pi3K/Akt pathway, processes for their production and their use as pharmaceuticals. The compounds of formula (I) a: useful for the treatment of cancer.

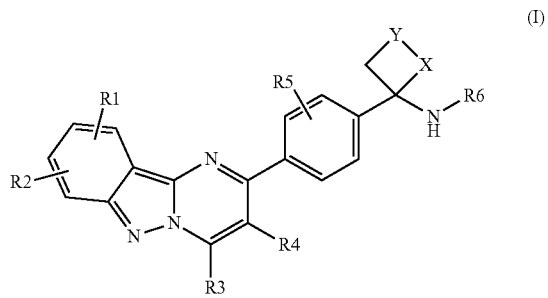

11 Claims, No Drawings

SUBSTITUTED PYRIMIDO[1,2-B]INDAZOLES AND THEIR USE AS MODULATORS OF THE PI3K/AKT PATHWAY

FIELD OF APPLICATION OF THE INVENTION

The invention relates to substituted pyrimido[1,2-b]indazole compounds and a process for their production. The invention also relates to pharmaceutical compositions comprising these compounds as well as methods for using these compounds for the treatment of cancer.

KNOWN TECHNICAL BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

One pathway that has been shown to mediate important survival signals for mammalian cells comprises receptor tyrosine kinases like platelet-derived growth factor receptor (PDGF-R), human epidermal growth factor 2/3 receptor (HER2/3), or the insulin-like growth factor 1 receptor (IGF-1R). After activation the respectives by ligand, these receptors activate the phoshatidylinositol 3-kinase (Pi3K)/Akt pathway. The phoshatidylinositol 3-kinase (Pi3K)/Akt protein kinase pathway is central to the control of cell growth, proliferation and survival, driving progression of tumors. Therefore within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. Akt is mainly activated in a Pi3-kinase dependent manner and the activation is regulated through the tumor suppressor PTEN (phosphatase and tensin homolog), which works essentially as the functional antagonist of Pi3K.

The Pi3K/Akt pathway regulates fundamental cellular functions (e.g. transcription, translation, growth and survival), and is implicated in human diseases including diabetes (Cho et al., 2001, Science 292, 1728-1731) and cancer (Hill and Hemmings, Pharmacology & Therapeutics 93 (2002) 243-251). The pathway is frequently overactivated in a wide range of tumor entities, e.g. breast and prostate carcinomas. Upregulation can be due to overexpression or constitutively activation of receptor tyrosine kinases (e.g. EGFR, HER2/3), which are upstream and involved in its direct activation, or gain- or loss-of-function mutants of some of the components like loss of PTEN. The pathway is targeted by genomic alterations including mutation, amplification and rearrangement more frequently than any other pathway in human cancer, with the possible exception of the p53 and retinoblastoma pathways. The alterations of the Pi3K/Akt pathway trigger a cascade of biological events, that drive tumor progression, survival, angiogenesis and metastasis.

Activation of Akt kinases promotes increased nutrient uptake, converting cells to a glucose-dependent metabolism that redirects lipid precursors and amino acids to anabolic processes that support cell growth and proliferation. These metabolic phenotype with overactivated Akt lead to malignancies that display a metabolic conversion to aerobic glycolysis (the Warburg effect). In that respect the Pi3K/Akt pathway is discussed to be central for survival despite unfavourable growth conditions such as glucose depletion or hypoxia.

A further aspect of the activated PI3K/Akt pathway is to protect cells from programmed cell death ("apoptosis") and is hence considered to transduce a survival signal. By acting as a modulator of anti-apoptotic signalling in tumor cells, the Pi3K/Akt pathway, particular Akt itself is a target for cancer therapy. Activated Akt phosphorylates and regulates several targets, e.g. BAD, GSK3 or FKHRL1, that affect different signalling pathways like cell survival, protein synthesis or cell movement. This Pi3K/Akt pathway also plays a major part in resistance of tumor cells to conventional anti-cancer therapies. Blocking the Pi3K/Akt pathway could therefore simultaneously inhibit the proliferation of tumor cells (e.g. via the inhibition of the metabolic effect) and sensitize towards pro-apoptotic agents.

Because Akt and its upstream regulators are deregulated in a wide range of solid tumors and hematologic malignancies, and in view of the aforementioned biologic sequelae of this pathway, the Akt pathway is considered a key determinant of biologic aggressiveness of these tumors, and a major potential target for novel anti-cancer therapies (Mitsiades et al. Current Cancer Drug Targets, 2004, 4, 235-256).

Akt inhibition selectively sensitized tumor cells to apoptotic stimuli like Trail, Camptothecin and Doxorubicin. Dependent on the genetic background/molecular apperations of tumors, Akt inhibitors might induce apoptotic cell death in monotherapy as well. It is known from Cheng et al (Proc. Natl. Acad. Sci. USA, Vol. 89, pp. 9267-9271, October 1992) that AKT-2 is overexpressed in a number of ovarian cancers as well as pancreatic cancers (Proc. Natl. Acad. Sci. USA Vol. 93, pp. 3636-3641, April 1996). Overexpression of AKT-3 was reported for breast and pancreatic cell lines (Nakatani et al., J Biol. Chem. 274:21528-21532 (1999)). Furthermore, Waugh Kinkade et al (J. Clin. Invest. 118, 9, 3051, 2008) found when conducting their preclinical studies that human prostate cancer tissue microarrays demonstrated that AKT/mTOR and ERK MAPK signaling pathways are often coordinately deregulated during prostate cancer progression in humans and therefore propose that combination therapy targeting AKT/mTOR and ERK MAPK signaling pathways may be an effective treatment for patients with advanced prostate cancer, in particular those with hormone-refractory disease.

Thus in recapturing the above results an inhibition of AKT activity should lead to a successful therapy of cancer, especially the cancer types mentioned above.

In WO 2010104933 Merck, Sharp and Dohme Corp and Banyu Pharmaceuticals CO described tricyclic fused naphthyridine derivatives as inhibitors of AKT kinase activity.

In addition a recent disclosure, Y. Li et al (Bioorg. Med. Chem. Lett. 2009, 19, 834-836 and cited references therein) detail the difficulty in finding optimal Akt inhibitors. The potential application of Akt inhibitors in multiple disease settings, such as for example, cancer, makes the provision of new, improved Akt inhibitors still highly desirable.

DESCRIPTION OF THE INVENTION

A solution to the above problem is the provision of alternative Akt inhibitors. It has been found that the new pyrimido[1,2-b]indazole compounds, which are described in detail below, are Akt inhibitors.

In accordance with a first aspect, the invention relates to compounds of formula (I)

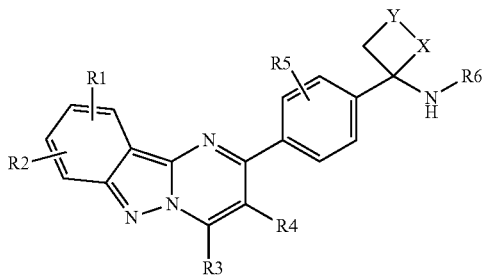

wherein
R1 hydrogen, halogen, cyano, hydroxy, COO(1-6C-alkyl), COOH,
1-6Calkyl,
  which is optionally substituted with hydroxy,
(2-6Calkenyl)
  which is optionally substituted with COO(1-6Calkyl) or (CO)NR7R8,
aryl,
  whereby the aryl ring is optionally substituted one or two times independently by a group selected from halogen, cyano, hydroxy, 1-6C-alkoxy, —SO2-(1-6C-alkyl), —SO2-NR7R8, 1-6C-alkyl, (1-6C-alkylen)OH, COO(1-6C-alkyl), COOH, (CO)NR7R8,
heteroaryl,
  whereby the heteroaryl ring is optionally substituted by 1-3C-alkyl, hydroxy, COO(1-6Calkyl),
R2 is hydrogen, halogen, 1-4Calkyl, 1-4Calkoxy, OCF$_3$, NO$_2$,
R3 is hydrogen, NH(3-7C-cycloalkyl), NH(1-6C-alkyl),
R4 is phenyl optionally substituted by 1-6C-alkyl, halogen, cyano,
R5 is hydrogen, halogen,
X is —CH$_2$—,
Y is —CH$_2$—, —CH(OH)—,
R6 is hydrogen, COO(1-6C-alkyl),
R7, R8 can be the same or different, is hydrogen, 1-6C-alkyl (optionally substituted independently one or more times with a group selected from halogen, hydroxy, mono- or di-1-6C-alkylamino), 1-6C-alkoxy, or 3-7C-cycloalkyl, or,
  in the case of —NR7R8, R7 and R8 together with the nitrogen to which they are attached may also form a 3-6C-heterocyclic ring,
or an N-oxide, a salt, a tautomer or a stereoisomer of said compound, or a salt of said N-oxide, tautomer or stereoisomer.

A further aspect of the invention are compounds of formula I according to claim 1 wherein
R1 is hydrogen, halogen, cyano, hydroxy, COO(1-6C-alkyl), COOH,
1-6Calkyl,
  which is optionally substituted with hydroxy,
(2-6Calkenyl)
  which is optionally substituted with COO(1-6Calkyl) or (CO)NR7R8,
aryl,
  whereby the aryl ring is optionally substituted one or two times independently by a group selected from halogen, cyano, hydroxy, 1-6C-alkoxy, —SO2-(1-6C-alkyl), —SO2-NR7R8, 1-6C-alkyl, (1-6C-alkylen)OH, COO(1-6C-alkyl), COOH, (CO)NR7R8,
heteroaryl,
  whereby the heteroaryl ring is optionally substituted by hydroxy, COO(1-6Calkyl),
R2 is hydrogen, halogen, 1-4Calkyl, 1-4Calkoxy, OCF$_3$, NO$_2$,
R3 is hydrogen, NH(3-7C-cycloalkyl), NH(1-6C-alkyl),
R4 is phenyl optionally substituted by 1-6C-alkyl, halogen, cyano,
R5 is hydrogen, halogen,
X is —CH$_2$—,
Y is —CH$_2$—, —CH(OH)—,
R6 is hydrogen, COO(1-6C-alkyl),
R7, R8 can be the same or different, is hydrogen, 1-6C-alkyl (optionally substituted independently one or more times with a group selected from halogen, hydroxy, mono- or di-1-6C-alkylamino), 1-6C-alkoxy, or 3-7C-cycloalkyl, or,
  in the case of —NR7R8, R7 and R8 together with the nitrogen to which they are attached may also form a 3-6C-heterocyclic ring,
or an N-oxide, a salt, a tautomer or a stereoisomer of said compound, or a salt of said N-oxide, tautomer or stereoisomer.

Another aspect of the invention are compounds of formula I according to claim 1 wherein
R1 is halogen, cyano, hydroxy, COOH, COO(1-4C-alkyl), (1-4Calkyl),
  which is optionally substituted with hydroxy,
(2-4Calkenyl)
  which is optionally substituted with COO(1-4Calkyl) or (CO)NR7R8,
phenyl,
  whereby the phenyl ring is optionally substituted one or two times independently by
  a group selected from halogen, cyano, hydroxy, 1-4C-alkoxy, (1-4C-alkyl)-SO2, 1-4C-alkyl, hydroxy(1-4C-alkyl), COO(1-4C-alkyl), (CO)NR7R8,
heteroaryl,
  whereby the heteroaryl group is optionally substituted by 1-3C-alkyl, hydroxy or COO(1-4Calkyl),
R2 is hydrogen,
R3 is hydrogen, NH(3-6C-cycloalkyl), NH(1-4C-alkyl),
R4 is phenyl,
R5 is hydrogen,
X is —CH$_2$—,
Y is —CH$_2$—, —CH(OH)—,
R6 is hydrogen, COO(1-4C-alkyl),
R7, R8 can be the same or different, is hydrogen, 1-4C-alkyl (optionally substituted independently one or more times with a group selected from halogen, hydroxy, mono- or di-1-4C-alkylamino), 1-4C-alkoxy, or 3-7C-cycloalkyl, or,
  in the case of —NR7R8, R7 and R8 together with the nitrogen to which they are attached may also form a 3-6C-heterocyclic ring,
or an N-oxide, a salt, a tautomer or a stereoisomer of said compound, or a salt of said N-oxide, tautomer or stereoisomer.

Another aspect of the invention are compounds of formula I according to claim 1 wherein
R1 is halogen, cyano, hydroxy, COOH, COO(1-4C-alkyl), (1-4Calkyl),
  which is optionally substituted with hydroxy, (2-4Calkenyl)
  which is optionally substituted with COO(1-4Calkyl) or (CO)NR7R8,
phenyl,
  whereby the phenyl ring is optionally substituted one or two times independently by
    a group selected from halogen, cyano, hydroxy, C1-C4-alkoxy, (1-4C-alkyl)-SO2, 1-4C-alkyl, hydroxy(1-4C-alkyl), COO(1-4C-alkyl), (CO)NR7R8,
heteroaryl,
  whereby the heteroaryl group is optionally substituted by hydroxyl or COO(1-4Calkyl),
R2 is hydrogen,
R3 is hydrogen, NH(3-6C-cycloalkyl), NH(1-4C-alkyl),
R4 is phenyl,
R5 is hydrogen,
X is —CH$_2$—,
Y is —CH$_2$—, —CH(OH)—,
R6 is hydrogen, COO(1-4C-alkyl),
R7, R8 can be the same or different, is hydrogen, 1-4C-alkyl
  (optionally substituted independently one or more times with a group selected from halogen, hydroxy, mono- or di-1-4C-alkylamino), 1-4C-alkoxy, or 3-7C-cycloalkyl, or, in the case of —NR7R8, R7 and R8 together with the nitrogen to which they are attached may also form a 3-6C-heterocyclic ring,
or an N-oxide, a salt, a tautomer or a stereoisomer of said compound, or a salt of said N-oxide, tautomer or stereoisomer.

A further aspect of the invention are compounds of formula I according to claim 1 wherein
R1 F, Br, cyano, hydroxy, COOCH3, CH2OH, —C2H2-COOCH3, —C2H2-CONH2, —CH=CH—(CO)—OCH3, —CH=CH—(CO)—NH2,
1H-pyrazol-4-yl, 1H-pyrazol-5-yl, 3-pyridyl,
  whereby the pyrazole and pyridinyl group is optionally substituted by methyl, hydroxy or COOCH3,
phenyl,
  whereby the phenyl ring is substituted one or two times independently by
    a group selected from F, cyano, hydroxy, methoxy, SO2CH3, SO2NH2, methyl, CH2OH, COOCH3, CONH2,
R2 hydrogen,
R3 hydrogen, NH(cyclopropyl), NHCH3,
R4 phenyl,
R5 hydrogen,
X is —CH$_2$—,
Y is —CH$_2$—,
R6 hydrogen, COOC(CH3)3,
or an N-oxide, a salt, a tautomer or a stereoisomer of said compound, or a salt of said N-oxide, tautomer or stereoisomer.

A further aspect of the invention are compound of formula I according to claim 1 wherein
R1 F, Br, cyano, hydroxy, COOCH3, CH2OH, —C2H2-COOCH3, —C2H2-CONH2,
1H-pyrazol-4-yl, 3-pyridyl,
  whereby the pyrazole and pyridinyl group is optionally substituted by hydroxy or COOCH3,
phenyl,
  whereby the phenyl ring is substituted one or two times independently by
    a group selected from F, cyano, hydroxy, methoxy, SO2CH3, SO2NH2, methyl, CH2OH, COOCH3, CONH2,
R2 hydrogen,
R3 hydrogen, NH(cyclopropyl), NHCH3,
R4 phenyl,
R5 hydrogen,
X is —CH$_2$—,
Y is —CH$_2$—,
R6 hydrogen, COOC(CH3)3,
or an N-oxide, a salt, a tautomer or a stereoisomer of said compound, or a salt of said N-oxide, tautomer or stereoisomer.

In one aspect of the invention compounds of formula (I) as described above are selected from the group consisting of:
1-[4-(9-Fluoro-3-phenylpyrimido[1,2-b]indazol-2-yl)phenyl]cyclobutylamine
2-[4-(1-Aminocyclobutyl)phenyl]-N-cyclopropyl-9-fluoro-3-phenylpyrimido[1,2-b]indazol-4-amine
2-[4-(1-Aminocyclobutyl)phenyl]-N-methyl-9-fluoro-3-phenylpyrimido[1,2-b]indazol-4-amine
3-{2-[4-(1-Aminocyclobutyl)phenyl]-3-phenyl-pyrimido[1,2-b]indazol-8-yl}benzonitrile
1-{4-[8-(4-Mesylphenyl)-3-phenylpyrimido[1,2-b]indazol-2-yl]-phenyl}cyclobutylamine
1-{4-[8-(4-Fluorophenyl)-3-phenylpyrimido[1,2-b]indazol-2-yl]-phenyl}cyclobutylamine
1-[4-(8-Bromo-3-phenylpyrimido[1,2-b]indazol-2-yl)phenyl]cyclobutylamine hydrochloride
5-{2-[4-(1-Aminocyclobutyl)phenyl]-3-phenylpyrimido[1,2-b]indazol-8-yl}-2-fluorobenzyl alcohol
5-{2-[4-(1-Aminocyclobutyl)phenyl]-3-phenylpyrimido[1,2-b]indazol-8-yl}-2-fluorophenol formiate
1-{4-[8-(4-Fluoro-3-methoxyphenyl)-3-phenylpyrimido[1,2-b]indazol-2-yl]phenyl}cyclobutylamine
1-{4-[8-(3-Mesylphenyl)-3-phenylpyrimido[1,2-b]indazol-2-yl]phenyl}cyclobutylamine formiate
2-[4-(1-Aminocyclobutyl)phenyl]-3-phenylpyrimido[1,2-b]indazole-8-carboxylic acid methyl ester
3-{2-[4-(1-Aminocyclobutyl)phenyl]-3-phenylpyrimido[1,2-b]indazol-8-yl}benzamide
4-{2-[4-(1-Aminocyclobutyl)phenyl]-3-phenylpyrimido[1,2-b]indazol-8-yl}benzamide
1-{4-[3-Phenyl-8-(1H-pyrazol-4-yl)pyrimido[1,2-b]indazol-2-yl]-phenyl}cyclobutylamine
5-{2-[4-(1-Aminocyclobutyl)phenyl]3-phenylpyrimido[1,2-b]indazol-8-yl}pyridin-2-ol
5-{2-[4-(1-Aminocyclobutyl)phenyl]-3-phenylpyrimido[1,2-b]indazol-8-yl}pyridine-2-carboxylic acid methyl ester
1-{4-[9-(4-Fluorophenyl)-3-phenylpyrimido[1,2-b]indazol-2-yl]phenyl}-cyclobutylamine
1-[4-(3-Phenyl-9-p-tolylpyrimido[1,2-b]indazol-2-yl)phenyl]cyclobutylamine
3-{2-[4-(1-Aminocyclobutyl)phenyl]-3-phenylpyrimido[1,2-b]indazol-9-yl}benzoic acid methyl ester
3-{2-[4-(1-Aminocyclobutyl)phenyl]-3-phenylpyrimido[1,2-b]indazol-9-yl}benzonitrile
1-[4-(9-Bromo-3-phenylpyrimido[1,2-b]indazol-2-yl)phenyl]cyclobutylamine
4-{2-[4-(1-Aminocyclobutyl)phenyl]-3-phenylpyrimido[1,2-b]indazol-9-yl}benzonitrile formiate
3-{2-[4-(1-Aminocyclobutyl)phenyl]-3-phenylpyrimido[1,2-b]indazol-9-yl}benzyl alcohol formiate
4-{2-[4-(1-Aminocyclobutyl)phenyl]-3-phenylpyrimido[1,2-b]indazol-9-yl}benzyl alcohol formiate
4-{2-[4-(1-Aminocyclobutyl)phenyl]-3-phenylpyrimido[1,2-b]indazol-9-yl}benzenesulfonamide formiate
5-{2-[4-(1-Aminocyclobutyl)phenyl]-3-phenylpyrimido[1,2-b]indazol-9-yl}-2-fluorobenzyl alcohol
1-{4-[3-Phenyl-9-(1H-pyrazol-4-yl)pyrimido[1,2-b]indazol-2-yl]phenyl}-cyclobutylamine 4-{2-[4-(1-Aminocyclobutyl)phenyl]-3-phenylpyrimido[1,2-b]indazol-10-yl}benzonitrile formiate
1-[4-(3-Phenyl-10-p-tolylpyrimido[1,2-b]indazol-2-yl)phenyl]cyclobutylamine×0.5 formiate
1-{4-[10-(4-Fluorophenyl)-3-phenylpyrimido[1,2-b]indazol-2-yl]-phenyl}cyclobutylamine formiate
4-{2-[4-(1-Aminocyclobutyl)phenyl]-3-phenylpyrimido[1,2-b]indazol-10-yl}benzyl alcohol formiate
3-{2-[4-(1-Aminocyclobutyl)phenyl]-3-phenylpyrimido[1,2-b]indazol-7-yl}benzonitrile
1-[4-(7-Bromo-3-phenylpyrimido[1,2-b]indazol-2-yl)phenyl]cyclobutylamine hydrochloride
1-{4-[7-(4-Fluorophenyl)-3-phenylpyrimido[1,2-b]indazol-2-yl]-phenyl}cyclobutylamine
4-{2-[4-(1-Aminocyclobutyl)phenyl]-3-phenylpyrimido[1,2-b]indazol-7-yl}benzyl alcohol formiate
1-{4-[7-(3-Mesylphenyl)-3-phenylpyrimido[1,2-b]indazol-2-yl]-phenyl}cyclobutylamine
1-{4-[3-Phenyl-7-(1H-pyrazol-4-yl)pyrimido[1,2-b]indazol-2-yl]-phenyl}cyclobutylamine×0.5 formiate
2-[4-(1-Aminocyclobutyl)phenyl]-3-phenylpyrimido[1,2-b]indazole-7-carbonitrile
2-[4-(1-Aminocyclobutyl)phenyl]-3-phenylpyrimido[1,2-b]indazole-7-carboxylic acid methyl ester formiate
2-[4-(1-Aminocyclobutyl)phenyl]-3-phenylpyrimido[1,2-b]indazol-7-ol
{2-[4-(1-Aminocyclobutyl)phenyl]-3-phenylpyrimido[1,2-b]indazol-7-yl}methanol
(E)-3-{2-[4-(1-Aminocyclobutyl)phenyl]-3-phenylpyrimido[1,2-b]indazol-7-yl}acrylic acid methyl ester
(E)-3-{2-[4-(1-Aminocyclobutyl)phenyl]-3-phenylpyrimido[1,2-b]indazol-7-yl}acrylamide
or an N-oxide, a salt, a tautomer or a stereoisomer of said compound, or a salt of said N-oxide, tautomer or stereoisomer.

Another aspect of the invention compounds of formula (I) as described above are selected from the group consisting of:
1-[4-(9-Fluoro-3-phenylpyrimido[1,2-b]indazol-2-yl)phenyl]cyclobutylamine
2-[4-(1-Aminocyclobutyl)phenyl]-N-cyclopropyl-9-fluoro-3-phenylpyrimido[1,2-b]indazol-4-amine
2-[4-(1-Aminocyclobutyl)phenyl]-N-methyl-9-fluoro-3-phenylpyrimido[1,2-b]indazol-4-amine
3-{2-[4-(1-Aminocyclobutyl)phenyl]-3-phenyl-pyrimido[1,2-b]indazol-8-yl}benzonitrile
1-{4-[8-(4-Mesylphenyl)-3-phenylpyrimido[1,2-b]indazol-2-yl]-phenyl}cyclobutylamine
1-{4-[8-(4-Fluorophenyl)-3-phenylpyrimido[1,2-b]indazol-2-yl]-phenyl}cyclobutylamine
1-[4-(8-Bromo-3-phenylpyrimido[1,2-b]indazol-2-yl)phenyl]cyclobutylamine hydrochloride
5-{2-[4-(1-Aminocyclobutyl)phenyl]-3-phenylpyrimido[1,2-b]indazol-8-yl}-2-fluorobenzyl alcohol
5-{2-[4-(1-Aminocyclobutyl)phenyl]-3-phenylpyrimido[1,2-b]indazol-8-yl}-2-fluorophenol formiate
1-{4-[8-(4-Fluoro-3-methoxyphenyl)-3-phenylpyrimido[1,2-b]indazol-2-yl]phenyl}cyclobutylamine
1-{4-[8-(3-Mesylphenyl)-3-phenylpyrimido[1,2-b]indazol-2-yl]phenyl}cyclobutylamine formiate
2-[4-(1-Aminocyclobutyl)phenyl]-3-phenylpyrimido[1,2-b]indazole-8-carboxylic acid methyl ester
3-{2-[4-(1-Aminocyclobutyl)phenyl]-3-phenylpyrimido[1,2-b]indazol-8-yl}benzamide
4-{2-[4-(1-Aminocyclobutyl)phenyl]-3-phenylpyrimido[1,2-b]indazol-8-yl}benzamide
1-{4-[3-Phenyl-8-(1H-pyrazol-4-yl)pyrimido[1,2-b]indazol-2-yl]-phenyl}cyclobutylamine
5-{2-[4-(1-Aminocyclobutyl)phenyl]3-phenylpyrimido[1,2-b]indazol-8-yl}pyridin-2-ol
5-{2-[4-(1-Aminocyclobutyl)phenyl]-3-phenylpyrimido[1,2-b]indazol-8-yl}pyridine-2-carboxylic acid methyl ester
1-{4-[9-(4-Fluorophenyl)-3-phenylpyrimido[1,2-b]indazol-2-yl]phenyl}-cyclobutylamine
1-[4-(3-Phenyl-9-p-tolylpyrimido[1,2-b]indazol-2-yl)phenyl]cyclobutylamine
3-{2-[4-(1-Aminocyclobutyl)phenyl]-3-phenylpyrimido[1,2-b]indazol-9-yl}benzoic acid methyl ester
3-{2-[4-(1-Aminocyclobutyl)phenyl]-3-phenylpyrimido[1,2-b]indazol-9-yl}benzonitrile
1-[4-(9-Bromo-3-phenylpyrimido[1,2-b]indazol-2-yl)phenyl]cyclobutylamine
4-{2-[4-(1-Aminocyclobutyl)phenyl]-3-phenylpyrimido[1,2-b]indazol-9-yl}benzonitrile formiate
3-{2-[4-(1-Aminocyclobutyl)phenyl]-3-phenylpyrimido[1,2-b]indazol-9-yl}benzyl alcohol formiate
4-{2-[4-(1-Aminocyclobutyl)phenyl]-3-phenylpyrimido[1,2-b]indazol-9-yl}benzyl alcohol formiate
4-{2-[4-(1-Aminocyclobutyl)phenyl]-3-phenylpyrimido[1,2-b]indazol-9-yl}benzenesulfonamide formiate
5-{2-[4-(1-Aminocyclobutyl)phenyl]-3-phenylpyrimido[1,2-b]indazol-9-yl}-2-fluorobenzyl alcohol
1-{4-[3-Phenyl-9-(1H-pyrazol-4-yl)pyrimido[1,2-b]indazol-2-yl]phenyl}-cyclobutylamine
4-{2-[4-(1-Aminocyclobutyl)phenyl]-3-phenylpyrimido[1,2-b]indazol-10-yl}benzonitrile formiate
1-[4-(3-Phenyl-10-p-tolylpyrimido[1,2-b]indazol-2-yl)phenyl]cyclobutylamine×0.5 formiate
1-{4-[10-(4-Fluorophenyl)-3-phenylpyrimido[1,2-b]indazol-2-yl]-phenyl}cyclobutylamine formiate
4-{2-[4-(1-Aminocyclobutyl)phenyl]-3-phenylpyrimido[1,2-b]indazol-10-yl}benzyl alcohol formiate
3-{2-[4-(1-Aminocyclobutyl)phenyl]-3-phenylpyrimido[1,2-b]indazol-7-yl}benzonitrile
1-[4-(7-Bromo-3-phenylpyrimido[1,2-b]indazol-2-yl)phenyl]cyclobutylamine hydrochloride
1-{4-[7-(4-Fluorophenyl)-3-phenylpyrimido[1,2-b]indazol-2-yl]-phenyl}cyclobutylamine
4-{2-[4-(1-Aminocyclobutyl)phenyl]-3-phenylpyrimido[1,2-b]indazol-7-yl}benzyl alcohol formiate
1-{4-[7-(3-Mesylphenyl)-3-phenylpyrimido[1,2-b]indazol-2-yl]-phenyl}cyclobutylamine
1-{4-[3-Phenyl-7-(1H-pyrazol-4-yl)pyrimido[1,2-b]indazol-2-yl]-phenyl}cyclobutylamine×0.5 formiate
2-[4-(1-Aminocyclobutyl)phenyl]-3-phenylpyrimido[1,2-b]indazole-7-carbonitrile
2-[4-(1-Aminocyclobutyl)phenyl]-3-phenylpyrimido[1,2-b]indazole-7-carboxylic acid methyl ester formiate
2-[4-(1-Aminocyclobutyl)phenyl]-3-phenylpyrimido[1,2-b]indazol-7-ol
{2-[4-(1-Aminocyclobutyl)phenyl]-3-phenylpyrimido[1,2-b]indazol-7-yl}methanol
(E)-3-{2-[4-(1-Aminocyclobutyl)phenyl]-3-phenylpyrimido[1,2-b]indazol-7-yl}acrylic acid methyl ester
(E)-3-{2-[4-(1-Aminocyclobutyl)phenyl]-3-phenylpyrimido[1,2-b]indazol-7-yl}acrylamide
1-{4-[3-Phenyl-8-(1H-pyrazol-5-yl)-pyrimido[1,2-b]indazol-2-yl]-phenyl}cyclobutylamine
1-{4-[8-(3-Methyl-1H-pyrazol-5-yl)-3-phenylpyrimido[1,2-b]indazol-2-yl]phenyl}cyclobutylamine
1-{4-[3-Phenyl-9-(1H-pyrazol-5-yl)pyrimido[1,2-b]indazol-2-yl]-phenyl}cyclobutylamine
1-{4-[9-(3-Methyl-1H-pyrazol-5-yl)-3-phenylpyrimido[1,2-b]indazol-2-yl]phenyl}cyclobutylamine (E)-3-{2-[4-(1-Aminocyclobutyl)phenyl]-3-phenylpyrimido[1,2-b]indazol-9-yl}acrylic acid methyl ester (E)-3-{2-[4-(1-Aminocyclobutyl)phenyl]-3-phenylpyrimido[1,2-b]indazol-9-yl}acrylamide or an N-oxide, a salt, a tautomer or a stereoisomer of said compound, or a salt of said N-oxide, tautomer or stereoisomer.

A further aspect of the invention compounds of formula (I) as described above are selected from the group consisting of:

1-{4-[3-Phenyl-8-(1H-pyrazol-5-yl)-pyrimido[1,2-b]indazol-2-yl]-phenyl}cyclobutylamine 1-{4-[8-(3-Methyl-1H-pyrazol-5-yl)-3-phenylpyrimido[1,2-b]indazol-2-yl]phenyl}cyclobutylamine 1-{4-[3-Phenyl-9-(1H-pyrazol-5-yl)pyrimido[1,2-b]indazol-2-yl]-phenyl}cyclobutylamine 1-{4-[9-(3-Methyl-1H-pyrazol-5-yl)-3-phenylpyrimido[1,2-b]indazol-2-yl]phenyl}cyclobutylamine (E)-3-{2-[4-(1-Aminocyclobutyl)phenyl]-3-phenylpyrimido[1,2-b]indazol-9-yl}acrylic acid methyl ester (E)-3-{2-[4-(1-Aminocyclobutyl)phenyl]-3-phenylpyrimido[1,2-b]indazol-9-yl}acrylamide or an N-oxide, a salt, a tautomer or a stereoisomer of said compound, or a salt of said N-oxide, tautomer or stereoisomer.

One aspect of the present invention are the compounds disclosed in the examples as well as the intermediates as used for their synthesis.

Another aspect of the invention are intermediates of formula (II)

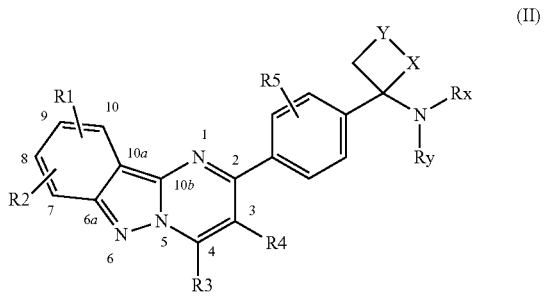

Wherein R1 is bromine in position 7, 8 or 9 of the tricyclic ring system and R2 is hydrogen and R3, R4, R5, X, Y, Rx and Ry have the meaning as defined in claim 1.

Preferred intermediates are the compounds 2-0, 2-1 and 2-2 disclosed in the examples section.

Another aspect of the invention are compounds of formula (I), wherein
R1 is hydrogen, halogen, cyano, hydroxy, COO(1-6C-alkyl), COOH,
1-6Calkyl,
   which is optionally substituted with hydroxy
(2-6Calkenyl)
   which is optionally substituted with COO(1-6Calkyl) or CONR7R8,
aryl,
   whereby the aryl ring is optionally substituted one or two times independently by a group selected from halogen, cyano, hydroxy, 1-6C-alkoxy, —SO2-(1-6C-alkyl), —SO2-NR7R8, 1-6C-alkyl, (1-6C-alkylen)OH, COO(1-6C-alkyl), COOH, —CO—NR7R8, CONR7R8, heteroaryl,
   whereby the heteroaryl ring is optionally substituted by hydroxy, COO(1-6Calkyl),
and R2 is hydrogen.

Another aspect of the invention are compounds of formula (I), wherein
R1 is hydrogen, halogen, cyano, hydroxy, COO(1-6C-alkyl), COOH,
1-6Calkyl,
   which is optionally substituted with hydroxy
(2-6Calkenyl)
   which is optionally substituted with COO(1-6Calkyl) or CONR7R8, aryl, whereby the aryl ring is optionally substituted one or two times independently by a group selected from halogen, cyano, hydroxy, 1-6C-alkoxy, —SO2-(1-6C-alkyl), —SO2-NR7R8, 1-6C-alkyl, (1-6C-alkylen)OH, COO(1-6C-alkyl), COOH, —CO—NR7R8, CONR7R8,
heteroaryl,
   whereby the heteroaryl ring is optionally substituted by hydroxy, COO(1-6Calkyl),
R2 is hydrogen, halogen, 1-4Calkyl, 1-4Calkoxy, OCF$_3$, NO$_2$,
And R3=R4=R5=R6=hydrogen.

Another aspect of the invention are compounds of formula (I), wherein R1 is hydrogen, halogen, cyano, hydroxy, COO(1-6C-alkyl), COOH,
1-6Calkyl,
   which is optionally substituted with hydroxy
(2-6Calkenyl)
   which is optionally substituted with COO(1-6Calkyl) or CONR7R8, aryl, whereby the aryl ring is optionally substituted one or two times independently by a group selected from halogen, cyano, hydroxy, 1-6C-alkoxy, —SO2-(1-6C-alkyl), —SO2-NR7R8, 1-6C-alkyl, (1-6C-alkylen)OH, COO(1-6C-alkyl), COOH, —CO—NR7R8, CONR7R8,
heteroaryl,
   whereby the heteroaryl ring is optionally substituted by hydroxy, COO(1-6Calkyl), Another aspect of the invention are compounds of formula (I), wherein
R1 is halogen, cyano, hydroxy, COOH, COO(1-4C-alkyl),
(1-4Calkyl),
   which is optionally substituted with hydroxy
(2-4Calkenyl)
   which is optionally substituted with COO(1-4Calkyl) or CONR7R8,
phenyl,
   whereby the phenyl ring is optionally substituted one or two times independently by
   a group selected from halogen, cyano, hydroxy, C1-C4-alkoxy, (1-4C-alkyl)-SO2, 1-4C-alkyl, hydroxy(1-4C-alkyl), COO(1-4C-alkyl), CONR7R8
heteroaryl,
   whereby the heteroaryl group is optionally substituted by hydroxyl or COO(1-4Calkyl),
Another aspect of the invention are compounds of formula (I), wherein
R1 is F, Br, cyano, hydroxy, COOCH3, CH2OH, —C2H2-COOCH3, —C2H2-CONH2,
1H-pyrazol-4-yl, 3-pyridyl,
   whereby the pyrazole and pyridinyl group is optionally substituted by hydroxy or COOCH3, phenyl,
whereby the phenyl ring is substituted one or two times independently by a group selected from F, cyano, hydroxy, methoxy, SO2CH3, SO2NH2, methyl, CH2OH, COOCH3, CONH2

A further aspect of the invention are compounds of formula (I), wherein
R1 is aryl,
whereby the aryl ring is optionally substituted one or two times independently by a group selected from halogen, cyano, hydroxy, 1-6C-alkoxy, —SO2-(1-6C-alkyl), —SO2-NR7R8, 1-6C-alkyl, (1-6C-alkylen)OH, COO (1-6C-alkyl), COOH, —CO—NR7R8, CONR7R8,
or heteroaryl,
whereby the heteroaryl ring is optionally substituted by hydroxy, COO(1-6Calkyl), A further aspect of the invention are compounds of formula (I), wherein
R1 is aryl, whereby the aryl ring is optionally substituted one or two times independently by a group selected from halogen, cyano, hydroxy, 1-6C-alkoxy, —SO2-(1-6C-alkyl), —SO2-NR7R8, 1-6C-alkyl, (1-6C-alkylen)OH, COO(1-6C-alkyl), COOH, —CO—NR7R8, CONR7R8, preferably wherein R1 is phenyl, whereby the phenyl ring is substituted one or two times independently by a group selected from F, cyano, hydroxy, methoxy, SO2CH3, SO2NH2, methyl, CH2OH, COOCH3, CONH2.

A further aspect of the invention are compounds of formula (I), wherein
R1 is heteroaryl, whereby the heteroaryl ring is optionally substituted by hydroxy, COO(1-6Calkyl), preferably wherein R1 is pyrazolyl or pyridinyl,
whereby the pyrazole and pyridyl group is optionally substituted by hydroxy or COOCH3, more preferably wherein R1 is 1H-pyrazol-4-yl or 3-pyridinyl,
whereby the pyrazole and pyridinyl group is optionally substituted by hydroxy or COOCH3.

A further aspect of the invention are compounds of formula (I), wherein
R1 is —CH=CH—(CO)—OCH3, —CH=CH—(CO)—NH2.

A further aspect of the invention are compounds of formula (I), wherein
R1 is pyrazoly, preferably 1H-pyrazol-4-yl or 1H-pyrazol-5-yl.

A further aspect of the invention are compounds of formula (I), wherein
R1 is pyrazoly, preferably 1H-pyrazol-4-yl or 1H-pyrazol-5-yl which are optionally substituted with methyl, hydroxy or COOCH3

A further aspect of the invention are compounds of formula (I), wherein
R1 is pyrazoly, preferably 1H-pyrazol-4-yl.

A further aspect of the invention are compounds of formula (I), wherein
R1 is pyridinyl, preferably 3-pyridinyl.

Another aspect of the invention are compounds of formula (I), wherein the alkyl residue R1 is unsubstituted.

Another aspect of the invention are compounds of formula (I), wherein
R2 is hydrogen.

A further aspect of the invention are compounds of formula (I), wherein
R2 is hydrogen, F, Cl, Br, I, Methyl, OCH$_3$, OCF$_3$, NO$_2$.

Another aspect of the invention are compounds of formula (I), wherein
R3 is hydrogen.

A further aspect of the invention are compounds of formula (I), wherein
R3 is hydrogen, NH(3-7C-cycloalkyl) or NH(1-6C-alkyl), preferably hydrogen, NH(cyclopropyl), NHCH3.

Another aspect of the invention are compounds of formula (I), wherein
R4 is phenyl optionally substituted by 1-6C-alkyl, halogen, cyano.

A further aspect of the invention are compounds of formula (I), wherein
R4 is unsubstituted phenyl.

Another aspect of the invention are compounds of formula (I), wherein
R5 is hydrogen or halogen.

A further aspect of the invention are compounds of formula (I), wherein
R5 is hydrogen.

Another aspect of the invention are compounds of formula (I), wherein
R6 is any protecting group suitable to protect the amino function according to T. W. Greene, Protective Groups in Organic Synthesis, John Wiley & Sons, 1999, 3rd Ed., or in P. Kocienski, Protecting Groups, Thieme Medical Publishers, 2000, especially COO(1-6C-alkyl).

A further aspect of the invention are compounds of formula (I), wherein
R6 is hydrogen, COO(1-6C-alkyl).

Another aspect of the invention are compounds of formula (I), wherein
R7, R8 is the same or different, and is hydrogen, 1-6C-alkyl (optionally substituted independently one or more times with a group selected from halogen, hydroxy, mono- or di-1-6C-alkylamino), 1-6C-alkoxy, or 3-7C-cycloalkyl,
or, in the case of —NR7R8, R7 and R8 together with the nitrogen to which they are attached may also form a 3-6C-heterocyclic ring, A further aspect of the invention are compounds of formula (I), wherein
R7, R8 is in the case of —NR7R8, if R7 and R8 together with the nitrogen to which they are attached also form a 3-6C-heterocyclic ring.

A further aspect of the invention are compounds of formula (I), wherein
X is —CH$_2$—, and Y is —CH$_2$—, —CH(OH)—.

A further aspect of the invention are compounds of formula (I), wherein
X is —CH$_2$— and Y is —CH$_2$—

Most preferred are the radicals as disclosed specifically for each residue in the examples.

DEFINITIONS

The term "1-6C-alkyl" is a straight-chain or branched alkyl group having 1 to 6 carbon atoms. Examples are methyl, ethyl, n-propyl, iso-propyl, n butyl, iso-butyl, sec-butyl and tert-butyl, pentyl, hexyl, preferably 1-4 carbon atoms (1-4C-alkyl), more preferably 1-3 carbon atoms (1-3C-alkyl). Other alkyl constituents mentioned herein having another number of carbon atoms shall be defined as mentioned above taking into account the different length of their chain.

The term "hydroxy(1-6Calkyl)" group consequently means an alkyl group as defined above and substituting just one hydrogen atom by a hydroxy substituent at any possible position of the chain.

The term 2-6C-Alkenyl is a straight chain or branched alkenyl radical having 2 to 6 carbon atoms. Examples are the but-2-enyl, but-3-enyl (homoallyl), prop-1-enyl, prop-2-enyl (allyl) and the ethenyl (vinyl) radicals.

The term "Mono- or di-1-4C-alkylamino" radicals contain in addition to the nitrogen atom, independently one or two of the above mentioned 1-4C-alkyl radicals. Examples are the methyamino, the ethylamino, the isopropylamino, the dimethylamino, the diethylamino and the diisopropylamino radical.

The term "aryrl" is a mono- to tricyclic aromatic, carbocyclic radical having 6 to 14 carbon atoms; e.g. phenyl, naphthyl or phenanthrenyl.

The term "Halogen" within the meaning of the present invention is iodine, bromine, chlorine or fluorine, preferably "halogen" within the meaning of the present invention is chlorine or fluorine.

The term "1-6C-Alkoxy" represents radicals, which in addition to the oxygen atom, contain a straight-chain or branched alkyl radical having 1 to 6 carbon atoms. Examples which may be mentioned are the hexoxy, pentoxy, butoxy, iso-butoxy, sec-butoxy, tert-butoxy, pro-poxy, iso-propoxy, ethoxy and methoxy radicals, preferred are methoxy, ethoxy, propoxy, isopropoxy.

The term "3-7C-Cycloalkyl" stands for cyclopropyl, cyclobutyl, cyclopentyl, cyclohexyl or cycloheptyl, preferably cyclopropyl.

The term "heteroaryl" includes monocyclic 5- or 6-membered heteroaryl groups comprising without being restricted thereto, the 5-membered heteroaryl radicals furyl, thienyl, pyrrolyl, oxazolyl, isoxazolyl, thiazolyl, isothiazolyl, imidazolyl, pyrazolyl (especially 1H-pyrazolyl-4-yl), triazolyl(1,2,4-triazolyl, 1,3,4-triazolyl or 1,2,3-triazolyl), thiadiazolyl(1,3,4-thiadiazolyl, 1,2,5-thiadiazolyl, 1,2,3-thiadiazolyl or 1,2,4-thiadiazolyl) and oxadiazolyl(1,3,4-oxadiazolyl, 1,2,5-oxadiazolyl, 1,2,3-oxadiazolyl or 1,2,4-oxadiazolyl), as well as the 6-membered heteroaryl radicals pyridinyl(2-pyridyl, 3-pyridyl, 4-pyridyl), pyrimidinyl, pyrazinyl and pyridazinyl. Preferred 5- or 6-membered heteroaryl radicals are furanyl, thienyl, pyrrolyl, thiazolyl, oxazolyl, thiadiazolyl, oxadiazolyl, pyridinyl, pyrimidinyl, pyrazinyl or pyridazinyl. More preferred 5- or 6-membered heteroaryl radicals are 1H-pyrazolyl-4-yl, 1H-pyrazolyl-5-yl and 3-pyridyl.

The NR7R8 group includes, for example, NH2, N(H)CH3, N(CH3)2, N(H)CH2CH3 and N(CH3)CH2CH3.

In the case of —NR7R8, when R7 and R8 together with the nitrogen atom to which they are attached form a 3-6C-heterocyclic ring, the term "3-6C-heterocyclic ring" includes all saturated heterocyclic rings containing 4 to 7 ring atoms and having 1 or 2 nitrogen atoms, or 1 nitrogen atom and 1 oxygen atom. The 3-6C-heterocyclic ring may be optionally substituted one or more times, identically or differently, with a substituent selected from: 1-4C-alkyl, 1-4C-haloalkyl, 1-4C-alkoxy, hydroxy, fluorine, whereby the 1-4C-alkyl may be optionally further substituted with hydroxy. Preferred examples are azetidine, 3-hydroxyazetidine, 3-fluoroazetidine, 3,3-difluoroazetidine, pyrrolidine, 3-hydroxypyrrolidine, piperidine, 3-hydroxypiperidine, 4-hydroxypiperidine, 3-fluoropiperidine, 3,3-difluoropiperidine, 4-fluoropiperidine, 4,4-difluoropiperidine, piperazine, N-methyl-piperazine, N-(2-hydroxyethyl)-piperazine, morpholine.

The C(O)NR7R8 group includes, for example, C(O)NH2, C(O)N(H)CH3, C(O)N(CH3)2, C(O)N(H)CH2CH3, C(O)N(CH3)CH2CH3 or C(O)N(CH2CH3)2. In the case of —NR7R8, when R7 and R8 together with the nitrogen atom to which they are attached form a 3-6C-heterocyclic ring, the term "3-6C-heterocyclic ring" is defined above.

The C(O)O(1-6Calkyl) group includes for example C(O)OCH3, C(O)OC2H5, C(O)C3H7, C(O)CH(CH3)2, C(O)OC4H9, C(O)OC5H11, C(O)OC6H13; for C(O)O(1-6Calkyl) the alkyl part may be straight or branched.

Constituents which are optionally substituted as stated herein, may be substituted, unless otherwise noted, one or more times, independently from one another at any possible position. When any variable occurs more than one time in any constituent, each definition is independent.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)-benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from NH3 or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The term "(chemotherapeutic) anti-cancer agents", includes but is not limited to (i) alkylating/carbamylating agents such as Cyclophosphamid (Endoxan®), Ifosfamid (Holoxan®), Thiotepa (Thiotepa Lederle®), Melphalan (Alkeran@), or chloroethylnitrosourea (BCNU); (ii) platinum derivatives like cis-platin (Platinex® BMS), oxaliplatin (Eloxatin®), satraplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof (like the nanoparticle formulation Abraxane® with paclitaxel bound to albumin), epothilones such as Epothilone B (Patupilone®), Azaepothilone (Ixabepilone®) or Sagopilone; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and (vii) folic acid antagonists such as methotrexate (Farmitrexat®) or premetrexed (Alimta®).

The term "target specific anti-cancer agent", includes but is not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®), OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) histone deacetylase inhibitors like SAHA (Zolinza®), PXD101, MS275, MGCD0103, Depsipeptide/FK228, NVP-LBH589, Valproic acid (VPA), CRA/PCI-24781, ITF2357, SB939 and butyrates (iv) heat shock protein 90 inhibitors like 17-allylaminogeldanamycin (17-AAG) or 17-dimethylaminogeldanamycin (17-DMAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib®) or Vandetanib (Zactima®) or Pazopanib; (vi) monoclonal antibodies such as Trastuzumab (Herceptin®), Rituximab (MabThera/Rituxan®), Alemtuzumab (Campath®), Tositumomab (Bexxar®), C225/Cetuximab (Erbitux®), Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®) or the DNMT1 inhibitor MG98; (viii) Toll-like receptor/TLR 9 agonists like Promune®, TLR 9 agonists like Imiquimod (Aldara®) or Isatoribine and analogues thereof, or TLR 7/8 agonists like Resiquimod as well as immunostimulatory RNA as TLR 7/8 agonists; (ix) protease inhibitors; (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors (e.g. Femara, Arimedex or Aromasin).

Other "target specific anti-cancer agents" include bleomycin, retinoids such as all-trans retinoic acid (ATRA), DNA methyltransferase inhibitors such as 5-Aza-2'-deoxycytidine (Decitabine, Dacogen®) and 5-azacytidine (Vidaza®), alanosine, cytokines such as interleukin-2, interferons such as interferon α2 or interferon-γ, bcl2 antagonists (e.g. ABT-737 or analogs), death receptor agonists, such as TRAIL, DR4/5 agonistic antibodies, FasL and TNF-R agonists (e.g. TRAIL receptor agonists like mapatumumab or lexatumumab).

Specific examples of anti-cancer agents include, but are not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, 1-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

The compounds according to the invention and their salts can exist in the form of tautomers which are included in the embodiments of the invention.

The compounds of the invention may, depending on their structure, exist in different stereoisomeric forms. These forms include configurational isomers or optionally conformational isomers (enantiomers and/or diastereoisomers including those of atropisomers). The present invention therefore includes enantiomers, diastereoisomers as well as mixtures thereof. From those mixtures of enantiomers and/or diaste- Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

The intermediates used for the synthesis of the compounds of claims 1-5 as described below, as well as their use for the synthesis of the compounds of claims 1-5, are one further aspect of the present invention. Preferred intermediates are the Intermediate Examples as disclosed below.

The Compounds According to the Invention can be Prepared as Follows.

The compounds (I) according to the invention can be prepared according to the following schemes,

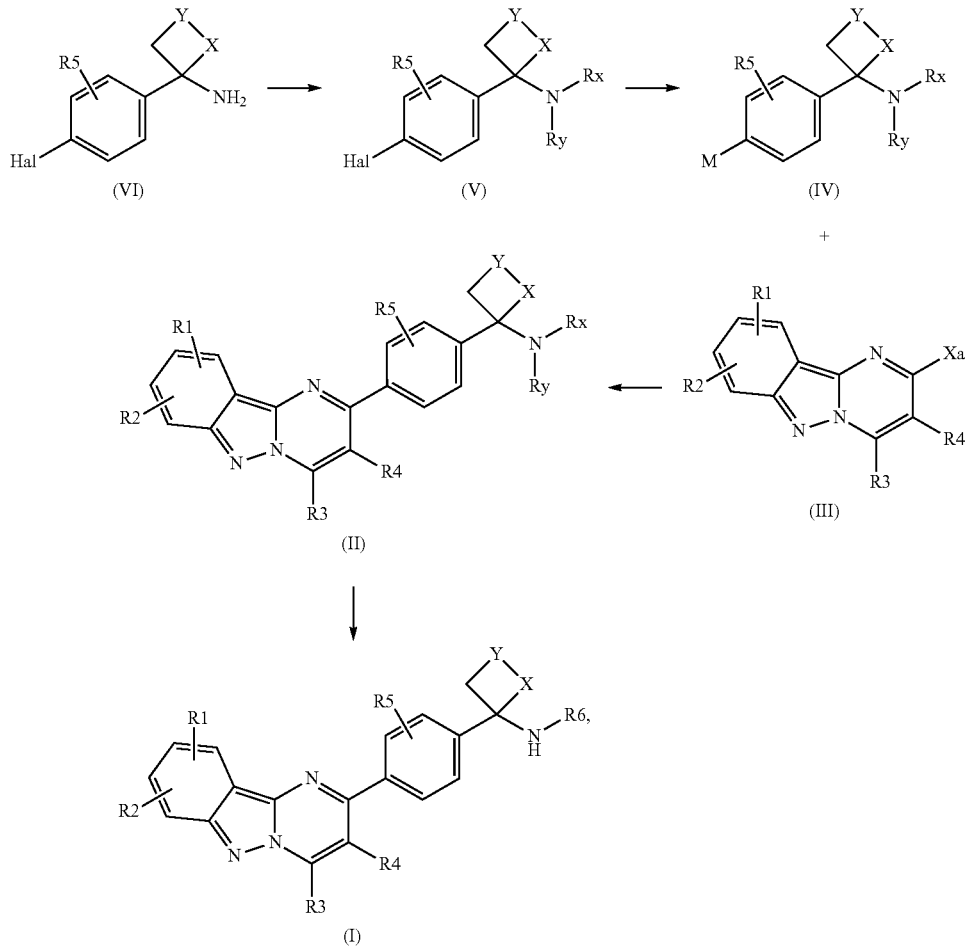

Reaction Scheme 1 reoisomers pure stereoisomeric forms can be isolated with methods known in the art, preferably methods of chromatography, especially high pressure liquid chromatography (HPLC) using achiral or chiral phase. The invention further includes all mixtures of the stereoisomers mentioned above independent of the ratio, including the racemates.

Some of the compounds and salts according to the invention may exist in different crystalline forms (polymorphs) which are within the scope of the invention.

The compounds according to the invention can be prepared according to reaction scheme 1 wherein X, Y, R1, R2, R3, R4, R5 and R6 have the meanings defined in claim 1, Rx has the meaning of R6 and may also be a protecting group; Ry is H, or a protecting group, whereby Rx and Ry together, or Y and Rx together, may form a cyclic protecting group; Hal is a halogen; Xa is a leaving group such as halogen, or a sulfonyl ester, preferably Cl, Br, I, tosylate, trifluoromethansulfonate, nonafluorobutanesulfonate; M is $-B(OH)_2$, $-Sn(1\text{-}4C\text{-alkyl})_3$, $-ZnCl$, $-ZnBr$, $-ZnI$, or,

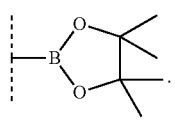

Compounds of general formula (I) may be prepared from compounds of general formula (II). Rx may optionally be R6, or a protecting group, or other such precursor which requires further manipulation. For example, Rx in compounds of general formula (II) may be a protecting group such as the Boc group, —CO(OtBu), or Rx and Ry, together with the nitrogen to which they are attached, form a cyclic protecting group such as a phthalimide. Preparation of compounds of general formula (I) may thus be accomplished by use of an appropriate deprotection reaction, such as in the case of a Boc group, acidic reaction conditions, for example, with a solution of 4M hydrogen chloride in dioxane, in an appropriate solvent, such as for example dichloromethane and methanol, at ambient temperature. Further conditions to deprotect the Boc group, or further protecting groups that may be suitable for use in blocking the amino functionality in compounds of general formula (II), including their synthesis and deprotection, are found, for example, in T. W. Greene, Protective Groups in Organic Synthesis, John Wiley & Sons, 1999, 3rd Ed., or in P. Kocienski, Protecting Groups, Thieme Medical Publishers, 2000. Similarly, when Ry is not H, then Ry is a protecting group, such as for example when Rx and Ry together form a cyclic protecting group such as for example a phthalamide.

Compounds of general formula (II) may be prepared by reacting a compound of general formula (III) with a compound of general formula (IV), for example by a transition metal catalysed C—C bond formation. This transition metal catalysed C—C bond formation reaction can, for example, be achieved if M has the meaning of,

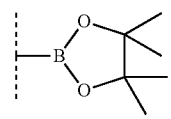

and Xa is Cl, in a suitable solvent such as tetrahydrofuran, N-methyl-2-pyrrolidone, N,N-dimethylformamide, dimethoxyethane, dioxane or mixtures of the above, in the presence of a suitable base, such as aqueous sodium carbonate or potassium carbonate solution, at a suitable temperature, such as from 60° C. to 120° C. and by employing a suitable metal catalyst, such as a palladium catalyst, for example 1,1'-bis(diphenylphosphino)ferrocene]dichloropalladium (II) [Pd(dppf)Cl₂], bis(tri-tert.-butylphosphin)palladium(0) [Pd(PtBu₃)₂], or Pd(PPh₃)₄.

Compounds of general formula (IV) may be prepared from compounds of general formula (V) using known methods, for example, if M has the meaning of

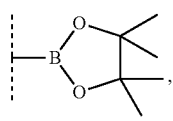

by way of a palladium catalysed borylation reaction, using a suitable metal complex such as a palladium complex formed in situ from a suitable palladium salt and a suitable phosphine ligand, for example, PdCl2(CH₃CN)₂ and SPhos (CAS 657408-07-6), or a preformed palladium complex such as a suitable boron reagent, such as pinacol borane, or bis(pinacolato)diboron (CAS 73183-34-3), a suitable solvent, such as dioxane, dimethylsulfoxide or tetrahydrofuran, and elevated temperatures, such as up to the boiling point of the solvent, preferably 80-120° C. An analogue procedure for the palladium catalysed borylation of aryl halides using pinacol borane is reported by Buchwald et al in J. Org. Chem. 2008, p5589. Alternatively, borylation may be achieved by halogen-metal exchange, followed by quenching of the anion with a suitable borate ester. For example, compounds of general formula (IV) may be reacted with 2 Eq of sec-butyl lithium or n-butyl lithium in a suitable solvent such as tetrahydrofurane, at suitable temperature, such as from −78° C. to −20° C., preferably from −78° C. to −50° C., followed by reaction with methyl pinacol borate or isopropyl pinacol borate. Analogous procedures are known in the literature, such as in EP1870099.

Compounds of general formula (V) and (VI) are either commercially available, may be prepared using the methods described below, may be prepared using known methods, or may be prepared by analogous methods to those known by the person skilled in the art.

One aspect of the invention is the reaction of compounds of general formulae (III) and (IV) to form a compound of general formula (II) as well as deprotection of the compound of general formula (II) to form a compound of general formula (I).

Reaction Scheme 2

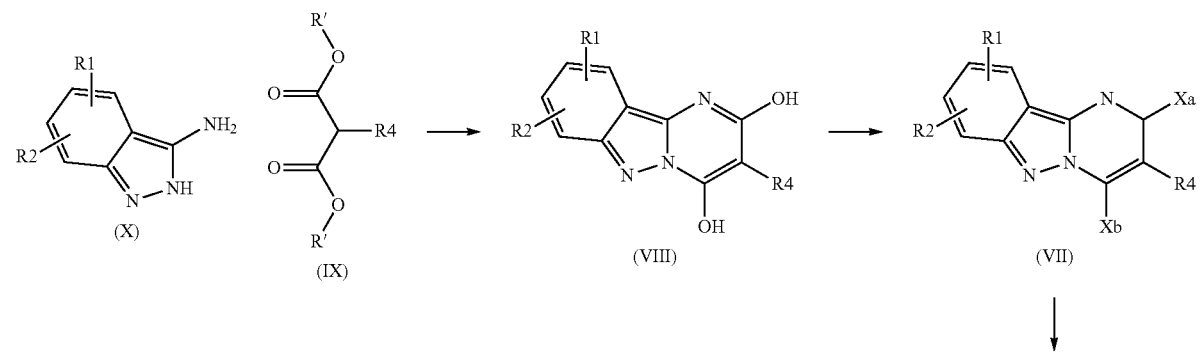

-continued

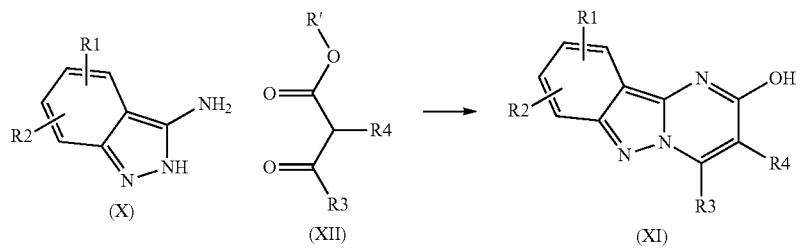

Compounds of general formula (III) may be prepared according to reaction scheme 2 wherein R1, R2, R3 and R4 have the meanings defined above; Xa and Xb are halogen and R' is 1-4C-alkyl.

Compounds of general formula (III) in which R3 is hydrogen, can be obtained from a compound of general formula (VII). This reaction can for example be achieved by reaction with a suitable reducing agent, such as zinc or zinc/copper pair in a suitable solvent such as mixture of tetrahydrofuran, methanol and water at suitable temperature, such as from 0° C. to 80° C., preferable ambient temperature. Alternatively this reaction can for example be achieved by reaction with zinc in a mixture of ammonia solution, dichloromethane and brine at suitable temperatures such as from 0° C. to 80° C., preferably from 0° C. to ambient temperature.

Alternatively, compounds of formula (III), wherein R3 is NR15R16, can be obtained by reaction of a corresponding compound of formula (VII) with the respective corresponding amino compound, HNR15R16, for example $NH_2CH_3$, in a suitable solvent such as tetrahydrofuran, N-methyl-pyrrolidone or N,N-dimethylformamide, at a suitable temperature, such as 50° C. to the boiling point of the solvent.

Alternatively, compounds of general formula (III) in which R3 has the meaning of 1-4C-alkyl or 3-7-cycloalkyl, can for example be prepared from corresponding compounds of formula (XI) by treatment with a suitable halogenation reagent, such as phosphorus oxychloride in the case that Xa has the meaning of Cl, or phosphorus tribromide or phosphorus oxybromide in the case that Xa has the meaning of Br.

Compounds of general formula (VII) can be synthesized from corresponding compounds of formula (VIII) with a suitable halogenation reagent, for example, phosphorus oxychloride, phosphorus tribromide, phosphorus oxybromide.

Compounds of general formula (VIII), can be prepared with a condensation of the corresponding amino heterocycle of formula (X) and the malonate esters of formula (IX). This reaction can, for example, be accomplished in N,N-dimethylformamide at elevated temperatures of from 80 to 200° C. and by employing a base such as diaza(1,3)bicyclo[5.4.0]undecane (DBU) or tributylamine.

Compounds of general formula (XI), wherein R3 is 1-4C-alkyl or 3-7-cycloalkyl can be prepared, for example, with a condensation of the corresponding amino heterocycle of formula (X) and the beta ketoesters of formula (XII). This reaction can, for example, be accomplished in N,N-dimethylformamide at elevated temperatures of from 80 to 200° C. and by employing a base such as DBU or tributylamine.

Compounds of formulae (IX), (X), or (XII) are either commercially available, may be prepared using the methods described below, may be prepared using known methods, or may be prepared by analogous methods to those known by the person skilled in the art.

Thus one aspect of the invention is the process for the manufacture of compounds of general formula (I), characterized in that a compound of formula (III)

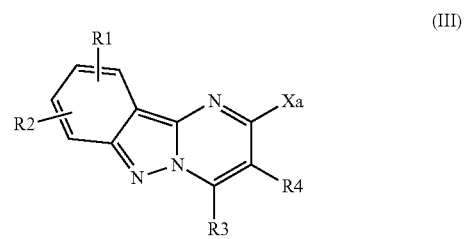

wherein R1, R2, R3 and R4 have the meaning as defined in claim 1 and Xa is a leaving group, is reacted with a compound of general formula (IV)

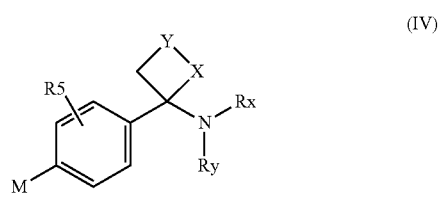

wherein R5, X and Y have the meaning as defined in claim 1, M is —B(OH)$_2$, —Sn(1-4C-alkyl)$_3$, —ZnCl, —ZnBr, —ZnI, or,

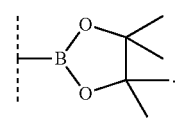

Rx is R6 or a protecting group
Ry is hydrogen or a protecting group or Rx and Ry together form a cyclic protecting group, forming a compound of general formula (II)

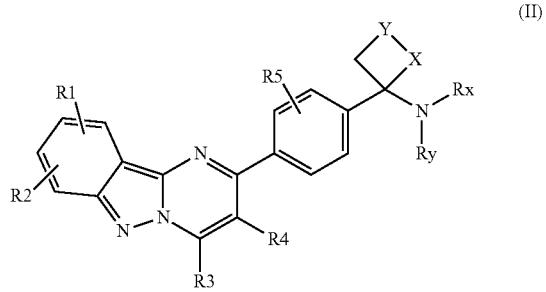

which is subsequently optionally deprotected to form a compound of general formula (I)

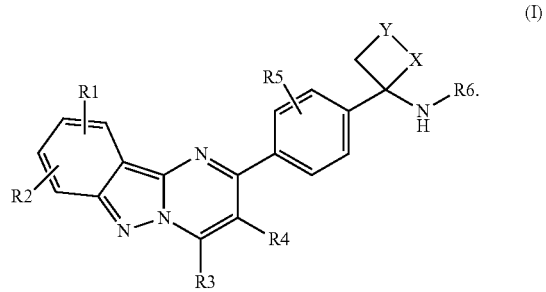

One preferred aspect of the invention is the process for the preparation of the compounds of claims 1-5 according to the Examples as well as the Intermediates as disclosed in the experimental section, especially the intermediates 2-0, 2-1, 2-2.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as meta-chloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

Commercial Utility

The compounds of formula (I) and the stereoisomers of the compounds of formula (I) according to the invention are hereinafter referred to as the compounds of the invention. In particular, the compounds of the invention are pharmaceutically acceptable. The compounds according to the invention have valuable pharmaceutical properties, which make them commercially utilizable. In particular, they inhibit the Pi3K/Akt pathway and exhibit cellular activity. They are expected to be commercially applicable in the therapy of diseases (e.g. diseases dependent on overactivated Pi3K/Akt). An abnormal activation of the PI3K/AKT pathway is an essential step towards the initiation and maintenance of human tumors and thus its inhibition, for example with AKT inhibitors, is understood to be a valid approach for treatment of human tumors. For a recent review see Garcia-Echeverria et al (Oncogene, 2008, 27, 551-5526).

Cellular activity and analogous terms in the present invention is used as known to persons skilled in the art, as an example, inhibition of phosphorylation, inhibition of cellular proliferation, induction of apoptosis or chemosensitization.

Chemosensitization and analogous terms in the present invention is used as known to persons skilled in the art. These stimuli include, for example, effectors of death receptor and survival pathways as well as cytotoxic/chemotherapeutic and targeted agents and finally radiation therapy. Induction of apoptosis and analogous terms according to the present invention are used to identify a compound which excecutes programmed cell death in cells contacted with that compound or in combination with other compounds routinely used for therapy.

Apoptosis in the present invention is used as known to persons skilled in the art. Induction of apoptosis in cells contacted with the compound of this invention might not necessarily be coupled with inhibition of cell proliferation. Preferably, the inhibition of proliferation and/or induction of apoptosis are specific to cells with aberrant cell growth.

Furthermore, the compounds according to the present invention inhibit protein kinase activity in cells and tissues, causing a shift towards dephosphorylated substrate proteins and as functional consequence, for example the induction of apoptosis, cell cycle arrest and/or sensitization towards chemotherapeutic and target-specific cancer drugs. In a preferred embodiment, inhibition of the Pi3K/Akt pathway induces cellular effects as mentioned herein, alone, or in combination with standard cytotoxic or targeted cancer drugs.

Compounds according to the present invention exhibit anti-proliferative and/or pro-apoptotic and/or chemosensitizing properties. Accordingly, the compounds of the present invention are useful for the treatment of hyperproliferative disorders, in particular cancer. Therefore the compounds of the present invention are useful to induce an anti-proliferative and/or pro-apoptotic and/or chemosensitizing effect in mammals, such as humans, suffering from a hyperproliferative disorders, like cancer.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, especially malignant neoplasia, including cancer and the tumor types as disclosed below.

Compounds according to the present invention exhibit anti-proliferative and/or pro-apoptotic properties in mammals such as humans due to inhibition of metabolic activity of cancer cells which are able to survive despite of unfavourable growth conditions such as glucose depletion, hypoxia or other chemo stress.

Thus, the compounds according to the present invention are useful for treating, ameliorating or preventing diseases of benign or malignant behaviour as described herein, such as e.g. for inhibiting cellular neoplasia.

Neoplasia in the present invention is used as known to persons skilled in the art. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

It is noted that a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function and death.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of the Pi3K/Akt pathway leads to a resensitization towards standard chemotherapeutic or target specific cancer therapeutics. As a consequence, the commercial applicability of the compounds according to the present invention is not limited to $1^{st}$ line treatment of cancer patients. In a preferred embodiment, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

Compounds according to the present invention are suitable for treatment, prevention or amelioration of the diseases of benign and malignant behavior as described above, such as e.g. benign or malignant neoplasia, particularly cancer, especially a cancer that is sensitive to Pi3K/Akt pathway inhibition.

The present invention further includes a method for treating, preventing or ameliorating mammals, including humans, preferably treating mammals, including humans, which are suffering from one of the abovementioned conditions, illnesses, disorders or diseases. The method is characterized in that a pharmacologically active and therapeutically effective and tolerable amount of one or more of the compounds according to the present invention is administered to the subject in need of such treatment.

The present invention further includes a method for treating, preventing or ameliorating diseases responsive to inhibition of the Pi3K/Akt pathway, in a mammal, including human, preferably treating diseases responsive to inhibition of the Pi3K/Akt pathway, in a mammal, including human, comprising administering a pharmacologically active and therapeutically effective and tolerable amount of one or more of the compounds according to the present invention to said mammal.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for treating hyperproliferative diseases of benign or malignant behaviour and/or disorders responsive to induction of apoptosis, such as e.g. cancer, particularly any of those cancer diseases described above, in a mammal, comprising administering a pharmacologically active and therapeutically effective and tolerable amount of one or more of the compounds according to the present invention to said mammal.

The present invention further includes a method for inhibiting cellular hyperproliferation or arresting aberrant cell growth in a mammal, comprising administering a pharmacologically active and therapeutically effective and tolerable amount of one or more of the compounds according to the present invention to said mammal.

The present invention further includes a method for inducing apoptosis in the therapy of benign or malignant neoplasia, particularly cancer, comprising administering a pharmacologically active and therapeutically effective and tolerable amount of one or more of the compounds according to the present invention to a subject in need of such therapy.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for sensitizing towards chemotherapeutic or target-specific anti-cancer agents in a mammal, comprising administering a pharmacologically active and therapeutically effective and tolerable amount of one or more of the compounds according to the present invention to said mammal.

The present invention further includes a method for treating benign and/or malignant neoplasia, especially malignant neoplasia, particularly cancer, in a mammal, including human, comprising administering a pharmacologically active and therapeutically effective and tolerable amount of one or more of the compounds according to the present invention to said mammal.

The present invention further includes a method for treating solid and hematological tumors, whereby solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). and hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

The present invention further relates to the use of the compounds for the production of pharmaceutical compositions, which are employed for the treatment, prophylaxis, and/or amelioration of one or more of the illnesses mentioned, preferably for the treatment of one or more of the illnesses mentioned.

The present invention further relates to the use of the compounds for the manufacture of pharmaceutical compositions for treating, preventing or ameliorating, preferably treating hyperproliferative diseases and/or disorders responsive to the induction of apoptosis, such as e.g. benign or malignant neoplasia, especially malignant neoplasia, in particular cancer, especially those cancer diseases and tumor types mentioned above.

The present invention further relates to the use of the compounds according to this invention for the production of pharmaceutical compositions for treating, preventing or ameliorating, preferably treating benign or malignant neoplasia, especially malignant neoplasia, particularly cancer, such as e.g. any of those cancer diseases and tumor types described above.

The invention further relates to a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The invention further related to the use of a compound according to the invention or a pharmaceutically acceptable salt thereof, for the production of a pharmaceutical composition for the treatment, prevention or amelioration of a disease mediated by a dysregulated function of a single protein kinase or multiple protein kinases and/or disorders responsive to the induction of apoptosis.

The invention further relates to a pharmaceutical composition, comprising a compound according to the invention or a pharmaceutically acceptable salt thereof, for the treatment and/or prophylaxis, preferably treatment of (hyper)proliferative diseases and/or disorders responsive to induction of apoptosis, which include benign neoplasia and malignant neoplasia, including cancer.

The present invention further relates to the use of compounds and pharmaceutically acceptable salts according to the present invention for the manufacture of pharmaceutical compositions, which can be used for sensitizing towards chemotherapeutic and/or target specific anti-cancer agents.

The present invention further relates to the use of compounds according to the present invention for the manufacture of pharmaceutical compositions, which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, dermatoses, and myelodysplastic syndromes.

The present invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine or beta-cyclodextrin derivative inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous deliveries are preferred.

Generally, the pharmaceutical compositions according to the invention can be administered such that the dose of the active compound is in the range customary for Pi3K/Akt pathway inhibitors. In particular, a dose in the range of from 0.01 to 4000 mg of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1500 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The present invention further relates to combinations comprising one or more first active ingredients selected from the compounds of the invention and one or more second active ingredients selected from chemotherapeutic anti-cancer agents and target-specific anti-cancer agents e.g. for treating, preventing or ameliorating diseases responsive or sensitive to inhibition of the Pi3K/Akt pathway, such as hyperproliferative diseases of benign or malignant behaviour and/or disorders responsive to the induction of apoptosis, particularly cancer, such as e.g. any of those cancer diseases described above.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware of the total daily dosage(s) and administration form(s) of the additional therapeutic agent(s) coadministered. Said total daily dosage(s) can vary within a wide range depending from the agent combined.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising
a.) at least one compound according to this invention formulated with a pharmaceutically acceptable carrier or diluent, and
b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat hyperproliferative diseases and diseases responsive or sensitive to inhibition of the Pi3K/Akt pathway, such as e.g. benign or malignant neoplasia, particularly cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Pi3K/Akt pathway inhibitory activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating, especially treating hyperproliferative diseases and/or disorders responsive to induction of apoptosis, such as e.g. benign or malignant neoplasia, especially malignant neoplasia, e.g. cancer, particularly any of those cancer diseases and tumor types mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating, especially treating hyperproliferative diseases, and/or disorders responsive to the induction of apoptosis, such as e.g. malignant or benign neoplasia, especially malignant neoplasia, such as e.g. cancer, particularly those diseases and tumor types mentioned herein.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be according, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a hyperproliferative diseases and/or a disorder responsive to the induction of apoptosis, particularly one of those diseases mentioned herein, such as e.g. malignant or benign neoplasia, especially malignant neoplasia, e.g. cancer, like any of those cancer diseases and tumor types mentioned herein.

In addition, compounds according to the present invention can be used in the pre- or post-surgical treatment of cancer.

In further addition, compounds of the present invention can be used in combination with radiation therapy.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL PART

The following table lists the abbreviations used in this paragraph and in the Intermediate Examples and Examples section as far as they are not explained within the text body. NMR peak forms are stated as they appear in the spectra, possible higher order effects have not been considered. Chemical names were generated using AutoNom2000 as implemented in MDL ISIS Draw. In some cases generally accepted names of commercially available reagents were used in place of AutoNom2000 generated names.

| Abbreviation | Meaning |
|---|---|
| Boc | tert-Butoxycarbonyl |
| br | broad |
| CI | chemical ionisation |
| d | doublet |
| dd | doublet of doublet |
| DAD | diode array detector |
| DBU | 1,5-diazabicyclo(5.4.0)undec-5-ene |
| DCM | dichloromethane |
| DIP | diisopropylether |
| DMA | N,N-dimethylacetamide |
| DMF | N,N-dimethylformamide |
| EtOAc | ethyl acetate |
| Eq. | equivalent |
| ESI | electrospray (ES) ionisation |
| HPLC | high performance liquid chromatography |
| LC-MS | liquid chromatography mass spectrometry |
| m | multiplet |
| Mesyl | methanesulfonyl |
| MS | mass spectrometry |
| n-BuLi | n-Butyllithium |
| NMP | N-methyl-2-pyrrolidone |

-continued

| Abbreviation | Meaning |
|---|---|
| NMR | nuclear magnetic resonance spectroscopy: chemical shifts ($\delta$) are given in ppm. |
| ONf | nonafluorobutanesulfonate |
| OTf | trifluoromethanesulfonate |
| OTs | tosylate |
| Pd(dppf)Cl$_2$ | 1,1' bis(diphenylphosphino)ferrocene]dichloropalladium(II) |
| Pd(PtBu$_3$)$_2$ | bis (tri-tert-butylphosphine)palladium(0) [Pd(PtBu$_3$)$_2$], |
| q | quartet |
| r.t. or rt | room temperature |
| RT | retention time (as measured either with HPLC or UPLC) in minutes |
| s | singlet |
| t | triplet |
| THF | tetrahydrofuran |
| UPLC | ultra performance liquid chromatography |

Other abbreviations have their meanings customary per se to the skilled person. The various aspects of the invention described in this application are illustrated by the following examples which are not meant to limit the invention in any way.

EXAMPLES

UPLC-MS Standard Procedure

Analytical UPLC-MS was performed as described below. The masses (m/z) are reported from the positive mode electrospray ionisation unless the negative mode is indicated (ES−). In most of the cases method A is used. If not, it is indicated.

UPLC-MS Method A

Instrument: Waters Acquity UPLC-MS SQD 3001; Column: Acquity UPLC BEH C18 1.7 50×2.1 mm; Eluent A: water+0.1% formic acid, Eluent B: acetonitrile; Gradient: 0-1.6 min 1-99% B, 1.6-2.0 min 99% B; Flow rate 0.8 ml/min; Temperature: 60° C.; Injection: 2 µl; DAD scan: 210-400 nm.

UPLC-MS Method B

Instrument: Waters Acquity UPLC-MS SQD 3001; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 ml/min; Temperature: 60° C.; Injection: 2 µl; DAD scan: 210-400 nm; ELSD.

UPLC-MS Method C

Instrument: Waters Acquity UPLC-MS ZQ4000; Column: Acquity UPLC BEH C18 1.7 50×2.1 mm; Eluent A: water+0.05% formic acid, Eluent B: acetonitrile+0.05% formic acid; Gradient: 0-1.6 min 1-99% B, 1.6-2.0 min 99% B; Flow rate 0.8 ml/min; Temperature: 60° C.; Injection: 2 µl; DAD scan: 210-400 nm.

UPLC-MS Method D

Instrument: Waters Acquity UPLC-MS ZQ4000; Column: Acquity UPLC BEH C18 1.7 50×2.1 mm; Eluent A: water+0.2% ammonia, Eluent B: acetonitrile; Gradient: 0-1.6 min 1-99% B, 1.6-2.0 min 99% B; Flow rate 0.8 ml/min; Temperature: 60° C.; Injection: 2 µl; DAD scan: 210-400 nm; ELSD.

Intermediate Example Int-1-0

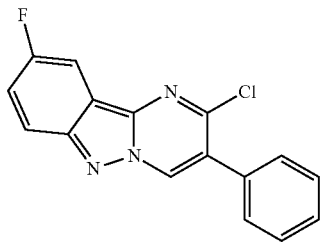 [SMILES: Fc1ccc2nn3cc(-c4ccccc4)c(Cl)nc3c2c1]

2-Chloro-9-fluoro-3-phenylpyrimido[1,2-b]indazole

Step 1:
9-Fluoro-3-phenylpyrimido[1,2-b]indazole-2,4-diol 14.3 g (60.2 mmol) Diethyl phenylmalonate, 9.1 g (60.2 mol) 5-fluoro-1H-indazol-3-ylamine and 25.3 mL tributyl amine were heated for 15 h at 180° C. The reaction mixture was treated with 2M sodium hydroxide and water and extracted with tert-butyl methyl ether. The organic phase was discarded and the aqueous phase was acidified with conc. hydrochloric acid. The precipitate was collected by filtration and washed with water to obtain 14 g of the desired product which is 90% pure. MS (Cl, M+1): 296

$^1$H-NMR (400 MHz, dDMSO): δ 7.69-7.79 (m, 1H), 7.50-7.68 (m, 4H), 7.26-7.39 (m, 2H), 7.13-7.22 (m, 1H).

Step 2: 2,4-Dichloro-9-fluoro-3-phenylpyrimido[1,2-b]indazole 14 g (47.4 mmol) 9-Fluoro-3-phenylpyrimido[1,2-b]indazole-2,4-diol, 26.5 ml (284 mmol) phosphorus oxychloride and 8.9 ml (70.5 mmol) N,N-dimethylaniline were heated for 6 h at 100° C. The reaction mixture was poured on ice water (slowly and cautiously: strong development of heat) and stirred vigorously for one hour. The precipitate was filtered off and dried yielding 14.3 g (91%) of the title compound which was however contaminated.

MS (ES+, M+1): 332
$^1$H-NMR (400 MHz, dDMSO): δ 7.95-8.08 (m, 2H), 7.48-7.68 (m, 6H).

Step 3:
2-Chloro-9-fluoro-3-phenylpyrimido[1,2-b]indazole 7.2 g (21.7 mmol) 2,4-Dichloro-9-fluoro-3-phenylpyrimido[1,2-b]indazole were suspended in a mixture of 551 mL ethanol, 392 mL water and 211 mL tetrahydrofuran. After addition of 5.5 g (102.7 mmol) ammonium chloride and 9.1 g (138.7 mmol) zinc the mixture was stirred over night at room temperature. The mixture was filtered via a glass fibre filter, and the organic solvents were removed. The product which precipitated was filtered off (3.4 g=51.9%). 3.4 g (42.2%) of the starting material wereregained by stirring the zinc slurry with 1 L ethyl acetate, filtration of the zinc via a glass fibre filter and evaporation of the organic solvent. The product was contaminated with 9-fluoro-3-phenylpyrimido[1,2-b]indazole (25%).

UPLC-MS: RT=1.42 min; m/z=298 (ES+, M+1)
$^1$H-NMR (300 MHz, dDMSO): δ 9.55 (s, 1H), 7.82-8.01 (m, 3H), 7.42-7.62 (m, 5H).

Intermediate Example Int-1-1

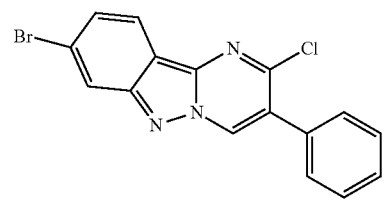 [SMILES: Clc1nc2c3ccc(Br)cc3nn2cc1-c1ccccc1]

8-Bromo-2-chloro-3-phenylpyrimido[1,2-b]indazole

Step 1:
8-Bromo-3-phenylpyrimido[1,2-b]indazole-2,4-diol 9.9 g (46.7 mmol) 6-Bromo-1H-indazol-3-ylamine, 11 g (46.7 mmol) diethyl phenylmalonate and 19.8 mL (83.1 mmol) tributyl amine were heated for 15 h at 180° C. The reaction mixture was treated with 2M sodium hydroxide and water and extracted three times with tert-butyl methyl ether. The organic phase was discarded and the aqueous phase was acidified with conc. hydrochloric acid. The precipitate was collected by filtration and washed with water to obtain the desired product (16.2 g) which was however contaminated and which was used in the next step without further purification.

MS (ES+, M+1): 356/358 (Br isotopes)

Step 2: 8-Bromo-2,4-dichloro-3-phenylpyrimido[1,2-b]indazole 11.2 g (31.4 mmol) 8-Bromo-3-phenylpyrimido[1,2-b]indazole-2,4-diol, 17.6 mL (188.5 mmol) phosphorus oxychloride and 5.9 mL (46.8 mmol) N,N-dimethylaniline were heated for two days at 100° C. The reaction mixture was poured on ice water (slowly and cautiously: strong development of heat) and stirred vigorously for one hour. The precipitate was filtered off and dried yielding 12.2 g of the title compound which was however contaminated and which was used in the next step without further purification.

MS (ES+, M+1): 392/394/396 (Br and Cl isotopes)

Step 3:
8-Bromo-2-chloro-3-phenylpyrimido[1,2-b]indazole 7 g (17.8 mmol) 8-Bromo-2,4-dichloro-3-phenylpyrimido[1,2-b]indazole were suspended in a mixture of 453 mL ethanol, 322 mL water and 173 mL tetrahydrofuran. After addition of 4.5 g (84.4 mmol) ammonium chloride and 7.5 g (114 mmol) zinc the mixture was stirred over night at room temperature. The mixture was filtered via a glass fibre filter, washed with THF and the organic solvents were removed. The residue was treated with a mixture of water and ethyl acetate and the organic phase was separated. The aqueous phase was extracted twice with ethyl acetate and the combined organic extracts were evaporated without prior drying because the product had already precipitated. 3.7 g (57.9%) of the title compound were isolated.

UPLC-MS: RT=1.55 min; m/z=358/360 (ES+, M+1)
$^1$H-NMR (300 MHz, dDMSO): δ 9.59 (s, 1H), 8.19 (d, 1H), 8.10 (d, 1H), 7.45-7.69 (m, 5H), 7.41 (d, 1H).

The following intermediate examples have been prepared in analogy to intermediate example Int-1-1 by reacting the corresponding bromo-1H-indazole-3-ylamines with diethyl phenylmalonate, followed by reaction with phosphorus oxychloride and reduction with zinc.

| Intermediate example | Structure/Name | 1H-NMR | UPLC-MS |
|---|---|---|---|
| Int-1-2 | 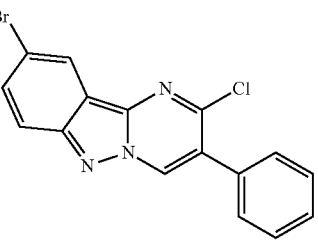<br>9-Bromo-2-chloro-3-phenyl-pyrimido[1,2-b]indazole | $^1$H-NMR (400 MHz, dDMSO): δ 9.69 (s, 1H), 8.42 (d, 1H), 7.82 (d, 1H), 7.72 (d, 1H), 7.59-7.68 (m, 2H), 7.48-7.59 (m, 3H). | RT = 1.54 min; m/z = 358/ 360 (ES+, M + 1) |
| Int-1-3 | 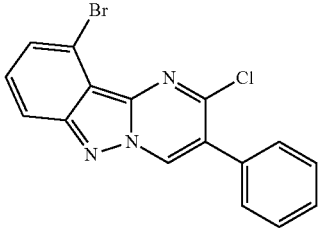<br>10-Bromo-2-chloro-3-phenyl-pyrimido[1,2-b]indazole | $^1$H-NMR (300 MHz, dDMSO): δ 9.61 (s, 1H), 7.79-7.89 (m, 1H), 7.59-7.69 (m, 2H), 7.45-7.59 (m, 5H). | RT = 1.49 min; m/z = 358/ 360 (ES+, M+1) |
| Int-1-4 | 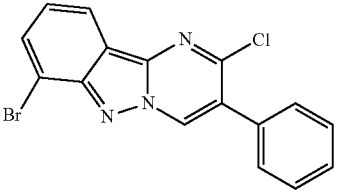<br>7-Bromo-2-chloro-3-phenyl-pyrimido[1,2-b]indazole | $^1$H-NMR (300 MHz, dDMSO): δ 9.71 (s, 1H), 8.25 (d, 1H), 7.95 (d, 1H), 7.58-7.69 (m, 2H), 7.45-7.58 (m, 3H), 7.22 (dd, 1H). | RT = 1.48 min; m/z = 358/360 (ES+, M + 1) |

Intermediate Example Int-2-0

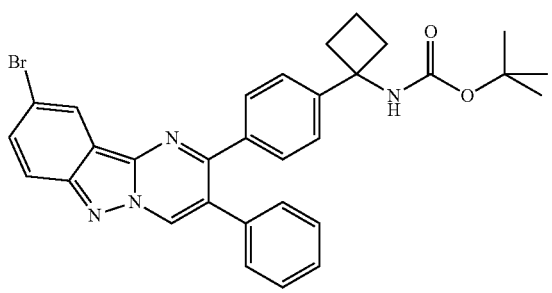 [SMILES: CC(C)(C)OC(=O)NC1(c2ccc(-c3nc4c5cc(Br)ccc5nn4cc3-c3ccccc3)cc2)CCC1]

{1-[4-(9-Bromo-3-phenylpyrimido[1,2-b]indazol-2-yl)phenyl]cyclobutyl}-carbamic acid tert-butyl ester 1 g (2.9 mmol) 9-Bromo-2-chloro-3-phenylpyrimido[1,2-b]indazole (intermediate example Int-1-2), 1.09 g (2.9 mmol) {1-[4-(4,4,5,5-tetramethyl-1,3,2- dioxaborolan-2-yl)phenyl] cyclobutyl}carbamic acid tert-butyl ester, 322 mg (0.28 mmol) tetrakis(triphenylphosphine)palladium and 886 mg (8.4 mmol) sodium carbonate in 30 mL dioxane and 4.2 mL water were heated over night at 105° C. The reaction mixture was poured on water/dichloromethane and vigorously stirred for 30'. The organic phase was separated, washed with brine, dried, filtered, and the solvent was evaporated. The residue was purified by HPLC yielding 346.4 mg (20.6%) of the title compound.

MS (ES+, M+1): 569/571 (Br isotopes)

(400 MHz, dDMSO): δ □ 9.43 (s, 1H), 8.42 (s, 1H), 7.80 (d, 1H), 7.72 (d, 1H), 7.59 (br., 1H), 7.22-7.48 (m, 9H), 2.19-2.43 (m, 4H), 1.84-2.05 (m, 1H), 1.63-1.84 (m, 1H), 0.95-1.48 (m, 9H).

The following intermediate examples have been prepared in analogy to intermediate example Int-2-0 by reacting the corresponding bromo-2-chloro-3-phenylpyrimido[1,2-b]indazoles with {1-[4-(4,4,5,5-tetramethyl-1,3,2-dioxaborolan-2-yl)phenyl]cyclobutyl}carbamic acid tert-butyl ester and subsequent purification by HPLC.

| Intermediate example | Structure/Name | 1H-NMR | UPLC-MS |
|---|---|---|---|
| Int-2-1 | 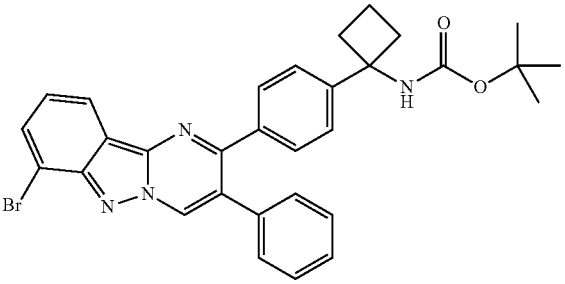<br>{1-[4-(7-Bromo-3-phenylpyrimido[1,2-b]indazol-2-yl)phenyl]cyclobutyl}-carbamic acid tert-butyl ester | (400 MHz, dDMSO): δ 9.59 (s, 1H), 8.30 (d, 1H), 7.92 (d, 1H), 7.60 (br., 1H), 7.25-7.48 (m, 9H), 7.21 (dd, 1H), 2.21-2.44 (m, 4H), 1.87-2.04 (m, 1H), 1.63-1.87 (m, 1H), 0.98-1.42 (m, 9H). | RT = 1.69 min; m/z = 569/571 (ES+, M + 1) |
| Int-2-2 | 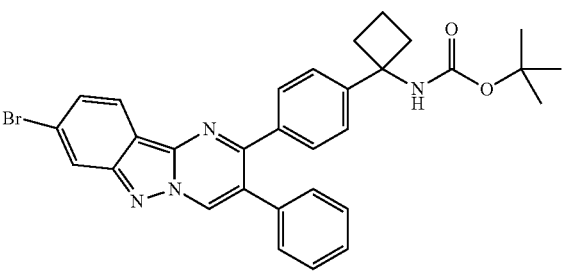<br>{1-[4-(8-Bromo-3-phenylpyrimido[1,2-b]indazol-2-yl)phenyl]cyclobutyl}-carbamic acid tert-butyl ester | (300 MHz, dDMSO): δ 9.48 (s, 1H), 8.21 (d, 1H), 8.08 (d, 1H), 7.60 (br., 1H), 7.21-7.45 (m, 10H), 2.20-2.43 (m, 4H), 1.84-2.05 (m, 1H), 1.63-1.84 (m, 1H), 0.96-1.42 (m, 9H). | RT = 1.73 min; m/z = 569/571 (ES+, M + 1) |

Intermediate Example Int-3-0

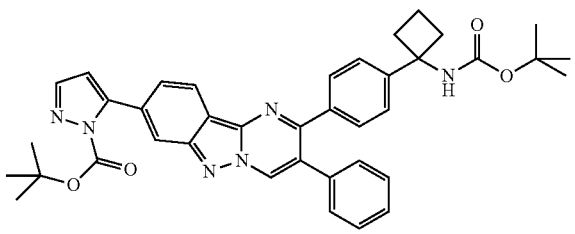 [SMILES: CC(C)(C)OC(=O)NC1(c2ccc(-c3nc4c5ccc(-c6ccnn6C(=O)OC(C)(C)C)cc5nn4cc3-c3ccccc3)cc2)CCC1]

5-[2-(4-{1-[(tert-Butoxycarbonyl)amino]cyclobutyl}phenyl)-3-phenylpyrimido[1,2-b]indazol-8-yl]-1H-pyrazole-1-carboxylic acid tert-butyl ester 100 mg (0.18 mmol) {1-[4-(8-Bromo-3-phenylpyrimido[1,2-b]indazol-2-yl)phenyl]-cyclobutyl}carbamic acid tert-butyl ester, intermediate example Int-2-2, 74.5 mg (0.35 mmol) [1-(tert-butoxycarbonyl)-1H-pyrazol-5-yl]boronic acid, 14.3 mg (0.02 mmol) 1,1 bis(diphenylphosphino)ferrocenedichloro-palladium(II) and 55.8 mg (0.53 mmol) sodium carbonate in 1.8 mL dioxane and 0.3 mL water (both solvents had been degassed) were heated in the microwave for 30' at 105° C. The reaction mixture was poured on water/dichloromethane/saturated ammonium chloride and vigorously stirred for 30'. The organic phase was separated, washed twice with brine, dried (sodium sulfate) and filtrated. The solvent was evaporated and the crude residue (181 mg>100%) was used in the next step without further purification.

UPLC-MS: RT=1.67 min; m/z=557 (ES+, M+1-Boc residue)

The following intermediate examples had been prepared in analogy according to intermediate example Int-3-0 by reacting the corresponding bromo compounds with the appropriate boronic acids.

| Intermediate example | Structure/Name | 1H-NMR | UPLC-MS resp. MS |
|---|---|---|---|
| Int-3-1 | 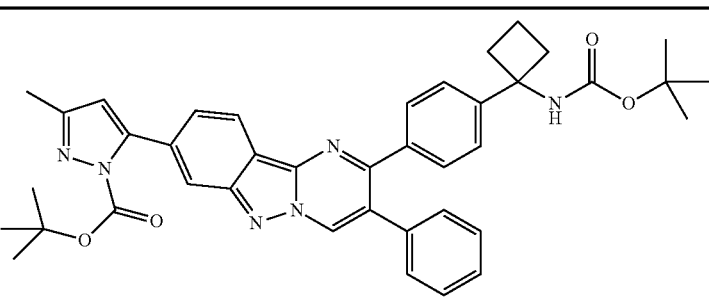<br>5-[2-(4-{1-[(tert-Butoxycarbonyl)amino]cyclobutyl}-phenyl)-3-phenylpyrimido[1,2-b]indazol-8-yl]-3-methyl-1H-pyrazole-1-carboxylic acid tert-butyl ester | | RT = 1.77 min; m/z = 671 (ES+, M + 1) |
| Int-3-2 | 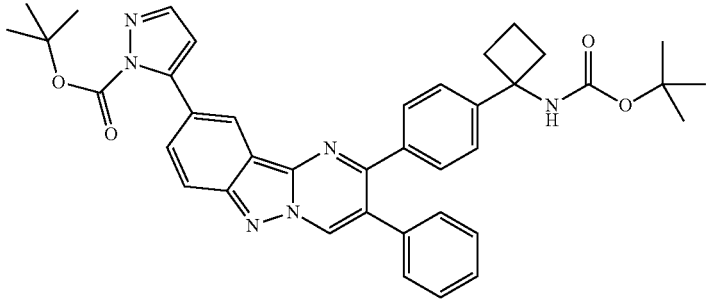<br>5-[2-(4-{1-[(tert-Butoxycarbonyl)amino]cyclobutyl}-phenyl)-3-phenylpyrimido[1,2-b]indazol-9-yl]-1H-pyrazole-1-carboxylic acid tert-butyl ester | | RT = 1.69 min; m/z = 657 (ES+, M + 1) |
| Int-3-3 | 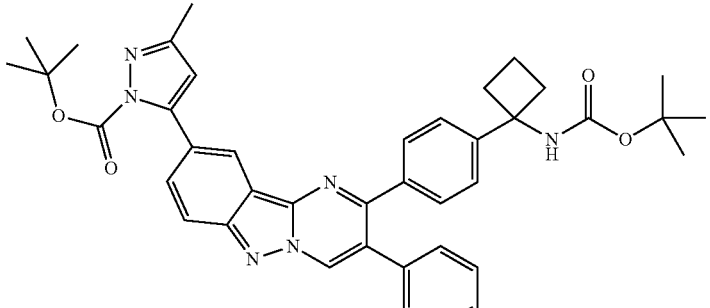<br>5-[2-(4-{1-[(tert-Butoxycarbonyl)amino]cyclobutyl}-phenyl)-3-phenylpyrimido[1,2-b]indazol-9-yl]-3-methyl-1H-pyrazole-1-carboxylic acid tert-butyl ester | | RT = 1.64 min; m/z = 671 (ES+, M + 1) |

Intermediate Example Int-4-0

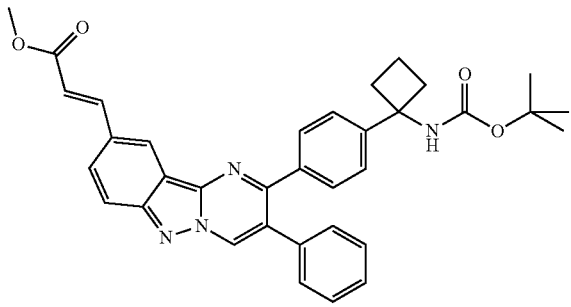 [SMILES: COC(=O)/C=C/c1ccc2nn3cc(-c4ccccc4)c(-c4ccc(C5(NC(=O)OC(C)(C)C)CCC5)cc4)nc3c2c1]

(E)-3-[2-(4-{1-[(tert-Butoxycarbonyl)amino]cyclobutyl}phenyl)-3-phenylpyrimido[1,2-b]indazol-9-yl]acrylic acid methyl ester 150 mg (0.26 mmol) {1-[4-(9-Bromo-3-phenylpyrimido[1,2-b]indazol-2-yl)phenyl]-cyclobutyl}carbamic acid tert-butyl ester, intermediate example Int-2-0, 43.4 mg (0.53 mmol) acrylic acid methyl ester, 13.63 mg (0.045 mmol) tri-2-tolylphosphane, 5.9 mg (0.026 mmol) palladium(II) acetate and 0.04 mL (0.3 mmol) triethylamine in 1.9 mL degassed acetonitrile were heated in the microwave at 110° C. for 60'. The reaction mixture was poured on water/saturated ammonium chloride/dichloromethane and vigorously stirred for 30 minutes. The organic phase was separated, washed with brine and dried. After removal of the solvent the crude product (186.8 mg>100%) was used in the next step without further purification.

UPLC-MS: RT=1.76 min; m/z=575 (ES+, M+1)

The following intermediate example had been prepared in analogy according to intermediate example Int-4-0 by reacting the corresponding bromo compound with the acrylamide.

mL 4M hydrogen chloride in dioxane the reaction mixture was stirred for five hours at room temperature. The reaction mixture was evaporated to dryness and the residue was treated with saturated aqueous sodium bicarbonate solution. After extraction with ethyl acetate (three times) the combined organic phases were washed with brine, dried over sodium sulfate and the solvent was removed.

| Intermediate example | Structure/Name | 1H-NMR | UPLC-MS resp. MS |
|---|---|---|---|
| Int-4-1 | (1-{4-[9-((E)-2-Carbamoylvinyl)-3-phenyl-pyrimido[1,2-b]indazol-2-yl]phenyl}cyclobutyl)-carbamic acid tert-butyl ester | | RT = 1.63 min; m/z = 560 (ES+, M + 1) |

Example 1

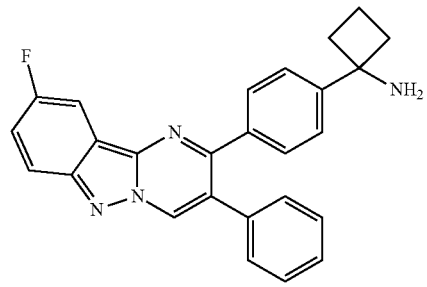 [SMILES: NC1(c2ccc(-c3nc4c5cc(F)ccc5nn4cc3-c3ccccc3)cc2)CCC1]

1-[4-(9-Fluoro-3-phenylpyrimido[1,2-b]indazol-2-yl)phenyl]cyclobutylamine

Step 1: {1-[4-(9-Fluoro-3-phenylpyrimido[1,2-b]indazol-2-yl)phenyl]cyclobutyl}-carbamic acid tert-butyl ester To 620 mg (2.1 mmol) 2-Chloro-9-fluoro-3-phenylpyrimido[1,2-b]indazole (intermediate example Int-1-0) and 1.1 g (2.9 mmol) {1-[4-(4,4,5,5-tetramethyl-1,3,2-dioxaborolan-2-yl)phenyl]cyclobutyl}carbamic acid tert-butyl ester in 7.2 mL 1,2 dimethoxyethane were added 3.8 mL aqueous sodium carbonate (10%) and 170 mg (0.2 mmol) 1,1 bis(diphenylphosphino)ferrocenedichloropalladium(II). The reaction mixture was stirred for 30' in the microwave at 100° C. and subsequently evaporated to dryness. The residue (770 mg=72.7%) was used without further purification in the next step.

Step 2: 1-[4-(9-Fluoro-3-phenylpyrimido[1,2-b]indazole-2-yl)phenyl]-cyclobutylamine 770 mg (1.5 mmol) {1-[4-(9-Fluoro-3-phenylpyrimido[1,2-b]indazole-2-yl)phenyl]-cyclobutyl}carbamic acid tert-butyl ester were dissolved in 9 mL dioxane. After addition of 40

In a second experiment 420 mg (0.83 mmol) {1-[4-(9-fluoro-3-phenylpyrimido[1,2-b]indazole-2-yl)phenyl]cyclobutyl}carbamic acid tert-butyl ester, after dissolution in 5 mL dioxane, were treated with 22 mL 4M hydrogen chloride in dioxane. The reaction mixture was worked up as described for the first experiment. The crude products of both experiments were purified by joint chromatography on amine silicagel (eluents: dichoromethane/methanol) yielding 129.5 mg of the desired product.

UPLC-MS: RT=0.99 min; m/z=392 (ES+, M-NH$_2$)

$^1$H-NMR (300 MHz, dDMSO): δ 9.40 (s, 1H), 7.92-8.03 (m, 1H), 7.81-7.92 (m, 1H), 7.49-7.53 (m, 1H), 7.20-7.48 (m, 9H), 2.21-2.41 (m, 2H), 1.85-2.20 (m, 3H), 1.50-1.70 (m, 1H).

Example 2

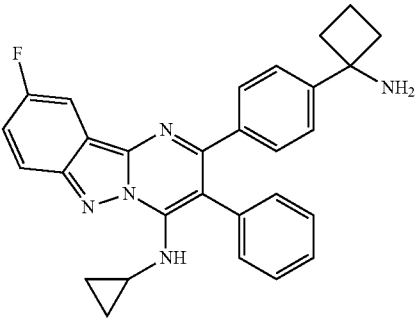 [SMILES: NC1(c2ccc(-c3nc4c5cc(F)ccc5nn4c(NC4CC4)c3-c3ccccc3)cc2)CCC1]

2-[4-(1-Aminocyclobutyl)phenyl]-N-cyclopropyl-9-fluoro-3-phenylpyrimido[1,2-b]indazol-4-amine Step 1: (2-Chloro-9-fluoro-3-phenylpyrimido[1,2-b]indazol-4-yl)cyclopropylamine 1 g (7.5 mmol) 2,4-Dichloro-9-fluoro-3-phenylpyrimido[1,2-b]indazole (intermediate example Int-1-0, step 2) and 430 mg (8.4 mmol) cyclopropylamine were dissolved in 8.4 mL DMF and heated in the microwave for 20' at 100° C. The solvent was evaporated and the residue was purified by chromatography on silicagel (eluents: dichloromethane/methanol) to yield 560 mg (52.7%) of the desired compound.

UPLC-MS: RT=1.55 min; m/z=353/355 (ES+, M+1)

$^1$H-NMR (300 MHz, dDMSO): δ 8.28 (s, 1H), 7.72-7.89 (m, 2H), 7.35-7.58 (m, 6H), 1.90-2.02 (m, 1H), 0.52-0.63 (m, 2H), 0.05-0.19 (m, 2H).

Step 2: (1-{4-[4-(Cyclopropylamino)-9-fluoro-3-phenylpyrimido[1,2-b]indazol-2-yl]phenyl}cyclobutyl)carbamic acid tert-butyl ester 300 mg (0.9 mmol) (2-Chloro-9-fluoro-3-phenylpyrimido[1,2-b]indazol-4-yl)-cyclopropylamine, 444.4 mg (1.2 mmol) {1-[4-(4,4,5,5-tetramethyl-1,3,2-dioxaborolan-2-yl)phenyl]cyclobutyl}carbamic acid tert-butyl ester, 1.6 mL aqueous sodium carbonate (10%) and 31.2 mg (0.04 mmol) 1,1 bis(diphenylphosphino)ferrocenedichloropalladium(II) were given in 2.9 mL dimethoxyethane and heated for 40' in the microwave at 120° C. The reaction mixture was poured on water and ethyl acetate and stirred vigorously for 30 minutes. The organic phase was separated and washed twice with brine. After drying with sodium sulfate the solvent was removed and the crude residue (720 mg) was used in the next step without further purification.

UPLC-MS: RT=1.73 min; m/z=564 (ES+, M+1)

Step 3: 2-[4-(1-Aminocyclobutyl)phenyl]-N-cyclopropyl-9-fluoro-3-phenylpyrimido[1,2-b]indazol-4-amine 720 mg (1.3 mmol) Crude {1-[4-(9-fluoro-4-cyclopropylamino-3-phenyl-pyrimido[1,2-b]indazol-2-yl)phenyl]cyclobutyl}carbamic acid tert-butyl ester, described in step 2, were dissolved in 36 mL dioxane. After dropwise addition of 36 mL of a 4 M hydrogen chloride in dioxane the reaction mixture was stirred for five hours at room temperature. The reaction mixture was evaporated to dryness. Saturated aqueous sodium bicarbonate solution was added and the reaction mixture was extracted three times with ethyl acetate. The combined organic extracts were washed with brine and dried. After evaporation of the solvent the residue was purified by HPLC to yield 44.3 mg of the desired compound which was 90% pure.

UPLC-MS: RT=1.15 min; m/z=447 (ES+, M-NH$_2$)

$^1$H-NMR (300 MHz, dDMSO): δ 7.69-7.90 (m, 3H), 7.09-7.57 (m, 10H), 2.17-2.38 (m, partly obscured by the signal of the solvent, 2H), 1.82-2.13 (m, 4H), 1.49-1.68 (m, 1H), 0.43-0.60 (m, 2H), 0.01-0.19 (m, 2H).

Example 3

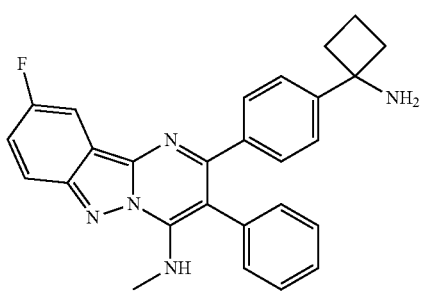 [SMILES: CNc1c(-c2ccccc2)c(-c2ccc(C3(N)CCC3)cc2)nc2c3cc(F)ccc3nn12]

2-[4-(1-Aminocyclobutyl)phenyl]-9-fluoro-N-methyl-3-phenylpyrimido[1,2-b]indazol-4-amine Step 1: (2-Chloro-9-fluoro-3-phenylpyrimido[1,2-b]indazol-4-yl)methylamine 2 g (7.5 mmol) 2,4-Dichloro-9-fluoro-3-phenylpyrimido[1,2-b]indazole (intermediate example Int-1-0, step 2) and 7.5 mL (15 mmol) of a 2M solution of methylamine in tetrahydrofuran were dissolved in 16.8 mL N,N-dimethylformamide and heated in the microwave for 20' at 100° C. The solvent was evaporated and the residue was purified by chromatography on silicagel (eluents: dichloromethane/methanol) yielding 960 mg (46.4%) of the desired compound.

MS (ES+, M+1): 327

$^1$H-NMR (400 MHz, dDMSO): δ 8.35 (s, 1H), 7.31-7.38 (m, 1H), 7.25-7.31 (m, 1H), 7.42-7.53 (m, 6H), 2.41 (s, 3H).

Step 2: (1-{4-[9-Fluoro-4-(methylamino)-3-phenylpyrimido[1,2-b]indazol-2-yl]phenyl}cyclobutyl)carbamic acid tert-butyl ester The compound was prepared by reacting 300 mg (0.92 mmol) (2-chloro-9-fluoro-3-phenylpyrimido[1,2-b]indazole-4-yl)methylamine under the conditions described in the aforementioned example. The crude product (608 mg) was used without further purification in the next step.

UPLC-MS: RT=1.63 min; m/z=538 (ES+, M+1)

Step 3: 2-[4-(1-Aminocyclobutyl)phenyl]-9-fluoro-N-methyl-3-phenylpyrimido[1,2-b]indazol-4-amine 608 mg (1.13 mmol) (1-{4-[9-Fluoro-4-(methylamino)-3-phenylpyrimido[1,2-b]indazol-2-yl]phenyl}cyclobutyl)carbamic acid tert-butyl ester were treated with 4M hydrogen chloride in dioxane as described in the previous example. Purification by HPLC gave 54.3 mg (10.4%) of the title compound.

UPLC-MS: RT=1.05 min; m/z=421 (ES+, M-NH$_2$)

$^1$H-NMR (400 MHz, dDMSO): δ 7.95-8.08 (m, 1H), 7.71-7.85 (m, 2H), 7.40-7.52 (m, 1H), 7.13-7.40 (m, 9H), 2.41 (d, 3H), 2.22-2.36 (m, 2H), 1.99-2.11 (m, 2H), 1.85-1.99 (m, 1H), 1.50-1.65 (m, 1H).

Example 4

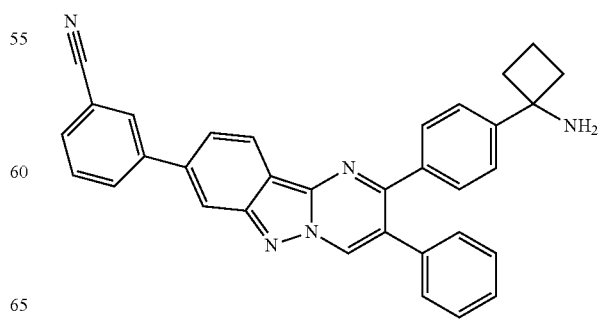

3-{2-[4-(1-Aminocyclobutyl)phenyl]-3-phenylpyrimido[1,2-b]indazol-8-yl}-benzonitrile

Step 1: 3-(2-Chloro-3-phenylpyrimido[1,2-b]indazol-8-yl)benzonitrile 300 mg (0.84 mmol) 8-Bromo-2-chloro-3-phenylpyrimido[1,2-b]indazole (intermediate example Int-1-1), 122.9 mg (0.84 mmol) (3-cyanophenyl)boronic acid, 68.3 mg (0.084 mmol) bis(diphenylphosphino)ferrocenedichloropalladium (II) and 1.5 mL aqueous sodium carbonate solution (10%) in 3 mL dimethoxyethane were heated in the microwave oven for 45' at 100° C. The reaction mixture was poured on water/dichloromethane and stirred vigorously for 30'. The organic phase was separated and washed twice with brine. After drying and filtration the solvent was evaporated and the residue was purified by chromatography on silicagel (eluents: dichloromethane/methanol) yielding 179 mg of a mixture (according to UPLC/MS) of the title compound and the byproduct 3-[2-(3-cyanophenyl)-3-phenyl-pyrimido[1,2-b]indazol-8-yl]-benzonitrile. This mixture was used in the next step without further purification.

UPLC-MS: RT=1.50 min; m/z=381 (ES+, M+1)

Step 2: (1-{4-[8-(3-Cyanophenyl)-3-phenylpyrimido[1,2-b]indazol-2-yl]phenyl}-cyclobutyl)carbamic acid tert-butyl ester 179 mg of the mixture described in step 1,3-(2-chloro-3-phenylpyrimido[1,2-b]indazol-8-yl)benzonitrile and the byproduct 3-[2-(3-cyanophenyl)-3-phenyl-pyrimido[1,2-b]indazol-8-yl]benzonitrile, 210.5 mg (0.56 mmol) {1-[4-(4,4,5,5-tetramethyl-1,3,2-dioxaborolan-2-yl)phenyl]cyclobutyl}carbamic acid tert-butyl ester, 38.4 mg (0.047 mmol) bis(diphenylphosphino)ferrocenedichloropalladium (II) and 0.87 mL aqueous sodium carbonate solution (10%) in 1.6 mL dimethoxyethane were heated in the microwave oven for 60' at 120° C. After the usual work up described in step 1, the mixture (239.4 mg) was used in the next step without further purification.

UPLC-MS: RT=1.67 min; m/z=592 (ES+, M+1)

Step 3: 3-{2-[4-(1-Aminocyclobutyl)phenyl]-3-phenylpyrimido[1,2-b]indazol-8-yl}-benzonitrile 239.4 mg (1-{4-[8-(3-Cyanophenyl)-3-phenylpyrimido[1,2-b]indazol-2-yl]phenyl}-cyclobutyl)carbamic acid tert-butyl ester jointly with the byproduct 3-[2-(3-cyanophenyl)-3-phenylpyrimido[1,2-b]indazol-8-yl]benzonitrile were dissolved in 17 mL 4M hydrogen chloride in dioxane. After stirring over night at room temperature the solvent was evaporated to dryness and the residue was treated with saturated sodium bicarbonate solution. This aqueous solution was extracted three times with ethyl acetate. The combined organic extracts were worked up as already described. The residue was purified by column chromatography on silicagel (eluents: dichloromethane/methanol) and additional HPLC yielding 18.2 mg of the title compound.

UPLC-MS: RT=1.1% min; m/z=475 (ES+, M-NH$_2$)

$^1$H-NMR (400 MHz, CDCl$_3$): δ 8.99 (s, 1H), 8.49 (d, 1H), 7.95-8.10 (m, 3H), 7.68-7.79 (m, 1H), 7.59-7.68 (m, 1H), 7.48-7.59 (m, 3H), 7.30-7.48 (m, 7H), 2.45-2.65 (m, 2H), 1.98-2.29 (m, 3H), 1.58-1.92 (m, completely obscured by the water signal of the solvent, 1H).

The following example has been prepared in analogy according to example 4 by reacting 8-bromo-2-chloro-3-phenylpyrimido[1,2-b]indazole, intermediate example Int-1-1, with the appropriate boronic acid followed by reaction with {1-[4-(4,4,5,5-tetramethyl-1,3,2-dioxaborolan-2-yl)phenyl]cyclobutyl}carbamic acid tert-butyl ester, cleavage of the protecting group and subsequent purification by HPLC.

| Example | Structure/Name | 1H-NMR | UPLC-MS |
| --- | --- | --- | --- |
| 4-1 | 1-{4-[8-(4-Mesylphenyl)-3-phenyl-pyrimido[1,2-b]indazol-2-yl]phenyl}cyclobutylamine | (400 MHz, CDCl$_3$): δ 8.99 (s, 1H), 8.48 (d, 1H), 8.02-8.12 (m, 3H), 7.98 (d, 2H), 7.48-7.55 (m, 4H), 7.30-7.48 (m, 6H), 3.13 (s, 3H), 2.49-2.62 (m, 2H), 2.01-2.29 (m, 3H), 1.59-1.87 (m, nearly complete obscured by the water signal of the solvent, 1H). | RT = 1.04 min; m/z = 528 (ES+, M − NH$_2$) |

Further examples have been prepared in analogy according to example 8 by reacting {1-[4-(8-bromo-3-phenylpyrimido[1,2-b]indazol-2-yl)phenyl]cyclobutyl}-carbamic acid tert-butyl ester, intermediate example Int-2-2, with the appropriate boronic acids followed by cleavage of the protecting group and purification resp. in the case of example 4.3 by direct cleavage of the protecting group and purification. Example 4.8 has been prepared in analogy to example 10.

| Example | Structure/Name | 1H-NMR | UPLC-MS |
|---|---|---|---|
| 4-.2 | 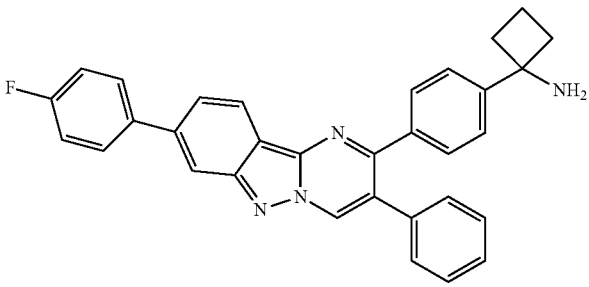<br>1-{4-[8-(4-Fluorophenyl)-3-phenyl-pyrimido[1,2-b]indazol-2-yl]phenyl}-cyclobutylamine | (300 MHz, dDMSO): δ 9.42 (s, 1H), 8.32 (d, 1H), 8.03 (s, 1H), 7.80-7.92 (m, 2H), 7.59 (d, 1H), 7.23-7.48 (m, 11H), 2.25-2.40 (m, 2H), 1.89-2.19 (m, 5H), 1.52-1.69 (m, 1H). | RT = 1.12 min; m/z = 468 (ES+, M − NH$_2$) Method B |
| 4-3 | 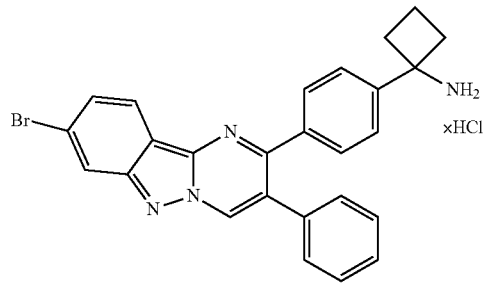<br>1-[4-(8-Bromo-3-phenylpyrimido[1,2-b]indazol-2-yl)phenyl]cyclobutylamine hydrochloride | (300 MHz, dDMSO): δ 9.50 (s, 1H), 8.72 (br., 3H), 8.23 (d, 1H), 8.10 (d, 1H), 7.45-7.58 (m, 4H), 7.30-7.45 (m, 6H), 2.40-2.61 (m, partly obscured by the signal of the solvent, 4H), 2.05-2.22 (m, 1H), 1.68-1.86 (m, 1H). | RT = 1.11 min; m/z = 452 (ES+, M − NH$_2$) |
| 4-4 | 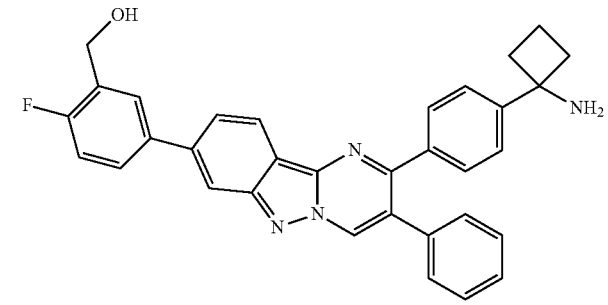<br>5-{2-[4-(1-Aminocyclobutyl)phenyl]-3-phenylpyrimido[1,2-b]indazol-8-yl}-2-fluorobenzyl alcohol | (400 MHz, dDMSO): δ 9.47 (s, 1H), 8.35 (d, 1H), 8.02 (s, 1H), 7.88-7.95 (m, 1H), 7.71-7.80 (m, 1H), 7.61 (d, 1H), 7.20-7.49 (m, 10H), 4.65 (s, 2H), 2.32-2.45 (m, 2H), 2.11-2.25 (m, 2H), 1.92-2.09 (m, 1H), 1.58-1.73 (m, 1H). | RT = 1.04 min; m/z = 498 (ES+, M − NH$_2$) |
| 4-5 | 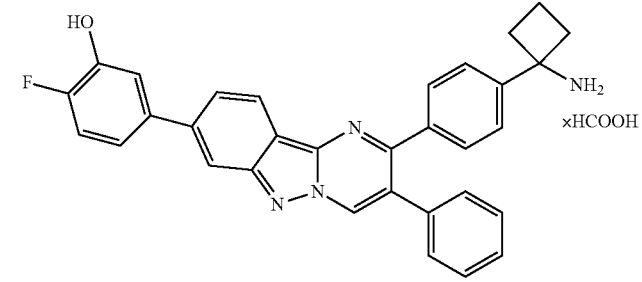<br>5-{2-[4-(1-Aminocyclobutyl)phenyl]-3-phenylpyrimido[1,2-b]indazol-8-yl}-2-fluorophenol formiate | (400 MHz, dDMSO): δ 9.42 (s, 1H), 8.35 (d, 1H), 8.31 (s, 0.5H), 7.95 (s, 1H), 7.05-7.63 (m, 13H), 2.30-2.49 (m, partly obscured by the signal of the solvent, 2H), 2.10-2.28 (m, 2H), 1.91-2.10 (m, 1H), 1.58-1.76 (m, 1H). | RT = 1.05 min; m/z = 484 (ES+, M − NH$_2$) |

-continued

| Example | Structure/ Name | 1H-NMR | UPLC-MS |
|---|---|---|---|
| 4-6 | 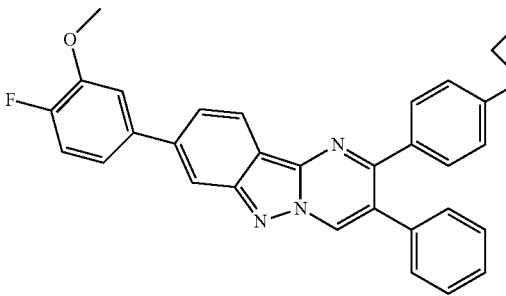<br>1-{4-[8-(4-Fluoro-3-methoxyphenyl)-3-phenylpyrimido[1,2-b]indazol-2-yl]phenyl}-cyclobutylamine | (400 MHz, dDMSO): δ 9.45 (s, 1H), 8.32 (d, 1H), 8.10 (s, 1H), 7.65 (d, 1H), 7.59 (d, 1H), 7.22-7.50 (m, 11H), 2.31-2.48 (m, partly obscured by the signal of the solvent, 2H), 2.10-2.28 (m, 2H), 1.91-2.09 (m, 1H), 1.59-1.73 (m, 1H). | RT = 1.18 min; m/z = 498 (ES+, M − NH$_2$) |
| 4-7 | 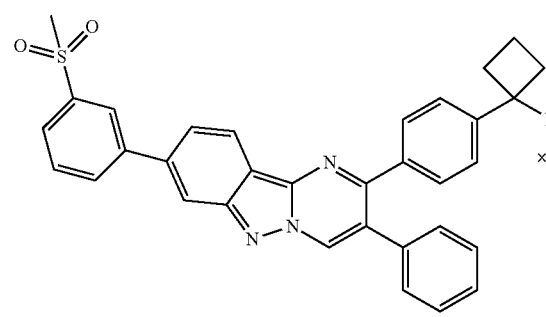<br>1-{4-[8-(3-Mesylphenyl]-3-phenylpyrimido-[1,2-b]indazol-2-yl]phenyl}cyclobutylamine formiate | (400 MHz, dDMSO): δ 9.48 (s, 1H), 8.41 (d, 1H), 8.33 (s, 1H), 8.18-8.30 (m, 2H and 0.6H), 7.98 (d, 1H), 7.81 (dd, 1H), 7.71 (d, 1H), 7.30-7.50 (m, 9H), 3.33 (s, 3H), 2.33-2.47 (m, partly obscured by the signal of the solvent, 2H), 2.12-2.28 (m, 2H), 1.92-2.09 (m, 1H), 1.61-1.73 (m, 1H). | RT = 1.01 min; m/z = 528 (ES+, M − NH$_2$) |
| 4-8 | 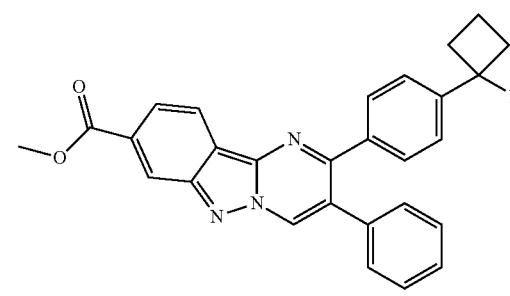<br>2-[4-(1-Aminocyclobutyl)phenyl]-3-phenyl-pyrimido[1,2-b]indazol-8-carboxylic acid methyl ester | (400 MHz, dDMSO): δ 9.52 (s, 1H), 8.45 (s, 1H), 8.39 (d, 1H), 7.80 (d, 1H), 7.29-7.50 (m, 9H), 3.95 (s, 3H), 2.32-2.47 (m, partly obscured by the signal of the solvent, 2H), 2.12-2.28 (m, 2H), 1.92-2.09 (m, 1H), 1.61-1.75 (m, 1H). | RT = 1.02 min; m/z = 432 (ES+, M − NH$_2$) |
| 4-9 | 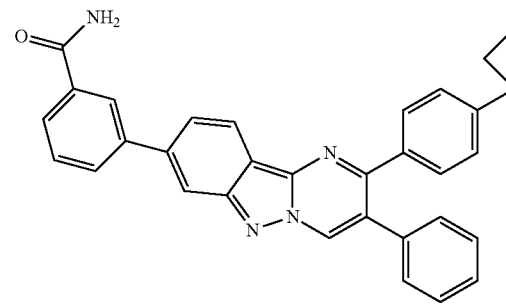<br>3-{2-[4-(1-Aminocyclobutyl)phenyl]-3-phenylpyrimido[1,2-b]indazol-8-yl}-benzamide | (400 MHz, dDMSO): δ 9.43 (s, 1H), 8.28-8.41 (m, 2H), 8 18 (s, 2H), 8.01 (d, 1H), 7.92 (d, 1H), 7.71 (d, 1H), 7.60 (dd, 1H), 7.28-7.50 (m, 10H), 2.25-2.40 (m, 2H), 1.90-2.20 (m, 5H), 1.52-1.70 (m, 1H). | RT = 0.92 min; m/z = 510 (ES+, M + 1) |

| Example | Structure/ Name | 1H-NMR | UPLC-MS |
|---|---|---|---|
| 4-10 | 4-{2-[4-(1-Aminocyclobutyl)phenyl]-3-phenylpyrimido[1,2-b]indazol-8-yl}-benzamide | (400 MHz, dDMSO): δ 9.43 (s, 1H), 8.33 (d, 1H), 8.13 (s, 1H), 7.98-8.10 (m, 3H), 7.92 (d, 2H), 7.67 (d, 1H), 7.25-7.50 (m, 10H), 2.25-2.40 (m, 2H), 1.90-2.25 (m, 5H), 1.57-1.69 (m, 1H). | RT = 0.89 min; m/z = 510 (ES+, M + 1) |
| 4-11 | 1-{4-[3-Phenyl-8-(1H-pyrazol-4-yl)-pyrimido[1,2-b]indazol-2-yl]phenyl}cyclo-butylamine | (300 MHz, dDMSO): δ 9.38 (s, 1H), 8.15-8.35 (m, 4H), 8.02 (s, 1H), 7.60 (d, 1H), 7.25-7.50 (m, 9H), 2.30-2.48 (m, partly obscured by the signal of the solvent, 2H), 2.12-2.30 (m, 2H), 1.90-2.10 (m, 1H), 1.58-1.76 (m, 1H). | RT = 0.89 min; m/z = 440 (ES+, M − $NH_2$) |
| 4-12 | 5-{2-[4-(1-Aminocyclobutyl)phenyl]-3-phenylpyrimido[1,2-b]indazol-8-yl}pyridin-2-ol | (300 MHz, dDMSO): δ 9.40 (s, 1H), 8.28 (d, 1H), 7.81-8.10 (m, 3H), 7.52 (d, 1H), 7.20-7.48 (m, 9H), 6.49 (d, 1H), 2.25-2.43 (m, partly obscured by the signal of the solvent, 2H), 1.87-2.15 (m, 3H), 1.51-1.70 (m, 1H). | RT = 0.85 min; m/z = 484 (ES+, M + 1) |
| 4-13 | 5-{2-[4-(1-Aminocyclobutyl)phenyl]-3-phenylpyrimido[1,2-b]indazol-8-yl}-pyridine-2-carboxylic acid methyl ester | (400 MHz, dDMSO): δ 9.49 (s, 1H), 9.22 (s, 1H), 8.38-8.51 (m, 2H), 8.30 (s, 1H), 8.18 (d, 1H), 7.75 (d, 1H), 7.32-7.54 (m, 9H), 3.92 (s, 3H), 2.34-2.58 (m, completely obscured by the signal of the solvent, 2H), 2.13-2.32 (m, 2H), 1.91-2.11 (m, 1H), 1.60-1.78 (m, 1H). | RT = 1.01 min; m/z - 526 (ES+, M + 1) |

Example 5

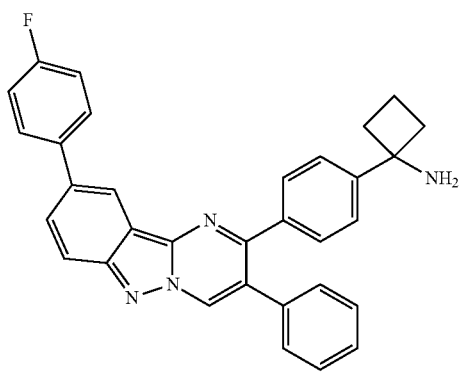 [SMILES: NC1(c2ccc(-c3nc4c5cc(-c6ccc(F)cc6)ccc5nn4cc3-c3ccccc3)cc2)CCC1]

1-{4-[9-(4-Fluorophenyl)-3-phenylpyrimido[1,2-b]indazol-2-yl]phenyl}-cyclobutylamine

Step 1: 2-Chloro-9-(4-fluorophenyl)-3-phenylpyrimido[1,2-b]indazole 300 mg (0.84 mmol) 9-Bromo-2-chloro-3-phenylpyrimido[1,2-b]indazole, (intermediate example Int-1-2), 128.7 mg (0.92 mmol) (4-fluorophenyl)boronic acid, 68.3 mg (0.084 mmol) bis(diphenylphosphino)ferrocenedichloropalladium (II) and 1.5 mL aqueous sodium carbonate solution (10%) in 10 mL dimethoxyethane were heated in the microwave oven for 45' at 110° C. The reaction mixture was poured on water/dichloromethane and stirred vigorously for 30'. The organic phase was separated and washed twice with brine. After drying and filtration the solvent was evaporated and the residue (194 mg), a mixture (according to UPLC/MS) of the title compound, the regioisomer 9-bromo-2-(4-fluorophenyl)-3-phenyl-pyrimido[1,2-b]indazole and the bisproduct 2,9-bis-(4-fluorophenyl)-3-phenyl-pyrimido[1,2-b]indazole, was used in the next step without further purification.

UPLC-MS: RT=1.61 min; m/z=374 (ES+, M+1)

Step 2: (1-{4-[9-Fluorophenyl)-3-phenylpyrimido[1,2-b]indazol-2-yl]phenyl}-cyclobutyl)carbamic acid tert-butyl ester 194 mg of the mixture described in step 1,2-chloro-9-(4-fluorophenyl)-3-phenyl-pyrimido[1,2-b]indazole, the regioisomer 9-bromo-2-(4-fluorophenyl)-3-phenyl-pyrimido[1,2-b]indazole and the bisproduct 2,9-bis-(4-fluorophenyl)-3-phenyl-pyrimido[1,2-b]indazole, 213.2 mg (0.57 mmol) {1-[4-(4,4,5,5-tetramethyl-1,3,2-dioxaborolan-2-yl)phenyl]cyclobutyl}carbamic acid tert-butyl ester, 42 mg (0.052 mmol) bis(diphenylphosphino)ferrocenedichloropalladium (II) and 0.96 mL aqueous sodium carbonate solution (10%) in 1.8 mL dimethoxyethane were heated in the microwave oven for 60' at 120° C. After the usual work up as described in step 1, the mixture (260.3 mg) was used in the next step without further purification.

Step 3: 1-{4-[9-(4-Fluorophenyl)-3-phenylpyrimido[1,2-b]indazol-2-yl]phenyl}-cyclobutylamine 260 mg of the mixture described in step 2 in 15 mL 4M hydrogen chloride in dioxane were stirred over night at room temperature. After evaporation of the solvent the residue was treated with saturated sodium bicarbonate solution. This aqueous solution was extracted three times with dichloromethane. The combined organic extracts were worked up as already described. The residue was purified by column chromatography on silicagel (eluents: dichloromethane/methanol) and additional HPLC yielding 24.1 mg of the title compound 1-{4-[9-(4-fluorophenyl)-3-phenylpyrimido[1,2-b]indazol-2-yl]phenyl}cyclobutylamine and 12.1 mg of the regioisomer 1-{4-[2-(4-fluorophenyl)-3-phenylpyrimido[1,2-b]indazol-9-yl]phenyl}-cyclobutylamine.

UPLC-MS: RT=1.09 min; m/z=468 (ES+, M-NH$_2$); Method C

1H-NMR (300 MHz, CDCl$_3$): δ 8.95 (s, 1H), 8.54 (s, 1H), 7.82-8.00 (m, 2H), 7.62-7.80 (m, 2H), 7.50 (d, 2H), 7.08-7.45 (m, partly obscured by the signal of the solvent, 9H), 2.43-2.60 (m, 2H), 1.99-2.29 (m, 3H), 1.69-2.00 (m, completely obscured by the water signal of the solvent, 1H).

The following examples have been prepared in analogy according to example 5 by reacting 9-bromo-2-chloro-3-phenylpyrimido[1,2-b]indazole, intermediate example Int-1-2, with the appropriate boronic acids followed by reaction with {1-[4-(4,4,5,5-tetramethyl-1,3,2-dioxaborolan-2-yl)phenyl]cyclobutyl}carbamic acid tert-butyl ester, cleavage of the protecting group and subsequent separation of the regioisomers by HPLC.

| Example | Structure/Name | 1H-NMR | UPLC-MS |
| --- | --- | --- | --- |
| 5-1 | 1-[4-(3-Phenyl-9-p-tolylpyrimido[1,2-b]indazol-2-yl)phenyl]cyclobutylamine | (400 MHz, CDCl$_3$): δ 8.95 (s, 1H), 8.59 (s, 1H), 7.87-7.99 (m, 2H), 7.69 (d, 2H), 7.52 (d, 2H), 7.28-7.48 (m, 9H), 2.48-2.60 (m, 2H), 2.43 (s, 3H), 2.15-2.25 (m, 2H), 2.02-2.15 (m, 1H), 1.62-1.95 (m, obscured by the water signal of the solvent, 1H). | RT = 1.21 min; m/z = 464 (ES+, M − NH$_2$) |

| Example | Structure/Name | 1H-NMR | UPLC-MS |
|---|---|---|---|
| 5-2 | 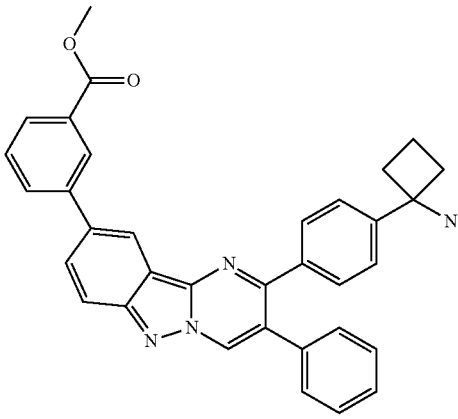<br>3-{2-[4-(1-Aminocyclobutyl)phenyl]-3-phenylpyrimido[1,2-b]indazol-9-yl}-benzoic acid methyl ester | (400 MHz, CDCl$_3$): δ 8.98 (s, 1H), 8.68 (s, 1H), 8.49 (s, 1H), 8.05 (d, 1H), 7.89-8.01 (m, 3H), 7.48-7.62 (m, 3H), 7.29-7.48 (m, 7H), 3.99 (s, 3H), 2.49-2.60 (m, 2H), 2.13-2.26 (m, 2H), 1.99-2.13 (m, partly obscured by the signal of the water, 1H), 1.70-1.85 (m, 1H). | RT = 1.15 min; m/z - 508 (ES+, M − NH$_2$) |

Example 6

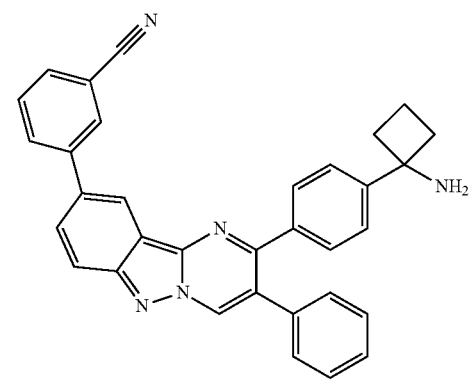 [SMILES: N#Cc1cccc(-c2ccc3nn4cc(-c5ccccc5)c(-c5ccc(C6(N)CCC6)cc5)nc4c3c2)c1]

3-{2-[4-(1-Aminocyclobutyl)phenyl]-3-phenylpyrimido[1,2-b]indazol-9-yl}-benzonitrile Step 1: (1-{4-[9-(3-Cyanophenyl)-3-phenylpyrimido[1,2-b]indazol-2-yl]phenyl}-cyclobutyl)carbamic acid tert-butyl ester 100 mg (0.18 mmol) {1-[4-(9-Bromo-3-phenylpyrimido[1,2-b]indazole-2-yl)phenyl]-cyclobutyl}carbamic acid tert-butyl ester (intermediate example Int-2-0), 51.6 mg (0.35 mmol) (3-cyanophenyl)boronic acid, 14.3 mg (0.02 mmol) bis(diphenylphosphino)ferrocenedichloropalladium(II) and 55 mg (0.53 mmol) sodium carbonate in 1.8 mL dioxane and 0.3 mL water were heated in a microwave vial which had been sealed with a microwave cap for 18 hours at 105° C. (heating block). After the usual work up, the crude mixture (131.2 mg) was used in the next step without further purification.

UPLC-MS: RT=1.65 min; m/z=592 (ES+, M+1)

Step 2: 3-{2-[4-(1-Aminocyclobutyl)phenyl]-3-phenylpyrimido[1,2-b]indazol-9-yl}-benzonitrile 126.9 mg (0.21 mmol) (1-{4-[9-(3-Cyanophenyl)-3-phenylpyrimido[1,2-b]indazol-2-yl]phenyl}cyclobutyl)carbamic acid tert-butyl ester in 7 mL 4M hydrogen chloride in dioxane were stirred over night at room temperature. The solvent was evaporated and the residue was treated with saturated sodium bicarbonate solution. After extraction with dichloromethane (three times) the combined organic extracts were washed with brine, dried (sodium sulfate) and filtrated. The solvent was removed and the residue (102 mg) was purified by HPLC yielding 42 mg (37.9%) of the title compound.

UPLC-MS: RT=1.11 min; m/z=475 (ES+, M-NH$_2$)

$^1$H-NMR (300 MHz, CD$_3$OD): δ 9.19 (s, 1H), 8.57 (s, 1H), 8.00-8.11 (m, 2H), 7.96 (d, 1H), 7.88 (d, 1H), 7.59-7.72 (m, 4H), 7.49 (d, 2H), 7.30-7.42 (m, 5H), 2.68-2.80 (m, 2H), 2.48-2.60 (m, 2H), 2.14-2.30 (m, 1H), 1.85-2.02 (m, 1H).

The following examples have been prepared in analogy according to example 6 by reacting {1-[4-(9-bromo-3-phenylpyrimido[1,2-b]indazol-2-yl)phenyl]cyclobutyl}-carbamic acid tert-butyl ester, intermediate example Int-2-0, with the appropriate boronic acids followed by cleavage of the protecting group and purification resp. in the case of example 6.1. by direct cleavage of the protecting group and purification.

| Example | Structure/Name | 1H-NMR | UPLC-MS resp. MS |
|---|---|---|---|
| 6-1 | 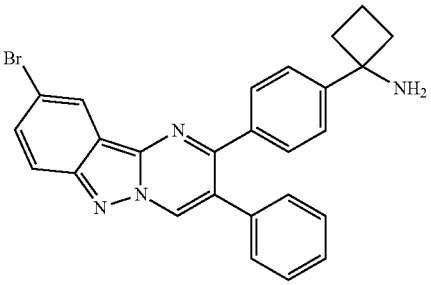<br>1-[4-(9-Bromo-3-phenylpyrimido[1,2-b]indazol-2-yl)phenyl]cyclobutyl-amine | (400 MHz, CDCl$_3$): δ 8.93 (s, 1H), 8.56 (s, 1H), 7.66-7.79 (m, 2H), 7.50 (d, 2H), 7.29-7.47 (m, 7H), 2.49-2.62 (m, 2H), 2.00-2.23 (m, 3H), 1.69-1.82 (m, obscured by the water signal of the solvent, 1H). | MS (ES+, M – NH$_2$): 452/454 |
| 6-2 | 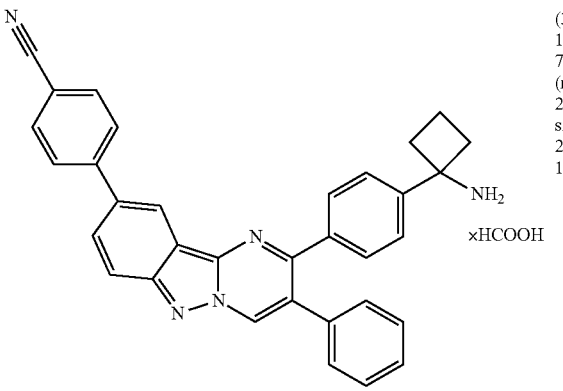<br>4-{2-[4-(1-Aminocyclobutyl)phenyl]-3-phenylpyrimido[1,2-b]indazol-9-yl}-benzonitrile formiate | (300 MHz, dDMSO): δ 9.46 (s, 1H), 8.61 (s, 1H), 8.20 (s, 1H), 7.99-8.10 (m, 3H), 7.88-7.98 (m, 3H), 7.32-7.52 (m, 9H), 2.32-2.55 (m, obscured by the signal of the solvent, 2H), 2.18-2.32 (m, 2H), 1.93-2.13 (m, 1H), 1.58-1.79 (m, 1H). | RT = 1.11 min; m/z = 475 (ES+, M – NH$_2$) |
| 6-3 | 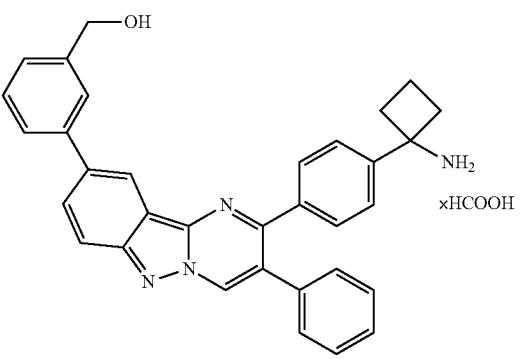<br>3-{2-[4-(1-Aminocyclobutyl)phenyl]-3-phenylpyrimido[1,2-b]indazol-9-yl}-benzyl alcohol formiate | (400 MHz, dDMSO): δ 9.45 (s, 1H), 8.49 (s, 1H), 8.22 (s, 1H), 8.00 (d, 1H), 7.91 (d, 1H), 7.78 (s, 1H), 7.69 (d, 1H), 7.32-7.52 (m, 10H), 7.30 (d, 1H), 4.59 (s, 2H), 2.35-2.45 (m, slightly obscured by the signal of the solvent, 2H), 2.12-2.29 (m, 2H), 1.90-2.09 (m, 1H), 1.59-1.74 (m, 1H). | RT = 1.02 min; m/z = 480 (ES+, M – NH$_2$) |

| Example | Structure/Name | 1H-NMR | UPLC-MS resp. MS |
|---|---|---|---|
| 6-.4 | 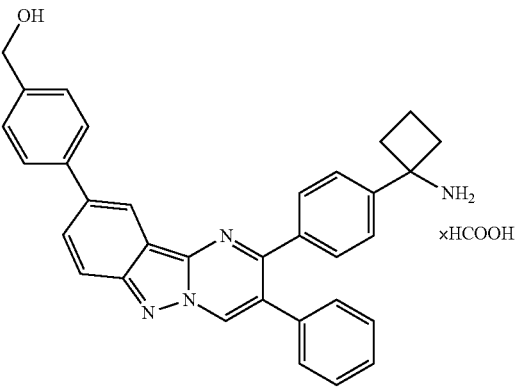<br>4-{2-[4-(1-Aminocyclobutyl)phenyl]-3-phenylpyrimido[1,2-b]indazol-9-yl}-benzyl alcohol formiate | (300 MHz, dDMSO): δ 9.49 (s, 1H), 8.49 (s, 1H), 8.20 (s, 1H), 8.00 (d, 1H), 7.91 (d, 1H), 7.79 (d, 2H), 7.18-7.60 (m, 11H), 4.56 (s, 2H), 2.38-2.62 (m. obscured by the signal of the solvent, 2H), 2.18-2.38 (m, 2H), 1.90-2.16 (m, 1H), 1.58-1.79 (m, 1H). | RT = 1.01 min; m/z = 480 (ES+, M − NH$_2$) |
| 6-5 | 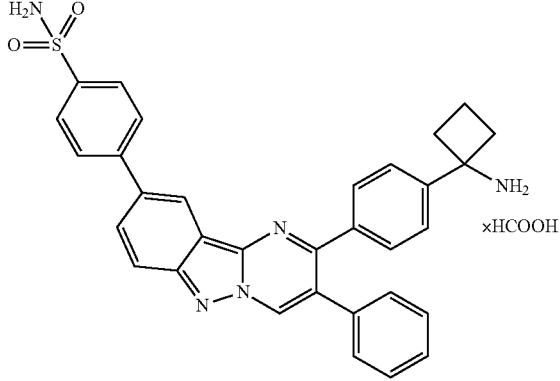<br>4-{2-[4-(1-Aminocyclobutyl)phenyl]-3-phenylpyrimido[1,2-b]indazol-9-yl}-benzenesulfonamide formiate | (400 MHz, dDMSO): δ 9.49 (s, 1H), 8.62 (s, 1H), 8.22 (s, 1H), 7.99-8.10 (m, 3H), 7.85-7.99 (m, 3H), 7.29-7.52 (m, 11H), 2.34-2.45 (m, slightly obscured by the signal of the solvent, 2H), 2.14-2.29 (m, 2H), 1.92-2.10 (m, 1H), 1.60-1.73 (m, 1H). | RT = 0.96 min; m/z = 529 (ES+, M − NH$_2$) |
| 6-.6 | 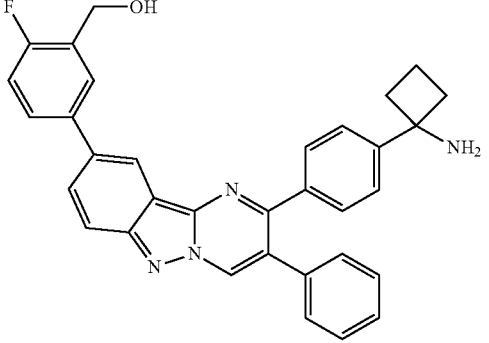<br>5-{2-[4-(1-Aminocyclobutyl)phenyl]-3-phenylpyrimido[1,2-b]indazol-9-yl}-2-fluorobenzyl alcohol | (400 MHz, dDMSO): δ 9.41 (s, 1H), 8.45 (s, 1H), 7.85-8.00 (m, 3H), 7.68-7.78 (m, 1H), 7.32-7.48 (m, 9H), 7.23 (dd, 1H), 5.32 (br., 1H), 4.62 (d, 2H), 2.25-2.40 (m, 2H), 1.89-2.23 (m, 5H), 1.55-1.69 (m, 1H). | RT = 1.04 min; m/z = 498 (ES+, M − NH$_2$) |

-continued

| Example | Structure/Name | 1H-NMR | UPLC-MS resp. MS |
|---|---|---|---|
| 6-7 | 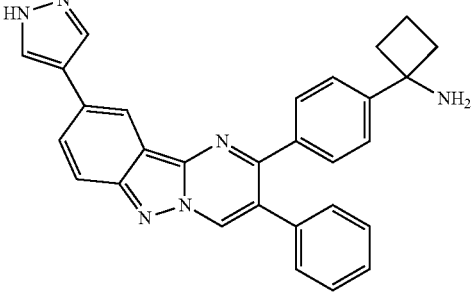<br>1-{4-[3-Phenyl-9-(1H-pyrazol-4-yl)-pyrimido[1,2-b]indazol-2-yl]phenyl}-cyclobutylamine | (400 MHz, dDMSO): δ 9.38 (s, 1H), 8.43 (s, 1H), 8.19 (br., 2H), 7.97 (d, 1H), 7.82 (d, 1H), 7.32-7.48 (m, 9H), 2.28-2.41 (m, 2H), 2.03-2.12 (m, 2H), 1.89-2.03 (m, 1H), 1.58-1.70 (m, 1H). | RT = 0.92 min; m/z = 440 (ES+, M − NH$_2$) |

Example 7

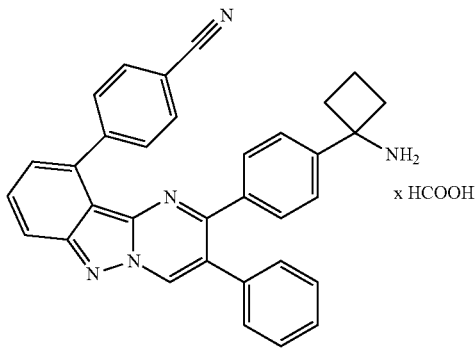 [SMILES: N#Cc1ccc(-c2cccc3nn4cc(-c5ccccc5)c(-c5ccc(C6(N)CCC6)cc5)nc4c23)cc1]

4-{2-[4-(1-Aminocyclobutyl)phenyl]-3-phenylpyrimido[1,2-b]indazol-10-yl}-benzonitrile formiate

Step 1: 4-(2-Chloro-3-phenylpyrimido[1,2-b]indazol-10-yl)benzonitrile 400 mg (1.12 mmol) 10-Bromo-2-chloro-3-phenylpyrimido[1,2-b]indazole, intermediate example Int-1-3, 172.1 mg (1.17 mmol) 4-cyanophenylboronic acid, 91 mg (0.112 mmol) bis(diphenylphosphino)ferrocenedichloropalladium (II) and 354.6 mg (3.35 mmol) sodium carbonate in 12 mL degassed dioxane and 1.68 mL water were heated in the microwave for 45 min. at 105° C. The reaction mixture was poured on a mixture of water/saturated ammonium chloride/dichloromethane and stirred vigorously for 30'. The organic phase was separated, washed twice with brine and dried (sodium sulfate). After filtration and evaporation of the solvent the residue was purified by HPLC yielding 114 mg of the title compound.

UPLC-MS: RT=1.51 min; m/z=381 (ES+, M+1)

$^1$H-NMR (300 MHz, dDMSO): δδ☐ 9.59 (s, 1H), 7.80-8.05 (m, 4H), 7.73 (dd, 1H), 7.42-7.67 (m, 6H), 7.38 (d, 1H).

Step 2: (1-{4-[10-(4-Cyanophenyl)-3-phenylpyrimido[1,2-b]indazol-2-yl]phenyl}-cyclobutyl)carbamic acid tert-butyl ester 114 mg (0.3 mmol) 4-(2-Chloro-3-phenylpyrimido[1,2-b]indazol-10-yl)benzonitrile, 122.9 g (0.3 mmol) {1-[4-(4,4,5,5-tetramethyl-1,3,2-dioxaborolan-2-yl)phenyl]-cyclobutyl}carbamic acid tert-butyl ester, 34.6 mg (0.03 mmol) tetrakistriphenylphosphinepalladium(0) and 95 mg (0.90 mmol) sodium carbonate in 3.2 mL dioxane and 0.45 mL water were heated in a microwave vial which had been sealed with a microwave cap over night at 105° C. (heating block). After the usual work up, the crude mixture (235 mg) was used in the next step without further purification.

Step 3: 4-{2-[4-(1-Aminocyclobutyl)phenyl]-3-phenylpyrimido[1,2-b]indazol-10-yl}-benzonitrile formiate 235 mg (1-{4-[10-(4-Cyanophenyl)-3-phenylpyrimido[1,2-b]indazol-2-yl]phenyl}-cyclobutyl)carbamic acid tert-butyl ester in 15 mL 4M hydrogen chloride in dioxane were stirred over night at room temperature. The solvent was evaporated and the residue was treated with saturated sodium bicarbonate. After extraction with dichloromethane (trice) the combined organic phases were washed with brine and dried (sodium sulfate). The solvent was evaporated and the residue (189 mg) was purified by HPLC yielding 50 mg of the title compound.

$^1$H-NMR (400 MHz, dDMSO): δ☐ 9.48 (s, 1H), 8.21 (s, 1H), 8.15 (d, 2H), 8.03 (d, 2H), 7.90 (d, 1H), 7.73 (dd, 1H), 7.28-7.45 (m, 10H), 2.25-2.42 (m, 2H), 2.09-2.22 (m, 2H), 1.91-2.07 (m, 1H), 1.58-1.70 (m, 1H).

The following examples have been prepared in analogy according to example 7 by reacting 10-bromo-2-chloro-3-phenylpyrimido[1,2-b]indazole, intermediate example Int-1-3, with the appropriate boronic acids followed by reaction of the resulting intermediate with {1-[4-(4,4,5,5-tetramethyl-1,3,2-dioxaborolan-2-yl)-phenyl]cyclobutyl}carbamic acid tert-butyl ester, cleavage of the protecting group and subsequent purification.

| Example | Structure/Name | 1H-NMR | UPLC-MS |
|---|---|---|---|
| 7-1 | 1-[4-(3-Phenyl-10-p-tolylpyrimido[1,2-b]indazol-2-yl)phenyl]cyclobutyl-amine × 0.5 formiate | (400 MHz, dDMSO): δ 9.40 (s, 1H), 8.23 (s, 0.5H), 7.74-7.88 (m, 3H), 7.67 (dd, 1H), 7.29-7.48 (m, 11H), 7.28 (d, 1H), 2.40 (s, 3H), 2.28-2.38 (m, 2H), 2.02-2.17 (m, 2H), 1.89-2.02 (m, 1H), 1.53-1.79 (m, 1H). | RT = 1.25 min; m/z = 464 (ES+, M − NH$_2$) |
| 7-2 | 1{4-[10-(4-Fluorophenyl)-3-phenyl-pyrimido[1,2-b]indazol-2-yl)phenyl}-cyclobutylamine formiate | (300 MHz, dDMSO): δ 9.44 (s, 1H), 8.22 (s, 1H), 7.91-8.01 (m, 2H), 7.82 (d, 1H), 7.69 (dd, 1H), 7.29-7.45 (m, 11H), 7.28 (d, 1H), 2.26-2.41 (m, 2H), 2.08-2.19 (m, 2H), 1.90-2.08 (m, 1H), 1.57-1.70 (m, 1H). | RT = 1.19 min; m/z = 468 (ES+, NH$_2$) |
| 7-3 | 4-{2-[4-(1-Aminocyclobutyl)phenyl]-3-phenyl-pyrimido[1,2-b]indazol-10-yl}-benzyl alcohol formiate | (400 MHz, dDMSO): δ 9.40 (s, 1H), 8.21 (s, 1H), 7.90 (d, 2H), 7.80 (d, 1H), 7.69 (dd, 1H), 7.50 (d, 2H), 7.21-7.45 (m, 10H), 4.59 (s, 2H), 2.28-2.42 (m, 2H), 2.07-2.22 (m, 2H), 1.90-2.07 (m, 1H), 1.58-1.72 (m, 1H). | RT = 1.11 min; m/z = 480 (ES+, M − NH$_2$) |

Example 8

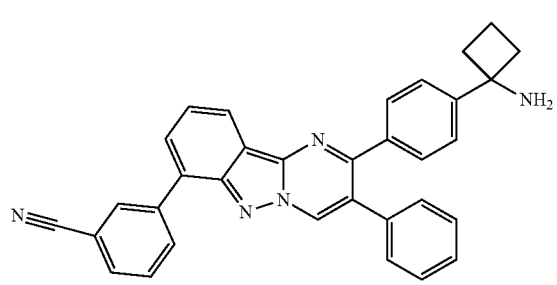 [SMILES: N#Cc1cccc(-c2cccc3c2nn2cc(-c4ccccc4)c(-c4ccc(C5(N)CCC5)cc4)nc32)c1]

3-{2-[4-(1-Aminocyclobutyl)phenyl]-3-phenylpyrimido[1,2-b]indazol-7-yl}-benzonitrile Step 1: (1-{4-[7-(3-Cyanophenyl)-3-phenylpyrimido[1,2-b]indazol-2-yl]phenyl}-D cyclobutyl)carbamic acid tert-butyl ester 80 mg (0.14 mmol) {1-[4-(7-Bromo-3-phenylpyrimido[1,2-b]indazol-2-yl)phenyl]-cyclobutyl}carbamic acid tert-butyl ester (intermediate example Int-2-1), 41.3 mg (0.28 mmol) (3-cyanophenyl)boronic acid, 11.5 mg (0.014 mmol) bis(diphenylphosphino)ferrocenedichloropalladium(II) and 44.6 mg (0.42 mmol) sodium carbonate in 1.5 mL dioxane and 0.2 mL water were heated in a microwave for 30' at 105° C. The reaction mixture was poured on a mixture of water/saturated ammonium chloride/dichloromethane and stirred vigorously for 30'. The organic phase was separated, washed twice with brine and dried (sodium sulfate). After filtration and evaporation of the solvent, the crude residue (172 mg) was used in the next step without further purification.

Step 2: 3-{2-[4-(1-Aminocyclobutyl)phenyl]-3-phenylpyrimido[1,2-b]indazol-7-yl}-benzonitrile 172 mg (0.21 mmol) (1-{4-[9-(3-Cyanophenyl)-3-phenylpyrimido[1,2-b]indazol-2-yl]phenyl}cyclobutyl)carbamic acid tert-butyl ester in 12 mL 4M hydrogen chloride in dioxane were stirred over night at room temperature. The solvent was evaporated and the residue was treated with saturated sodium bicarbonate solution. After extraction with dichloromethane (three times) the combined organic extracts were washed with brine, dried (sodium sulfate) and filtrated. The solvent was removed and the crude residue (117 mg) was purified by HPLC yielding 23 mg of the title compound.

UPLC-MS: RT=1.28 min; m/z=475 (ES+, M-NH$_2$)

$^1$H-NMR (300 MHz, dDMSO): δ 9.58 (s, 1H), 8.68 (d, 1H), 8.49 (d, 1H), 8.36 (d, 1H), 7.99 (d, 1H), 7.89 (d, 1H), 7.75 (dd, 1H), 7.30-7.48 (m, 10H), 2.28-2.43 (m, 2H), 1.89-2.18 (m, 3H), 1.54-1.70 (m, 1H).

The following examples have been prepared in analogy according to example 8 by reacting {1-[4-(7-bromo-3-phenylpyrimido[1,2-b]indazol-2-yl)phenyl]cyclobutyl}-carbamic acid tert-butyl ester (intermediate example Int-2-1) with the appropriate boronic acids followed by cleavage of the protecting group and purification resp. in the case of example 8.1. by direct cleavage of the protecting group and purification

| Example | Structure/Name | 1H-NMR | UPLC-MS |
|---|---|---|---|
| 8-1 | 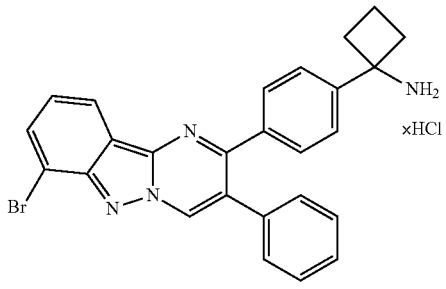<br>1-[4-(7-Bromo-3-phenylpyrimido[1,2-b]indazol-2-yl)phenyl]cyclobutylamine hydrochloride | (300 MHz, dDMSO): δ 9.62 (s, 1H), 8.65-8.92 (m, br., 3H), 8.31 (s, 1H), 7.93 (s, 1H), 7.45-7.59 (m, 4H), 7.33-7.45 (m, 5H), 7.22 (dd, 1H), 2.48-2.65 (m, partly obscured by the signal of the solvent, 4H), 2.05-2.29 (m, 1H), 1.65-1.88 (m, 1H). | RT = 1.12 min; m/z = 469/471 (ES+, M + 1) |
| 8-2 | 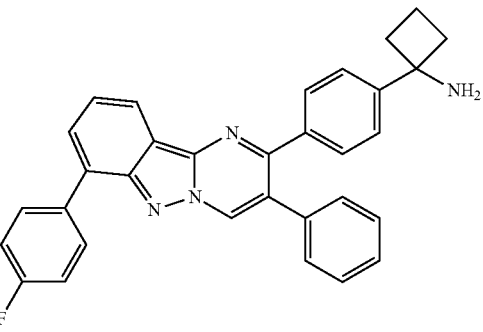<br>1-{4-[7-(4-Fluorophenyl)-3-phenylpyrimido[1,2-b]indazol-2-yl]phenyl}-cyclobutylamine | (400 MHz, dDMSO): δ 9.52 (s, 1H), 8.29 (d, 1H), 8.14-8.23 (m, 2H), 7.83 (d, 1H), 7.30-7.48 (m, 12H), 2.31-2.43 (m, 2H), 2.08-2.20 (m, 2H), 1.92-2.08 (m, 1H), 1.58-1.72 (m, 1H). | RT = 1.30 min; m/z = 468 (ES+, M – NH2) |
| 8-3 | 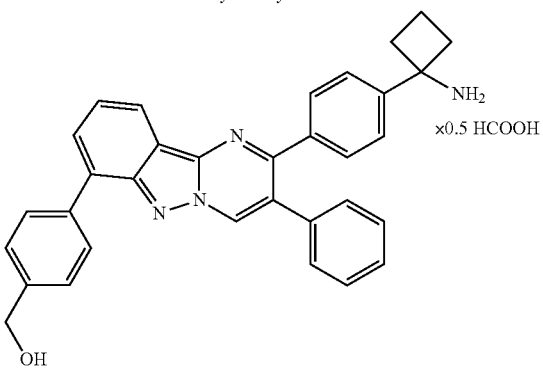<br>4-{2-[4-(1-Aminocyclobutyl)phenyl]-3-phenylpyrimido[1,2-b]indazol-7-yl}benzyl alcohol formiate | (300 MHz, dDMSO): δ 9.50 (s, 1H), 8.25 (d, 1H), 8.22 (s, 0.5H), 8.11 (d, 2H), 7.82 (d, 1H), 7.28-7.51 (m, 12H), 4,58 (s, 2H), 2.30-2.46 (m, 2H), 2.06-2.20 (m, 2H), 1.92-2.06 (m, 1H), 1.58-1.72 (m, 1H). | RT = 1.07 min; m/z = 480 (ES+, M – NH2) |

| Example | Structure/Name | 1H-NMR | UPLC-MS |
|---|---|---|---|
| 8-4 | 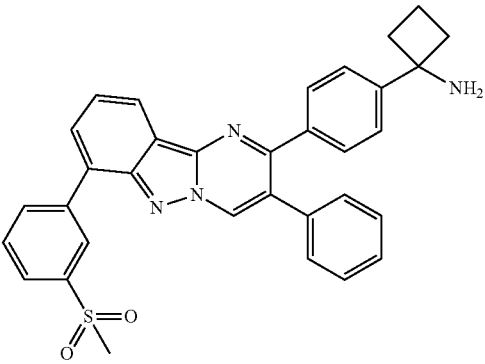 1-{4-[7-(3-Mesylphenyl)-3-phenyl-pyrimido[1,2-b]indazol-2-yl]phenyl}cyclo-butylamine | (300 MHz, dDMSO): δ 9.50 (s, 1H), 8.68 (d, 1H), 8.50 (d, 1H), 8.32 (d, 1H), 7.95 (dd, 2H), 7.81 (dd, 1H), 7.28-7.50 (m, 10H), 2.45 (s, 3H, completely obscured by the signal of the solvent), 2.23-2.42 (m, 2H), 1.89-2.12 (m, 3H), 1.52-1.70 (m, 1H). | RT = 1.08 min; m/z = 528 (ES+, M − NH$_2$) |
| 8-5 | 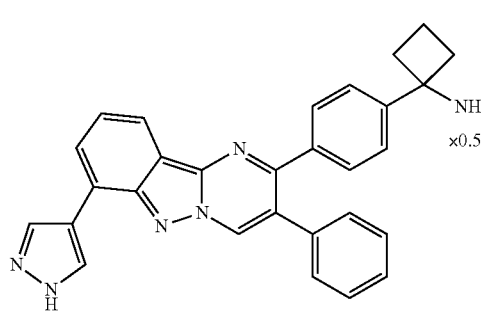 x0.5 eq HCOOH<br>1-{4-[3-Phenyl-7-(1H-pyrazol-4-yl)-pyrimido[1,2-b]indazol-2-yl]phenyl}-cyclobutylamine | (300 MHz, dDMSO): δ 9.49 (s, 1H), 8.45-8.68 (very br, 2H), (8.28 (s, 0.5 eq. HCOOH), 8.12 (d, 1H), 7.99 (d, 1H), 7.30-7.50 (m, 9H), 7.33 (dd, 1H), 2.28-2.45 (m, 2H), 2.04-2.20 (m, 2H), 1.89-2.04 (m, 1H), 1.55-1.73 (m, 1H). | RT = 0.90 min; m/z = 440 (ES+, M − NH$_2$) |

Example 9

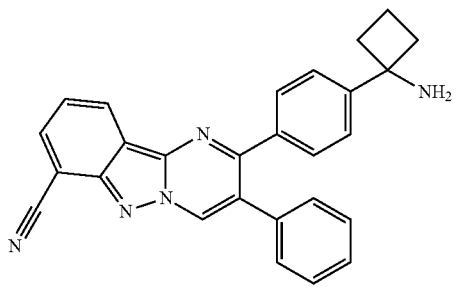 [SMILES: N#Cc1cccc2c1nn1cc(-c3ccccc3)c(-c3ccc(C4(N)CCC4)cc3)nc21]

2-[4-(1-Aminocyclobutyl)phenyl]-3-phenylpyrimido[1,2-b]indazole-7-carbonitrile 150 mg (0.26 mmol) {1-[4-(7-Bromo-3-phenylpyrimido[1,2-b]indazol-2-yl)phenyl]-cyclobutyl}carbamic acid tert-butyl ester (intermediate example Int-2-1), 1.7 mg (0.026 mmol) zinc, 21.6 mg (0.026 mmol) bis(diphenylphosphino)ferrocenedichloropalladium(II) and 61.8 mg (0.53 mmol) zinc cyanide in 2.2 mL N,N-dimethylacetamide, (degassed) were stirred in the microwave for four hours at 110° C. After addition of a further equivalent of zinc cyanide and a spatelspitze of zinc and bis(diphenylphosphino)ferrocenedichloropalladium(II) stirring was continued for three hours at 110° C. Despite an incomplete reaction the mixture was worked up. After addition of ethyl acetate the organic phase was washed twice with water and saturated ammonium chloride, dried over sodium sulfate, filtrated, and the solvent was removed. 274 mg {1-[4-(7-Cyano-3-phenylpyrimido[1,2-b]indazol-2-yl)-phenyl]cyclobutyl}carbamic acid tert-butylester were obtained which were used without purification in the next step (cleavage of the protecting group).

For that purpose the crude residue was stirred with 13.4 mL 4M hydrogen chloride in dioxane over night at room temperature. The solvent was evaporated and the residue was treated with saturated sodium bicarbonate. After extration with dichloromethane (trice) the combined organic phases were washed with brine, dried and filtrated. The solvent was evaporated and the residue was purified by HPLC yielding 28.9 mg of the title compound.

UPLC-MS: RT=1.06 min; m/z=399 (ES+, M-NH$_2$)

$^1$H-NMR (400 MHz, dDMSO): δ 9.63 (s, 1H), 8.62 (d, 1H), 8.23 (d, 1H), 7.30-7.48 (m, 10H), 2.25-2.39 (m, 2H), 2.20 (br., NH$_2$), 1.89-2.10 (m, 3H), 1.53-1.69 (m, 1H).

Example 10

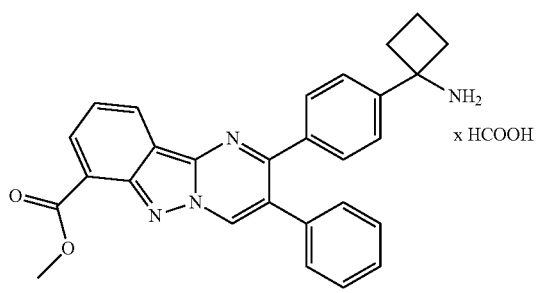 [SMILES: COC(=O)c1cccc2c1nn1cc(-c3ccccc3)c(-c3ccc(C4(N)CCC4)cc3)nc21]

x HCOOH

2-[4-(1-Aminocyclobutyl)phenyl]-3-phenylpyrimido
[1,2-b]indazole-7-carboxylic acid methyl ester
formiate 130 mg (0.23 mmol) {1-[4-(7-Bromo-3-phenylpyrimido [1,2-b]indazol-2-yl)phenyl]-cyclobutyl}carbamic acid tert-butyl ester (intermediate example Int-2-1), 0.028 mL (0.68 mmol) methanol, 60.3 mg (0.23 mmol) molybdenum hexacarbonyl, 6.6 mg (0.023 mmol) tri-tert-butylphosphine tetrafluoroborate, 104.2 mg (0.69 mmol) 1.8-diazabicyclo [5.4.0]undec-7-ene, and 17.3 mg (0.023 mmol) trans-bis-(acetato)-bis-[o-(di-o-tolylphosphino)benzyl]dipalladium (II) in 3 mL dimethyl acetamide (degassed) were stirred in the microwave for 30 min at 105° C. The reaction mixture was diluted with dichloromethane and the organic phase was washed with water and saturated ammonium chloride, dried over sodium sulfate and filtrated. After removal of the solvent 203 mg 2-[4-(tert-butoxycarbonylaminocyclobutyl)-phenyl]-3-phenylpyrimido[1,2-b]indazole-7-carboxylic acid methyl ester were obtained.

This crude residue (203 mg) was stirred with 15 mL 4M hydrogen chloride in dioxane over night at room temperature. The solvent was evaporated and the residue was treated with saturated sodium bicarbonate. After extraction with dichloromethane (trice) the combined organic phases were washed with brine, dried and filtrated. The solvent was evaporated and the residue was purified by HPLC yielding 42.7 mg of the title compound.

UPLC-MS: RT=0.97 min; m/z=449 (ES+, M+1)

$^1$H-NMR (300 MHz, dDMSO): δ 9.59 (s, 1H), 8.57 (d, 1H), 8.31 (d, 1H), 8.22 (s, 1H), 7.22-7.52 (m, 10H), 3.93 (s, 3H), 2.32-2.50 (m, partly obscured by the signal of the solvent, 2H), 2.15-2.32 (m, 2H), 1.92-2.12 (m, 1H), 1.59-1.79 (m, 1H).

2-[4-(1-Aminocyclobutyl)phenyl]-3-phenylpyrimido [1,2-b]indazol-7-ol 200 mg (0.35 mmol) {1-[4-(7-Bromo-3-phenylpyrimido [1,2-b]indazol-2-yl)phenyl]-cyclobutyl}carbamic acid tert-butyl ester (intermediate example Int-2-1), 98 mg (0.39 mmol) bis-(pinacolato)diboron, 103.4 mg (1.05 mmol) potassium acetate, 28.7 mg (0.035 mmol) bis(diphenylphosphino) ferrocenedichloropalladium(II) in two mL degassed tetrahydrofuran were heated in a microwave vial for three hours at 80° C. (heating block). Due to an incomplete reaction additional catalyst was added and heating was continued for four hours at 100° C. The reaction mixture was diluted with dichloromethane and the organic phase was washed with water, dried over sodium sulfate, filtrated, and the solvent was removed. 86 mg of 1-{4-[3-Phenyl-7-(4,4,5,5-tetramethyl-1,3,2-dioxaborolan-2-yl]pyrimido[1,2-b]indazol-2-yl] phenyl}cyclobutyl)carbamic acid tert-butyl ester were obtained.

86 mg Crude 1-{4-[3-phenyl-7-(4,4,5,5-tetramethyl-1,3,2-dioxaborolan-2-yl]-pyrimido[1,2-b]indazol-2-yl] phenyl}cyclobutyl)carbamic acid tert-butyl ester were dissolved in a mixture of tetrahydrofuran (3.9 mL), acetic acid (1.3 mL) and water (1.3 mL). After addition of 0.14 mL hydrogen peroxide the reaction mixture was stirred over night at room temperature. The reaction mixture was diluted with saturated sodium bicarbonate and ethyl acetate and vigorously stirred for 15 minutes. The organic phase was separated, washed with brine and dried over sodium sulfate. After filtration and evaporation of the solvent 68.4 mg of crude {1-[4-(7-hydroxy-3-phenylpyrimido[1,2-b]indazol-2-yl) phenyl]cyclobutyl}carbamic acid tert-butyl ester were obtained.

This crude residue was stirred with 2.3 mL 4M hydrogen chloride in dioxane over night at room temperature. The solvent was evaporated and the residue was treated with saturated sodium bicarbonate. After extraction with dichloromethane (trice) the combined organic phases were washed with brine, dried and filtrated. The solvent was evaporated and the residue was purified by HPLC yielding 12.6 mg of the title compound.

UPLC-MS: RT=0.82 min; m/z=390 (ES+, M-NH$_2$) Method C $^1$H-NMR (300 MHz, dDMSO): δ 9.35 (s, 1H), 8.83 (very br., 1H), 7.67 (d, 1H), 7.20-7.52 (m, 9H), 7.09 (dd, 1H), 6.90 (d, 1H), 2.28-2.45 (m, partly obscured by the signal of the solvent, 2H), 1.89-2.20 (m, 3H), 1.52-1.74 (m, 1H).

Example 11

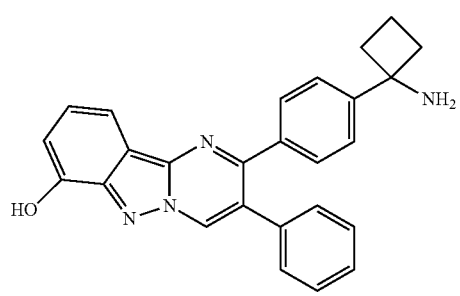 [SMILES: NC1(c2ccc(-c3nc4c5cccc(O)c5nn4cc3-c3ccccc3)cc2)CCC1]

Example 12

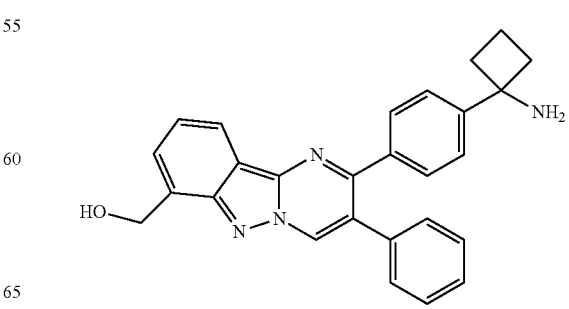

{2-[4-(1-Aminocyclobutyl)phenyl]-3-phenylpyrimido[1,2-b]indazol-7-yl}-methanol 135.7 mg (0.247 mmol) 2-[4-(tert-Butoxycarbonylaminocyclobutyl)phenyl]-3-phenylpyrimido[1,2-b]indazole-7-carboxylic acid methyl ester, described in example 10, were dissolved in 5 mL tetrahydrofuran. After addition of 18.8 mg (0.5 mmol) lithium aluminium hydride at −78° C., the reaction mixture was stirred was four hours. After addition of another equivalent lithium aluminium hydride stirring was continued for three hours at ° C. Stirring was further continued over night at room temperature. Additional four equivalents lithium aluminium hydride were added and the reaction mixture was stirred for 24 hours at room temperature. 96 mg {1-[4-(7-Hydroxymethyl-3-phenylpyrimido[1,2-b]indazol-2-yl)phenyl]-cyclobutyl}carbamic acid tert-butylester were stirred over night in 6 mL 4M hydrogen chloride in dioxane. The solvent was evaporated and the residue was treated with saturated sodium bicarbonate. After extraction with dichloromethane (trice) the combined organic phases were washed with brine, dried and filtrated. The solvent was evaporated and the residue was purified by HPLC yielding 2.3 mg of the title compound.

UPLC-MS: RT=0.85 min; m/z=404 (ES+, M-NH$_2$)

Example 13

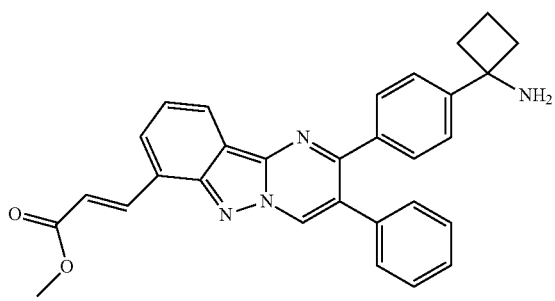 [SMILES: COC(=O)/C=C/c1cccc2c1nn1cc(-c3ccccc3)c(-c3ccc(C4(N)CCC4)cc3)nc21]

(E)-3-{2-[4-(1-Aminocyclobutyl)phenyl]-3-phenylpyrimido[1,2-b]indazol-7-yl}-acrylic acid methyl ester Step 1: (E)-3-{2-[4-(1-tert-butoxycarbonylaminocyclobutyl)phenyl]-3-phenyl-pyrimido[1,2-b]indazol-7-yl}acrylic acid methyl ester 200 mg (0.351 mmol) {1-[4-(7-Bromo-3-phenylpyrimido[1,2-b]indazol-2-yl)phenyl]-cyclobutyl}carbamic acid tert-butyl ester (intermediate example Int-2-1), 60.5 mg (0.7 mmol) acrylic acid methyl ester, 18.2 mg (0.06 mmol) tri-2-tolylphosphane and 7.9 mg (0.035 mmol) palladium(II) acetate were given in 2.47 mL degassed acetonitrile. After addition of 40.5 mg (0.4 mmol) triethylamine the reaction mixture was stirred in the microwave for one hour at 110° C. Due to an incomplete reaction additional acrylic acid methyl ester (30 mg) and catalyst (4 mg) were added and stirring was continued for two hours at 110° C. The reaction mixture was poured on a mixture of water (10 mL), saturated ammonium chloride (60 mL) and dichloromethane (150 mL). After vigorous stirring the organic phase was separated and the water phase was reextracted with dichloromethane (50 mL). The combined organic extracts were washed with brine and dried (sodium sulfate). After removal of the solvent the crude product (275 mg, >100%) was used in the next step without further purification.

UPLC-MS: RT=1.70 min; m/z=575 (ES+, M+1)

Step 2: (E)-3-{2-[4-(1-Aminocyclobutyl)phenyl]-3-phenylpyrimido[1,2-b]indazol-7-yl}acrylic acid methyl ester 275 mg of the crude (E)-3-{2-[4-(1-tert-Butoxycarbonylaminocyclobutyl)phenyl]-3-phenylpyrimido[1,2-b]indazol-7-yl}acrylic acid methyl ester were stirred in 15 mL 4M hydrogen chloride in dioxane for 18 hours at room temperature. The solvent was evaporated and the residue was stirred with saturated sodium bicarbonate for one hour at room temperature. After addition of dichloromethane stirring was continued for another hour. The organic phase was separated and the aqueous phase was extracted once more with dichloromethane. The combined organic extracts were washed with water and brine, dried and filtrated. The solvent was evaporated and the residue purified by HPLC 35.7 mg (15.7%) of the title compound.

UPLC-MS: RT=1.12 min; m/z=458 (ES+, M-NH$_2$) (300 MHz, CD$_3$OD): δ 9.32 (s, 1H), 8.41 (d, 1H), 8.05 (d, 1H), 7.82 (d, 1H), 7.61 (d, 1H), 7.54 (d, 2H), 7.30-7.49 (m, 8H), 3.82 (s, 3H), 2.48-2.63 (m, 2H), 2.19-2.38 (m, 2H), 1.98-2.18 (m, 1H), 1.69-1.89 (m, 1H).

Example 14

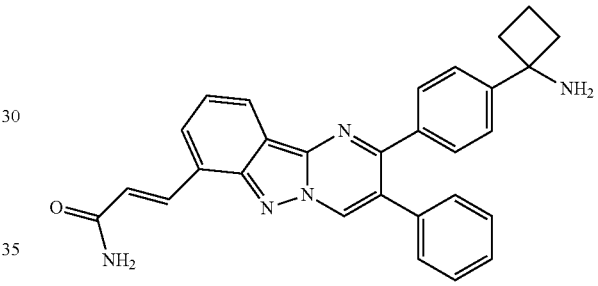

(E)-3-{2-[4-(1-Aminocyclobutyl)phenyl]-3-phenylpyrimido[1,2-b]indazol-7-yl}-acrylamide Step 1: (E)-3-[2-(4-{1-[(tert-Butoxycarbonyl)amino]cyclobutyl}phenyl)-3-phenyl-pyrimido[1,2-b]indazol-7-yl]acrylamide 200 mg (0.351 mmol) {1-[4-(7-Bromo-3-phenylpyrimido[1,2-b]indazol-2-yl)phenyl]-cyclobutyl}carbamic acid tert-butyl ester (intermediate example Int-2-1), 49.9 mg (0.7 mmol) acrylamide, 18.2 mg (0.06 mmol) tri-2-tolylphosphane and 7.9 mg (0.035 mmol) palladium(II) acetate were treated in 2.47 mL degassed acetonitrile as described in example 13 (step 1). After the work-up 281 mg (>100%) of the crude product were obtained and used in the next step without further purification.

UPLC-MS: RT=1.42 min; m/z=560 (ES+, M+1)

Step 2: (E)-3-{2-[4-(1-Aminocyclobutyl)phenyl]-3-phenylpyrimido[1,2-b]indazol-7-yl}acrylamide 281 mg of the crude (E)-3-[2-(4-{1-[(tert-Butoxycarbonyl)amino]cyclobutyl}phenyl)-3-phenyl-pyrimido[1,2-b]indazol-7-yl]acrylamide were stirred in 15.9 mL 4M hydrogen chloride in dioxane for 18 hours at room temperature as described in example 13 (step 2). After the usual work-up and purification by HPLC 28.5 mg (12.4%) of the title compound were obtained.

UPLC-MS: RT=0.82 min; m/z=460 (ES+, M+1) (300 MHz, CD$_3$OD): δ 9.22 (s, 1H), 8.33 (d, 1H), 7.92 (d, 1H), 7.75 (d, 1H), 7.71 (d, 1H), 7.51 (d, 2H), 7.23-7.48 (m, 10H), 2.45-2.63 (m, 2H), 2.19-2.32 (m, 2H), 1.98-2.18 (m, 1H), 1.69-1.84 (m, 1H).

Example 15-0

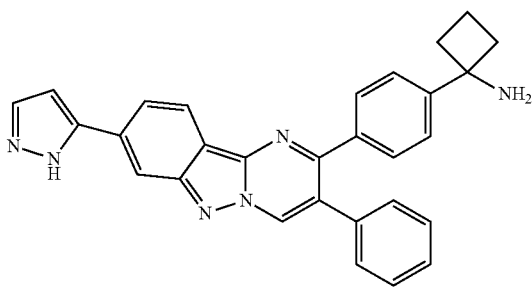 [SMILES: NC1(c2ccc(-c3nc4c5ccc(-c6ccn[nH]6)cc5nn4cc3-c3ccccc3)cc2)CCC1]

1-{4-[3-Phenyl-8-(1H-pyrazol-5-yl)pyrimido[1,2-b]indazol-2-yl]phenyl}-cyclobutylamine 206.7 mg Crude 5-[2-(4-{1-[(tert-butoxycarbonyl)amino]cyclobutyl}phenyl)-3-phenylpyrimido[1,2-b]indazol-8-yl]pyrazole-1-carboxylic acid tert-butyl ester, intermediate example Int-3-0, were dissolved in 15 mL 4 M hydrogen chloride in dioxane. The reaction mixture was stirred over night at room temperature. After evaporation of the solvent the residue was dissolved in methanol and given on a PoraPak Rxn CX column. The column was washed with 100 mL methanol, and the product was eluted with methanol/ammonia. The solvent was removed, and the residue was purified by HPLC yielding 32.8 mg of the title compound.

UPLC-MS: RT=0.91 min; m/z=440 (ES+, M-NH$_2$)

$^1$H-NMR (300 MHz, dDMSO): δ 13.00 (br., 1H), 9.40 (1H), 8.28 (d, 1H), 8.21 (1H), 7.72-7.92 (very br., 2H), 7.25-7.48 (m, 9H), 6.92 (1H), 2.20-2.40 (m, 2H), 1.89-2.10 (m, 3H), 1.53-1.68 (m, 1H). The following examples had been prepared in analogy according to example 15-0 by cleaving the protecting group in the corresponding intermediate examples and subsequent purification.

| Example | Structure/Name | 1H-NMR | UPLC-MS resp. MS |
|---|---|---|---|
| 15-1 | 1-{4-[8-(3-Methyl-1H-pyrazol-5-yl)-3-phenylpyrimido[1,2-b]indazol-2-yl]phenyl}-cyclobutylamine | (300 MHz, dDMSO): δ 12.69 (br., 1H), 9.40 (1H), 8.26 (d, 1H), 8.12 (1H), 7.79 (very br., 1H), 7.25-7.50 (m, 9H), 6.65 (1H), 2.19-2.42 (m, 5H), 1.89-2.12 (m, 3H), 1.53-1.70 (m, 1H). | RT = 0.96 min; m/z = 454 (ES+, M − NH$_2$) |
| 15-2 | 1-{4-[3-Phenyl-9-(1H-pyrazol-5-yl)-pyrimido[1,2-b]indazol-2-yl]phenyl}-cyclobutylamine | (300 MHz, dDMSO): δ 9.42 (1H), 8.62 (1H), 8.23 (1H), 8.18 (d, 1H), 7.88 (d, 1H), 7.72 (1H), 7.29-7.52 (m, 9H), 6.89 (1H), 2.29-2.48 (m, partly obscured by the signal of the solvent, 2H), 2.10-2.29 (m, 2H), 1.90-2.10 (m, 1H), 1.58-1.78 (m, 1H). | RT= 1.32 min; m/z = 457 (ES+, M+1) |

| Example | Structure/Name | 1H-NMR | UPLC-MS resp. MS |
|---|---|---|---|
| 15-3 | 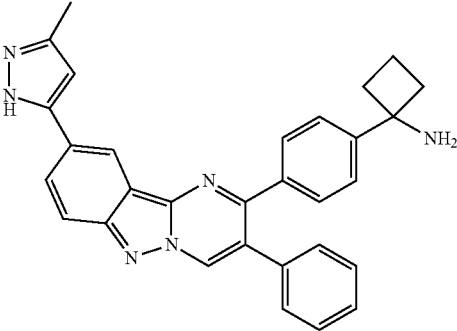<br>1-{4-[9-(3-Methyl-1H-pyrazol-5-yl)-3-phenylpyrimido[1,2-b]indazol-2-yl]phenyl}-cyclobutylamine | (300 MHz, dDMSO): δ 12.55 (br., 1H), 9.41 (1H), 8.58 (br., 1H), 8.11 (very br., 1H), 7.82 (d, 1H), 7.21-7.48 (m, 9H), 6.59 (1H), 2.09-2.42 (m, 5H), 1.88-2.12 (m, 3H), 1.51-1.70 (m, 1H). | RT= 1.35 min; m/z = 471 (ES+, M+1) |
| 15-4 | 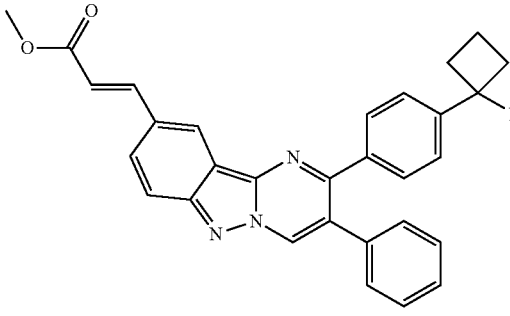<br>(E)-3-{2-[4-(1-Aminocyclobutyl)phenyl]-3-phenylpyrimido[1,2-b]indazol-9-yl}acrylic acid methyl ester | (300 MHz, dDMSO): δ 9.47 (s, 1H), 8.58 (1H), 8.08 (d, 1H), 7.89 (d, 1H), 7.83 (d, 1H), 7.20-7.48 (m, 9H), 6.68 (d, 1H), 3.73 (s, 3H), 2.25-2.42 (m, 2H), 1.88-2.18 (m, 3H), 1.53-1.73 (m, 1H). | RT= 1.09 min; m/z = 458 (ES+, M-NH$_2$) |
| 15-5 | 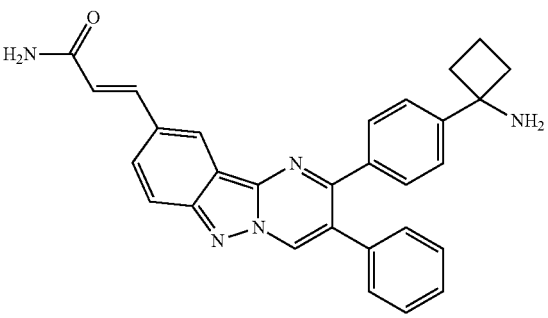<br>(E)-3-{2-[4-(1-Aminocyclobutyl)phenyl]-3-phenylpyrimido[1,2-b]indazol-9-yl}-acrylamide | (300 MHz, dDMSO): δ 9.48 (s, 1H), 8.40 (1H), 7.78-7.91 (m, 2H), 7.62 (d, 1H), 7.28-7.52 (m, 10H), 7.08 (1H), 6.68 (d, 1H), 2.22-2.40 (m, 2H), 2.15 (very br., 2H); 1.86-2.12 (m, 3H), 1.52-1.70 (m, 1H). | RT = 0.89 min; m/z = 460 (ES+, M + 1) |

Biological Investigations

The following assays can be used to illustrate the commercial utility of the compounds according to the present invention.

Biological Assay 1.0: Akt1 Kinase Assay

Akt1 inhibitory activity of compounds of the present invention was quantified employing the Akt1 TR-FRET assay as described in the following paragraphs.

His-tagged human recombinant kinase full-length Akt1 expressed in insect cells was purchased form Invitrogen (part number PV 3599). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 μl of a solution of Akt1 in assay buffer [50 mM TRIS/HCl pH 7.5, 5 mM MgCl$_2$, 1 mM dithiothreitol, 0.02% (v/v) Triton X-100 (Sigma)] were added and the mixture was incubated for 15 min at 22° C. to allow prebinding of the test compounds to the enzyme before the start of the kinase reaction. Then the kinase reaction was started by the addition of 3 μl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt1 in the assay was adjusted depending of the activity of the enzyme lot and was chosen appropriate to have the assay in the linear range, typical enzyme concentrations were in the range of about 0.05 ng/µl (final conc. in the 5 µl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Biological Assay 2.0: Akt2 Kinase Assay

Akt2 inhibitory activity of compounds of the present invention was quantified employing the Akt2 TR-FRET assay as described in the following paragraphs.

His-tagged human recombinant kinase full-length Akt2 expressed in insect cells and activated by PDK1 was purchased form Invitrogen (part number PV 3975). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Akt2 in assay buffer [50 mM TRIS/HCl pH 7.5, 5 mM $MgCl_2$, 1 mM dithiothreitol, 0.02% (v/v) Triton X-100 (Sigma)] were added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt2 in the assay was adjusted depending of the activity of the enzyme lot and was chosen appropriate to have the assay in the linear range, typical enzyme concentrations were in the range of about 0.2 ng/µl (final conc. in the 5 µl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Preferred compounds of the present invention show in either the Akt1 or Akt2 kinase assay: median $IC_{50}$<5 µM, more preferably, median $IC_{50}$<0.5 µM, even more preferably, median $IC_{50}$≤0.1 µM.

The following Table I gives data for the Examples of the present invention.

| Example | $IC_{50}$ Akt1, µM |
|---|---|
| 1 | 0.093 |
| 2 | 0.528 |
| 3 | 2.630 |
| 4 | 0.140 |
| 4.1 | 0.059 |
| 4.2 | 0.229 |
| 4.3 | 0.087 |
| 4.4 | 0.043 |
| 4.5 | 0.035 |
| 4.6 | 0.458 |
| 4.7 | 0.025 |
| 4.8 | 0.111 |
| 4.9 | 0.016 |
| 4.10 | 0.021 |
| 4.11 | 0.017 |
| 4.12 | 0.014 |
| 4.13 | 0.023 |
| 5 | 0.110 |
| 5.1 | 0.120 |
| 5.2 | 0.130 |
| 6 | 0.067 |
| 6.1 | 0.041 |
| 6.2 | 0.097 |
| 6.3 | 0.016 |
| 6.4 | 0.018 |
| 6.5 | 0.031 |
| 6.6 | 0.010 |
| 6.7 | 0.019 |
| 7 | 0.320 |
| 8 | 10 |

-continued

| Example | IC$_{50}$ Akt1, µM |
|---|---|
| 8.1 | 0.170 |
| 8.2 | 5.6 |
| 8.3 | 0.720 |
| 8.4 | 17 |
| 8.5 | 0.160 |
| 9 | 0.049 |
| 10 | 0.740 |
| 11 | 0.100 |
| 14 | 0.580 |
| 15.0 | 0.015 |
| 15.1 | 0.010 |
| 15.2 | 0.010 |
| 15.3 | 0.006 |
| 15.4 | 0.010 |
| 15.5 | 0.030 |

Cellular Assays 3.0: p-AKT1/2/3-S473, -T308, and p-4E-BP1-T70 Assays

The molecular mechanism of action was investigated in a set of experiments to assess the inhibition of the PI3K-AKT-mTOR pathway in responsive cell lines such as KPL4 breast tumour cell line (PIK3CAH1047R, HER2O/E and hormone independent). The phospho-substrates of PI3K-AKT-mTOR axis were used as the read-outs to reflect pathway inhibition. Cells were seeded at 60-80% confluency per well in 96-well cell culture plates. After overnight incubation at 37° C. 5% $CO_2$, cells were treated with compounds and vehicle at 37° C. for 2 hours. Thereafter, cells were lysed in 150 µl lysis buffer and the levels of phospho-AKT at T308 and S473 and p-4E-BP1 at T70 sites were determined with the corresponding AlphaScreen® SureFire® assay kits (Perkin Elmer: 4E-BP1 Assay Kit Cat # TRG4E2S10K; Akt 1/2/3 p-Ser 473 #TGRA4S500 and Akt 1/2/3 p-Thr 308 #TGRA3S500 as well as IgG detection Kit #6760617M) as described in the manuals. All measurements where at least done in duplicates and confirmed by independent repetition.

Alternatively pAKT-S473 was measured using the "Akt Duplex" of the MULTI-SPOT® Assay System (Fa. Meso Scale Discovery, Cat #N41100B-1) following manufacturers instructions. Each assay used 20 µg of protein extract and measured total AKT and p-AKT content simultaneously in one well. All measurements where at least done in duplicates and confirmed by independent repetition. Values for P-AKT are expressed as percentage of P-AKT level compared to total-AKT content of the extracts.

Biological Assay 4.0: Tumor Cell Proliferation Assays

Compounds were tested in a cell-based assay that measures the capacity of the compounds to inhibit tumour cell proliferation following a 72 h drug exposure. Cell viability is determined using CellTiter-Glow® (CTG, Promega, cat #G7571/2/3). The CellTiter-Glo® Luminescent Cell Viability Assay is a homogeneous method to determine the number of viable cells in culture. Detection is based on using the luciferase reaction to measure the amount of ATP from viable cells. The amount of ATP in cells correlates with cell viability. Within minutes after a loss of membrane integrity, cells lose the ability to synthesize ATP, and endogenous ATPases destroy any remaining ATP; thus the levels of ATP fall precipitously.

Cells were plated at 3000-5000 cells/well (depending on the cell lines) in 90 µL growth medium on MTPs (Corning; #3603, black plate, clear flat bottom). For each cell line assayed, cells were plated onto a separate plate for determination of fluorescence at t=0 hour and t=72 hour time points. Following overnight incubation at 37° C., chemiluminescence values for the t=0 samples were determined after adding 10 µl medium and 100 µl CTG solution according to manufacture protocol. Plates for the t=72 hour time points were treated with compounds diluted into growth medium at ten times final concentration added in 10 µL to the cell culture plate. Cells were then incubated for 72 hours at 37° C. Chemiluminescence values for the t=72 hour samples were determined. For data analysis, briefly, data from 24 h plate where used to reflect 100% inhibition of growth ("Ci") and DMSO control for uninhibited growth ("CO") and analyzed using MTS software package for IC$_{50}$ and Hill coefficient. Experiments were controlled using a reference compound as standard.

Example 5.0

In Vivo Rat Pharmacokinetics

For in vivo pharmacokinetic experiments test compounds were administered to male Wistar rats intravenously at doses of 0.3 to 1 mg and intragastral at doses of 0.6 to 10 mg/kg formulated as solutions using solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). For pharmacokinetics after intragastral administration test compounds were given intragastral to fasted rats and blood samples were taken at 5 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparintubes (Monovetten®, Sarstedt) and centrifuged for 15 min at 3000 rpm. An aliquot of 100 µL from the supernatant (plasma) was taken and precipitated by addition of 400 µL cold acetonitrile and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood. PK parameters calculated from concentration time profiles after i.g.: Cmax: Maximal plasma concentration (in mg/L); Cmaxnorm: Cmax divided by the administered dose (in kg/L); Tmax: Time point at which Cmax was observed (in h). Parameters calculated from both, i.v. and i.g. concentration-time profiles: AUC-norm: Area under the concentration-time curve from t=0 h to infinity (extrapolated) divided by the administered dose (in kg*h/L); AUC(0-tlast)norm: Area under the concentration-time curve from t=0 h to the last time point for which plasma concentrations could be measured divided by the administered dose (in kg*h/L); t½: terminal half-life (in h); F: oral bioavailability: AUCnorm after intragastral administration divided by AUCnorm after intravenous administration (in %).

The person skilled in the art will be aware of methods to show in vivo efficacy of anti-cancer compounds. By way of illustration, the following example describes methods of quantifying the in vivo efficacy in a mouse xenograft model.

The skilled person will be able to apply such principles to derive models from alternative tumor material.

Example 6.0

In Vivo Xenograft Mechanism of Action Study

To demonstrate that compounds act in tumours by the anticipated mode of action phosphorylation of the AKT protein was investigated in PC3 prostate tumours treated once with 50 mg/kg compound.

To this extent PC3 human prostate tumours were xenografted onto athymic nude mice. PC3 tumour cells were cultivated according to ATCC protocols in recommended media contained 10% FCS and harvested for transplantation in a subconfluent (70%) state. $3 \times 10^6$ tumour cells suspended in 50% Matrigel were subcutaneously implanted into the inguinal region of male mice. Tumours were allowed to grow to the predetermined size of 60-80 mm². When the tumours were approximately in size, the animals were randomized to treatment and control groups (groups size: 9 animals) and treatment was started. Animals were treated once with 50 mg/kg compound or vehicle per oral administration (p.o.) carried out via a gastric tube. Treatment of each animal was based on individual body weight. At 2, 5 and 24 hours post treatment 3 animals each were sacrificed and the PC3 tumours excised. Tumour samples of approximately 5×5×5 mm were lysed on ice in MSD lysis buffer in the presence of protease and phosphatase inhibitors using Tissue Lyzer (Qiagen, Germany). The levels of p-AKT S473 in extracts from tumour tissue were analysed in an ELISA based assay. This assay is based on the "Akt Duplex" of the MULTI-SPOT® Assay System (Fa. Meso Scale Discovery, Cat #N41100B-1) following manufacturers instructions. Each assay used 20 μg of protein extract and measured total AKT and p-AKT content simultaneously in one well. All measurements where at least done in duplicates and confirmed by independent repetition.

Values for P-AKT are expressed as percentage of P-AKT level compared to total-AKT content of the extracts. Vehicle treated tumours were analyzed to determine the basal level of P-AKT in this model and used as a normalization control to determine the % P-AKT relative to vehicle levels.

Example 6.1

In Vivo Xenograft Efficacy Study

To determine the therapeutic efficacy and tolerability of compounds, tumour growth of PC3 prostate tumours xenografted onto nude mice may be observed. Mice were treated either with vehicle or compounds.

To this extent PC3 xenografts were established as described above. Tumours were allowed to grow to the predetermined size of 25-35 mm². When the tumours were approximately in size, the animals were randomized to treatment and control groups (groups size: 8 animals) and treatment was started. Treatment of each animal was based on individual body weight and oral administration (p.o.) was carried out via a gastric tube. The oral application volumes were 10 ml/kg for mice. Mice were treated once daily with 50 mg/kg compounds.

Tumour response was assessed by determination of the tumour area (product of the longest diameter and its perpendicular) using a calliper. The animal body weight was monitored as a measure for treatment-related toxicity. Measurement of tumour area and body weight were performed 2-3 times weekly. Statistical analysis was assessed using the SigmaStat software. A one way analysis of variance was performed, and differences to the control were compared by a pair-wise comparison procedure (Dunn's method). T/C ratios (Treatment/Control) were calculated with final tumour weights at study end.

The invention claimed is:
1. A compound of formula (I)

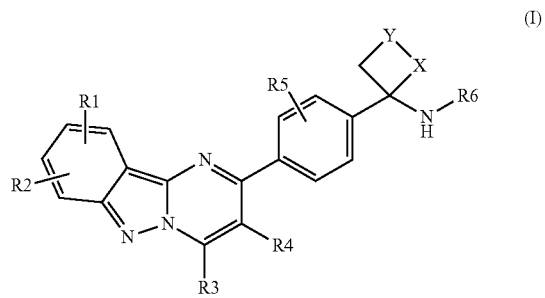

wherein
R1 hydrogen, halogen, cyano, hydroxy, COO(1-6C-alkyl), COOH,
  1-6Calkyl,
    which is optionally substituted with hydroxy,
  (2-6Calkenyl)
    which is optionally substituted with COO(1-6Calkyl) or (CO)NR7R8, aryl, whereby the aryl ring is optionally substituted one or two times independently by a group selected from halogen, cyano, hydroxy, 1-6C-alkoxy, —SO2-(1-6C-alkyl), —SO2-NR7R8, 1-6 C-alkyl, (1-6C-alkylen)OH, COO(1-6C-alkyl), COOH, (CO)NR7R8, heteroaryl,
    whereby the heteroaryl ring is optionally substituted by 1-3C-alkyl, hydroxy, COO(1-6Calkyl),
R2 is hydrogen, halogen, 1-4Calkyl, 1-4Calkoxy, OCF₃, NO₂,
R3 is hydrogen, NH(3-7C-cycloalkyl), NH(1-6C-alkyl),
R4 is phenyl optionally substituted by 1-6C-alkyl, halogen, cyano,
R5 is hydrogen, halogen,
X is —CH₂—,
Y is —CH₂—, —CH(OH)—,
R6 is hydrogen, COO(1-6C-alkyl),
R7, R8 can be the same or different, is hydrogen, 1-6C-alkyl (optionally substituted independently one or more times with a group selected from halogen, hydroxy, mono- or di-1-6C-alkylamino), 1-6C-alkoxy, or 3-7C-cycloalkyl, or,
  in the case of —NR7R8, R7 and R8 together with the nitrogen to which they are attached may also form a 3-6C-heterocyclic ring,
or an N-oxide, a salt, a tautomer or a stereoisomer of said compound, or a salt of said N-oxide, tautomer or stereoisomer.

2. A compound of formula I according to claim 1 wherein
R1 is halogen, cyano, hydroxy, COOH, COO(1-4C-alkyl), (1-4Calkyl),
  which is optionally substituted with hydroxy,
(2-4Calkenyl)
  which is optionally substituted with COO(1-4Calkyl) or (CO)NR7R8, phenyl, whereby the phenyl ring is optionally substituted one or two times independently by
a group selected from halogen, cyano, hydroxy, 1-4C-alkoxy, (1-4C-alkyl)-S02, 1-4C-alkyl, hydroxy(l-4C-alkyl), COO(1-4C-alkyl), (CO)NR7R8, heteroaryl,
whereby the heteroaryl group is optinally substituted by 1-3C-alkyl, hydroxy or COO(1-4Calkyl),
R2 is hydrogen,
R3 is hydrogen, NH(3-6C-cycloalkyl), NH(1-4C-alkyl),
R4 is phenyl,
R5 is hydrogen,
X is —CH$_2$—,
Y is —CH2-, —CH(OH)—,
R6 is hydrogen, COO(1-4C-alkyl),
R7, R8 can be the same or different, is hydrogen, 1-4C-alkyl (optionally substituted independently one or more times with a group selected from halogen, hydroxy, mono- or di-1-4C-alkylamino), 1-4C-alkoxy, or 3-7C-cycloalkyl, or,
in the case of —NR7R8, R7 and R8 together with the nitrogen to which they are attached may also form a 3-6C-heterocyclic ring,
or an N-oxide, a salt, a tautomer or a stereoisomer of said compound, or a salt of said N-oxide, tautomer or stereoisomer.

3. A compound of formula I according to claim 1 wherein
R1 F, Br, cyano, hydroxy, COOCH3, CH2OH, —C2H2-COOCH3, —C2H2-CONH2, —CH=CH—(CO)—OCH3, —CH=CH—(CO)—NH2,
1H-pyrazol-4-yl, 1H-pyrazol-5-yl, 3-pyridyl,
whereby the pyrazole and pyridinyl group is optionally substituted by methyl, hydroxy or COOCH3, phenyl,
whereby the phenyl ring is substituted one or two times independently by a group selected from F, cyano, hydroxy, methoxy, SO2CH3, SO2NH2, methyl, CH2OH, COOCH3, CONH2,
R2 hydrogen,
R3 hydrogen, NH(cyclopropyl), NHCH3,
R4 phenyl,
R5 hydrogen,
X is —CH$_2$—,
Y is —CH$_2$—,
R6 hydrogen, COOC(CH3)3,
or an N-oxide, a salt, a tautomer or a stereoisomer of said compound, or a salt of said N-oxide, tautomer or stereoisomer.

4. Compounds of formula (I) according to claim 1, which is selected from the group consisting of
1-[4-(9-Fluoro-3-phenylpyrimido[1,2-b]indazol-2-yl)phenyl]cyclobutylamine;
2-[4-(1-Aminocyclobutyl)phenyl]-N-cyclopropyl-9-fluoro-3-phenylpyrimido[1,2-b]indazol-4-amine;
2-[4-(1-Aminocyclobutyl)phenyl]-N-methyl-9-fluoro-3-phenylpyrimido[1,2-b]indazol-4-amine;
3-{2-[4-(1-Aminocyclobutyl)phenyl]-3-phenyl-pyrimido[1,2-b]indazol-8-yl}benzonitrile;
1-{4-[8-(4-Mesylphenyl)-3-phenylpyrimido[1,2-b]indazol-2-yl]-phenyl}cyclobutylamine;
1-{4-[8-(4-Fluorophenyl)-3-phenylpyrimido[1,2-b]indazol-2-yl]-phenyl}cyclobutylamine;
1-[4-(8-Bromo-3-phenylpyrimido[1,2-b]indazol-2-yl)phenyl]cyclobutylamine hydrochloride;
5-{2-[4-(1-Aminocyclobutyl)phenyl]-3-phenylpyrimido[1,2-b]indazol-8-yl}-2-fluorobenzyl alcohol;
5-{2-[4-(1-Aminocyclobutyl)phenyl]-3-phenylpyrimido[1,2-b]indazol-8-yl}-2-fluorophenol formiate;
1-{4-[8-(4-Fluoro-3-methoxyphenyl)-3-phenylpyrimido[1,2-b]indazol-2-yl]phenyl}cyclobutylamine;
1-{4-[8-(3-Mesylphenyl)-3-phenylpyrimido[1,2-b]indazol-2-yl]phenyl}cyclobutylamine formiate;
2-[4-(1-Aminocyclobutyl)phenyl]-3-phenylpyrimido[1,2-b]indazole-8-carboxylic acid methyl ester;
3-{2-[4-(1-Aminocyclobutyl)phenyl]-3-phenylpyrimido[1,2-b]indazol-8-yl}benzamide;
4-{2-[4-(1-Aminocyclobutyl)phenyl]-3-phenylpyrimido[1,2-b]indazol-8-yl}benzamide;
1-{4-[3-Phenyl-8-(1H-pyrazol-4-yl)pyrimido[1,2-b]indazol-2-yl]-phenyl}cyclobutylamine;
5-{2-[4-(1-Aminocyclobutyl)phenyl]3-phenylpyrimido[1,2-b]indazol-8-yl}pyridin-2-ol;
5-{2-[4-(1-Aminocyclobutyl)phenyl]-3-phenylpyrimido[1,2-b]indazol-8-yl}pyridine-2-carboxylic acid methyl ester;
1-{4-[9-(4-Fluorophenyl)-3-phenylpyrimido[1,2-b]indazol-2-yl]phenyl}-cyclobutylamine;
1-[4-(3-Phenyl-9-p-tolylpyrimido[1,2-b]indazol-2-yl)phenyl]cyclobutylamine;
3-{2-[4-(1-Aminocyclobutyl)phenyl]-3-phenylpyrimido[1,2-b]indazol-9-yl}benzoic acid methyl ester;
3-{2-[4-(1-Aminocyclobutyl)phenyl]-3-phenylpyrimido[1,2-b]indazol-9-yl}benzonitrile;
1-[4-(9-Bromo-3-phenylpyrimido[1,2-b]indazol-2-yl)phenyl]cyclobutylamine;
4-{2-[4-(1-Aminocyclobutyl)phenyl]-3-phenylpyrimido[1,2-b]indazol-9-yl}benzonitrile formiate;
3-{2-[4-(1-Aminocyclobutyl)phenyl]-3-phenylpyrimido[1,2-b]indazol-9-yl}benzyl alcohol formiate;
4-{2-[4-(1-Aminocyclobutyl)phenyl]-3-phenylpyrimido[1,2-b]indazol-9-yl}benzyl alcohol formiate;
4-{2-[4-(1-Aminocyclobutyl)phenyl]-3-phenylpyrimido[1,2-b]indazol-9-yl}benzenesulfonamide formiate;
5-{2-[4-(1-Aminocyclobutyl)phenyl]-3-phenylpyrimido[1,2-b]indazol-9-yl}-2-fluorobenzyl alcohol;
1-{4-[3-Phenyl-9-(1H-pyrazol-4-yl)pyrimido[1,2-b]indazol-2-yl]phenyl}-cyclobutylamine;
4-{2-[4-(1-Aminocyclobutyl)phenyl]-3-phenylpyrimido[1,2-b]indazol-10-yl}benzonitrile formiate;
1-[4-(3-Phenyl-10-p-tolylpyrimido[1,2-b]indazol-2-yl)phenyl]cyclobutylamine x 0.5 formiate;
1-{4-[10-(4-Fluorophenyl)-3-phenylpyrimido[1,2-b]indazol-2-yl]-phenyl}cyclobutylamine formiate;
4-{2-[4-(1-Aminocyclobutyl)phenyl]-3-phenylpyrimido[1,2-b]indazol-10-yl}benzyl alcohol formiate;
3-{2-[4-(1-Aminocyclobutyl)phenyl]-3-phenylpyrimido[1,2-b]indazol-7-yl}benzonitrile;
1-[4-(7-Bromo-3-phenylpyrimido[1,2-b]indazol-2-yl)phenyl]cyclobutylamine hydrochloride;
1-{4-[7-(4-Fluorophenyl)-3-phenylpyrimido[1,2-b]indazol-2-yl]-phenyl}cyclobutylamine;
4-{2-[4-(1-Aminocyclobutyl)phenyl]-3-phenylpyrimido[1,2-b]indazol-7-yl}benzyl alcohol formiate;
1-{4-[7-(3-Mesylphenyl)-3-phenylpyrimido[1,2-b]indazol-2-yl]-phenyl}cyclobutylamine;
1-{4-[3-Phenyl-7-(1H-pyrazol-4-yl)pyrimido[1,2-b]indazol-2-yl]-phenyl}cyclobutylamine×0.5 formiate;
2-[4-(1-Aminocyclobutyl)phenyl]-3-phenylpyrimido[1,2-b]indazole-7-carbonitrile;
2-[4-(1-Aminocyclobutyl)phenyl]-3-phenylpyrimido[1,2-b]indazole-7-carboxylic acid methyl ester formiate;
2-[4-(1-Aminocyclobutyl)phenyl]-3-phenylpyrimido[1,2-b]indazol-7-ol;

{2-[4-(1-Aminocyclobutyl)phenyl]-3-phenylpyrimido[1,2-b]indazol-7-yl}methanol;

(E)-3-{2-[4-(1-Aminocyclobutyl)phenyl]-3-phenylpyrimido[1,2-b]indazol-7-yl}acrylic acid methyl ester;

(E)-3-{2-[4-(1-Aminocyclobutyl)phenyl]-3-phenylpyrimido[1,2-b]indazol-7-yl}acrylamide;

1-{4-[3-Phenyl-8-(1H-pyrazol-5-yl)-pyrimido[1,2-b]indazol-2-yl]-phenyl}cyclobutylamine;

1-{4-[8-(3-Methyl-1H-pyrazol-5-yl)-3-phenylpyrimido[1,2-b]indazol-2-yl]phenyl}56 cyclobutylamine;

1-{4-[3-Phenyl-9-(1H-pyrazol-5-yl)pyrimido[1,2-b]indazol-2-yl]-phenyl}cyclobutylamine;

1-{4-[9-(3-Methyl-1H-pyrazol-5-yl)-3-phenylpyrimido[1,2-b]indazol-2-yl]phenyl}cyclobutylamine;

(E)-3-{2-[4-(1-Aminocyclobutyl)phenyl]-3-phenylpyrimido[1,2-b]indazol-9-yl}acrylic acid methyl ester; and (E)-3-{2-[4-(1-Aminocyclobutyl)phenyl]-3-phenylpyrimido[1,2-b]indazol-9-yl}acrylamide.

5. Process for the manufacture of compounds of general formula (I) according to claim 1, characterized in that a compound of formula (III)

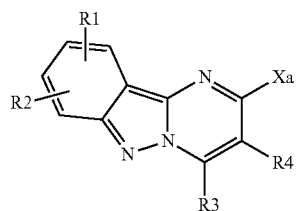

wherein R1, R2, R3 and R4 have the meaning as defined in claim 1 and Xa is a leaving group, is reacted with a compound of general formula (IV)

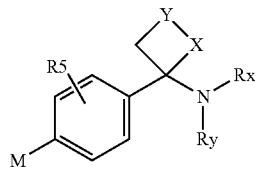

wherein R5, X and Y have the meaning as defined in claim 1,

M is —B(OH)2, —Sn(1-4C-alkyl)3, —ZnCl, —ZnBr, —ZnI, or,

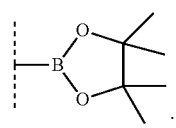

Rx is R6 or a protecting group, wherein R6 has the meaning as defined in claim 1, Ry is hydrogen or a protecting group or Rx and Ry together form a cyclic protecting group, forming a compound of general formula (II)

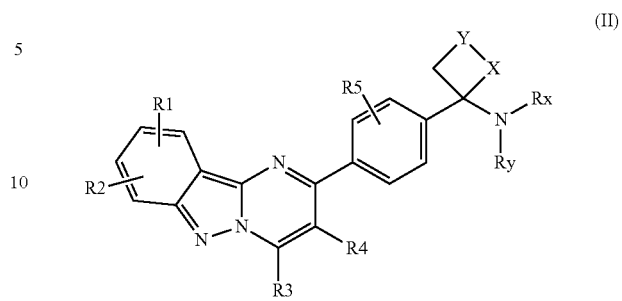

which is subsequently optionally deprotected to form a compound of general formula (I)

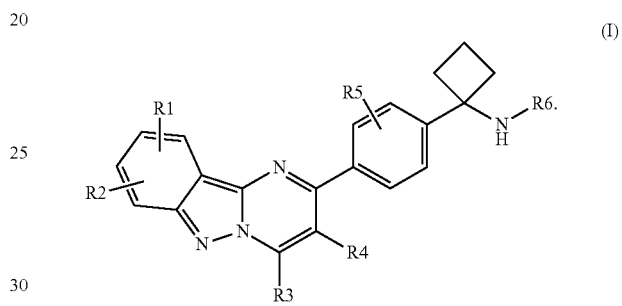

6. Intermediates of formula (II)

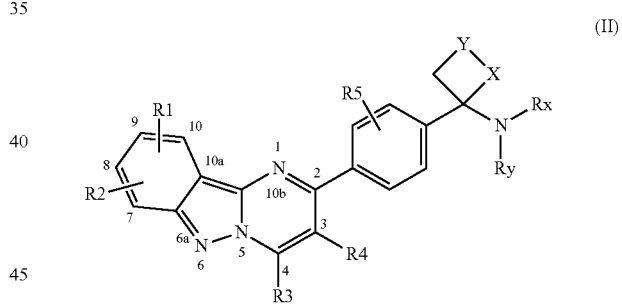

wherein
R1 is bromine in position 7, 8 or 9 of the tricyclic ring system and R2 is hydrogen and
R3, R4, R5, X, Y, have the meaning as defined in claim 1,
Rx is R6 or a protecting group, wherein R6 has the meaning as defined in claim 1,
Ry is hydrogen or a protecting group,
or Rx and Ry together form a cyclic protecting group.

7. A pharmaceutical composition comprising at least one compound of general formula (I) according to claim 1, together with at least one pharmaceutically acceptable auxiliary.

8. A combination comprising one or more first active ingredients selected from a compound of general formula (I) according to claim 1, and one or more second active ingredients selected from chemotherapeutic anti-cancer agents and target-specific anti-cancer agents.

9. A kit comprising a compound of general formula (I) according to claim 1.

10. A method for the treatment of benign or malignant neoplasia responsive to inhibition of the Pi3K/Akt pathway comprising administering to a patient in need thereof a pharmaceutically effective amount of a compound according to claim 1.

11. A method for the treatment of a disease selected from breast cancer and prostate cancer comprising administering to a patient in need thereof a pharmaceutically effective amount of a compound according to claim 1.

* * * * *